(12) United States Patent
Rothberg et al.

(10) Patent No.: US 11,719,635 B2
(45) Date of Patent: Aug. 8, 2023

(54) INTEGRATED PHOTODETECTOR WITH DIRECT BINNING PIXEL

(71) Applicant: Quantum-Si Incorporated, Guilford, CT (US)

(72) Inventors: Jonathan M. Rothberg, Guilford, CT (US); Keith G. Fife, Palo Alto, CA (US); David M. Boisvert, San Jose, CA (US)

(73) Assignee: Quantum-Si Incorporated, Guilford, CT (US)

( * ) Notice: Subject to any disclaimer, the term of this patent is extended or adjusted under 35 U.S.C. 154(b) by 0 days.

(21) Appl. No.: 17/391,473

(22) Filed: Aug. 2, 2021

(65) Prior Publication Data

US 2022/0018776 A1    Jan. 20, 2022

Related U.S. Application Data

(63) Continuation of application No. 17/071,833, filed on Oct. 15, 2020, now Pat. No. 11,112,361, which is a
(Continued)

(51) Int. Cl.
*G01N 21/64* (2006.01)
*H01L 27/146* (2006.01)
(Continued)

(52) U.S. Cl.
CPC ....... *G01N 21/6428* (2013.01); *C12Q 1/6869* (2013.01); *G01N 21/64* (2013.01);
(Continued)

(58) Field of Classification Search
CPC .............. G01N 21/6428; G01N 21/64; G01N 21/6408; G01N 21/6458; G01S 7/4865;
(Continued)

(56) References Cited

U.S. PATENT DOCUMENTS 5,198,543 A   3/1993   Blanco et al.
5,302,509 A   4/1994   Cheeseman
(Continued)

FOREIGN PATENT DOCUMENTS

CN   2433618 Y   6/2001
CN   1364940 A   8/2002
(Continued)

OTHER PUBLICATIONS

U.S. Appl. No. 16/554,751, filed Aug. 29, 2019, Cipriany.
(Continued)

*Primary Examiner* — Vu A Vu
(74) *Attorney, Agent, or Firm* — Wolf, Greenfield & Sacks, P.C.

(57) ABSTRACT

An integrated circuit includes a photodetection region configured to receive incident photons. The photodetection region is configured to produce a plurality of charge carriers in response to the incident photons. The integrated circuit includes at least one charge carrier storage region. The integrated circuit also includes a charge carrier segregation structure configured to selectively direct charge carriers of the plurality of charge carriers directly into the at least one charge carrier storage region based upon times at which the charge carriers are produced.

24 Claims, 37 Drawing Sheets

Related U.S. Application Data continuation of application No. 15/852,571, filed on Dec. 22, 2017, now Pat. No. 10,845,308.

(60) Provisional application No. 62/438,051, filed on Dec. 22, 2016.

(51) Int. Cl.
| | | |
|---|---|---|
| *C12Q 1/6869* | (2018.01) | |
| *H01L 27/148* | (2006.01) | |
| *G01S 7/4865* | (2020.01) | |
| *H04N 25/77* | (2023.01) | |

(52) U.S. Cl.
CPC ........ *G01N 21/6408* (2013.01); *G01S 7/4865* (2013.01); *H01L 27/14603* (2013.01); *H01L 27/14612* (2013.01); *H01L 27/14643* (2013.01); *H01L 27/14687* (2013.01); *H01L 27/14689* (2013.01); *H01L 27/14812* (2013.01); *H04N 25/77* (2023.01); *G01N 21/6458* (2013.01)

(58) Field of Classification Search
CPC ......... H01L 27/14603; H01L 27/14612; H01L 27/14689; H01L 27/14687; H01L 27/14643; H01L 27/14812; C12Q 1/6869; H04N 5/3745
USPC ..................................................... 422/82.08
See application file for complete search history.

(56) References Cited

U.S. PATENT DOCUMENTS

| | | |
|---|---|---|
| 5,355,165 A | 10/1994 | Kosonocky et al. |
| 5,471,515 A | 11/1995 | Fossum et al. |
| 5,674,743 A | 10/1997 | Ulmer |
| 5,822,472 A | 10/1998 | Danielzik et al. |
| 5,912,155 A | 6/1999 | Chatterjee et al. |
| 5,961,924 A | 10/1999 | Reichert et al. |
| 6,137,117 A | 10/2000 | Feldstein et al. |
| 6,198,869 B1 | 3/2001 | Kraus et al. |
| 6,210,896 B1 | 4/2001 | Chan |
| 6,232,103 B1 | 5/2001 | Short |
| 6,255,083 B1 | 7/2001 | Williams |
| 6,261,797 B1 | 7/2001 | Sorge et al. |
| 6,265,193 B1 | 7/2001 | Brandis et al. |
| 6,280,939 B1 | 8/2001 | Allen |
| 6,327,410 B1 | 12/2001 | Walt et al. |
| 6,355,420 B1 | 3/2002 | Chan |
| 6,399,320 B1 | 6/2002 | Markau et al. |
| 6,399,335 B1 | 6/2002 | Kao et al. |
| 6,437,345 B1 | 8/2002 | Bruno-Raimondi et al. |
| 6,445,491 B2 | 9/2002 | Sucha et al. |
| 6,607,883 B1 | 8/2003 | Frey et al. |
| 6,686,582 B1 | 2/2004 | Volcker et al. |
| 6,716,394 B2 | 4/2004 | Jensen et al. |
| 6,787,308 B2 | 9/2004 | Balasubramanian et al. |
| 6,825,921 B1 | 11/2004 | Modlin et al. |
| 6,917,726 B2 | 7/2005 | Levene et al. |
| 6,936,702 B2 | 8/2005 | Williams et al. |
| 6,975,898 B2 | 12/2005 | Seibel |
| 7,033,762 B2 | 4/2006 | Nelson et al. |
| 7,052,847 B2 | 5/2006 | Korlach et al. |
| 7,057,026 B2 | 6/2006 | Barnes et al. |
| 7,153,672 B1 | 12/2006 | Eickbush et al. |
| 7,158,224 B2 | 1/2007 | Montagu |
| 7,170,050 B2 | 1/2007 | Turner et al. |
| 7,175,811 B2 | 2/2007 | Bach et al. |
| 7,179,654 B2 | 2/2007 | Verdonk et al. |
| 7,270,951 B1 | 9/2007 | Stemple et al. |
| 7,345,764 B2 | 3/2008 | Bulovic et al. |
| 7,393,640 B2 | 7/2008 | Kumar et al. |
| 7,405,281 B2 | 7/2008 | Xu et al. |
| 7,426,322 B2 | 9/2008 | Hyde |
| 7,462,452 B2 | 12/2008 | Williams et al. |
| 7,595,883 B1 | 9/2009 | El Gamal et al. |
| 7,630,073 B2 | 12/2009 | Lundquist et al. |
| 7,738,086 B2 | 6/2010 | Shepard et al. |
| 7,745,116 B2 | 6/2010 | Williams |
| 7,820,983 B2 | 10/2010 | Lundquist et al. |
| 7,834,329 B2 | 11/2010 | Lundquist et al. |
| 7,838,847 B2 | 11/2010 | Lundquist et al. |
| 7,871,777 B2 | 1/2011 | Schneider et al. |
| 7,873,085 B2 | 1/2011 | Babushkin et al. |
| 7,875,440 B2 | 1/2011 | Williams et al. |
| 7,968,702 B2 | 6/2011 | Wegener et al. |
| 7,973,146 B2 | 7/2011 | Shen et al. |
| 7,981,604 B2 | 7/2011 | Quake |
| 7,995,202 B2 | 8/2011 | Lundquist et al. |
| 8,023,113 B2 | 9/2011 | El Gamal et al. |
| 8,053,742 B2 | 11/2011 | Lundquist et al. |
| 8,058,030 B2 | 11/2011 | Smith et al. |
| 8,133,672 B2 | 3/2012 | Bjornson et al. |
| 8,153,375 B2 | 4/2012 | Travers et al. |
| 8,174,696 B2 | 5/2012 | Ebbesen et al. |
| 8,207,509 B2 | 6/2012 | Lundquist et al. |
| 8,238,993 B2 | 8/2012 | Maynard et al. |
| 8,274,034 B2 | 9/2012 | Vogel et al. |
| 8,274,040 B2 | 9/2012 | Zhong et al. |
| 8,278,728 B2 | 10/2012 | Murshid |
| 8,323,939 B2 | 12/2012 | Hanzel et al. |
| 8,338,248 B2 * | 12/2012 | Kawahito ......... H01L 27/14612 257/E21.133 |
| 8,343,746 B2 | 1/2013 | Rank et al. |
| 8,465,699 B2 | 6/2013 | Fehr et al. |
| 8,471,219 B2 | 6/2013 | Lundquist et al. |
| 8,471,230 B2 | 6/2013 | Zhong et al. |
| 8,481,264 B2 | 7/2013 | Bjornson et al. |
| 8,501,406 B1 | 8/2013 | Gray et al. |
| 8,501,922 B2 | 8/2013 | Otto et al. |
| 8,502,169 B2 | 8/2013 | Rigneault et al. |
| 8,580,539 B2 | 11/2013 | Korlach |
| 8,618,507 B1 | 12/2013 | Lundquist et al. |
| 8,865,077 B2 | 10/2014 | Chiou et al. |
| 8,921,086 B2 | 12/2014 | Hanzel et al. |
| 9,029,802 B2 | 5/2015 | Lundquist et al. |
| 9,062,091 B2 | 6/2015 | Bjornson et al. |
| 9,127,259 B2 | 9/2015 | Bjornson et al. |
| 9,157,864 B2 | 10/2015 | Fehr et al. |
| 9,222,123 B2 | 12/2015 | Zhong et al. |
| 9,222,133 B2 | 12/2015 | Lundquist et al. |
| 9,223,084 B2 | 12/2015 | Grot et al. |
| 9,372,308 B1 | 6/2016 | Saxena et al. |
| 9,587,276 B2 | 3/2017 | Lundquist et al. |
| 9,606,058 B2 | 3/2017 | Rothberg et al. |
| 9,606,060 B2 | 3/2017 | Chen et al. |
| 9,658,161 B2 | 5/2017 | Saxena et al. |
| 9,666,748 B2 | 5/2017 | Leobandung |
| 9,696,258 B2 | 7/2017 | Rothberg et al. |
| 9,719,138 B2 | 8/2017 | Zhong et al. |
| 9,759,658 B2 | 9/2017 | Rothberg et al. |
| 9,765,395 B2 | 9/2017 | Goldsmith |
| 9,945,779 B2 | 4/2018 | Rothberg et al. |
| 9,946,017 B2 | 4/2018 | Saxena et al. |
| 10,018,764 B2 | 7/2018 | Grot et al. |
| 10,090,429 B2 | 10/2018 | Leobandung |
| 10,138,515 B2 | 11/2018 | Fehr et al. |
| 10,206,561 B2 * | 2/2019 | Wichem ........... A61B 1/000095 |
| 10,249,656 B2 * | 4/2019 | Panicacci ......... H01L 27/14609 |
| 10,280,457 B2 | 5/2019 | Zhong et al. |
| 10,310,178 B2 | 6/2019 | Saxena et al. |
| 10,441,174 B2 | 10/2019 | Rothberg et al. |
| 10,487,356 B2 | 11/2019 | Lundquist et al. |
| 10,578,788 B2 | 3/2020 | Grot et al. |
| 10,655,172 B2 | 5/2020 | Rank et al. |
| 10,724,090 B2 | 7/2020 | McCaffrey et al. |
| 10,775,305 B2 | 9/2020 | Rothberg et al. |
| 10,845,308 B2 | 11/2020 | Rothberg et al. |
| 11,112,361 B2 | 9/2021 | Rothberg et al. |
| 11,209,363 B2 | 12/2021 | Rothberg et al. |
| 11,344,200 B2 | 5/2022 | Rothberg et al. |
| 11,391,626 B2 | 7/2022 | Thurston et al. |
| 2001/0009269 A1 | 7/2001 | Hayashi |

(56) References Cited

U.S. PATENT DOCUMENTS

| | | |
|---|---|---|
| 2001/0017727 A1 | 8/2001 | Sucha et al. |
| 2001/0055462 A1 | 12/2001 | Seibel |
| 2002/0031836 A1 | 3/2002 | Feldstein |
| 2002/0182716 A1 | 12/2002 | Weisbuch et al. |
| 2003/0174992 A1 | 9/2003 | Levene et al. |
| 2004/0004194 A1 | 1/2004 | Amblard et al. |
| 2004/0106163 A1 | 6/2004 | Workman et al. |
| 2004/0144927 A1 | 7/2004 | Auner et al. |
| 2004/0169842 A1 | 9/2004 | Dosluoglu et al. |
| 2005/0256650 A1 | 11/2005 | Labarbe et al. |
| 2006/0019265 A1 | 1/2006 | Song et al. |
| 2006/0249657 A1 | 11/2006 | O'Grady |
| 2007/0042500 A1 | 2/2007 | Meyer-Aimes et al. |
| 2007/0250274 A1 | 10/2007 | Volkov et al. |
| 2007/0281288 A1 | 12/2007 | Belkin et al. |
| 2008/0050747 A1 | 2/2008 | Korlach et al. |
| 2008/0097174 A1 | 4/2008 | Maynard et al. |
| 2009/0014658 A1 | 1/2009 | Cottier et al. |
| 2010/0009872 A1 | 1/2010 | Eid et al. |
| 2010/0065726 A1 | 3/2010 | Zhong et al. |
| 2010/0141927 A1 | 6/2010 | Hashimoto et al. |
| 2010/0173394 A1 | 7/2010 | Colston et al. |
| 2010/0255487 A1 | 10/2010 | Beechem et al. |
| 2010/0323406 A1 | 12/2010 | Vatta et al. |
| 2011/0136201 A1 | 6/2011 | Mao et al. |
| 2011/0165652 A1 | 7/2011 | Hardin et al. |
| 2011/0187908 A1 | 8/2011 | Kawahito et al. |
| 2011/0236983 A1 | 9/2011 | Beechem et al. |
| 2011/0298079 A1 | 12/2011 | Kawahito |
| 2012/0021525 A1 | 1/2012 | Fehr et al. |
| 2012/0094332 A1 | 4/2012 | Lee et al. |
| 2012/0224053 A1 | 9/2012 | Vykoukal et al. |
| 2012/0235125 A1 | 9/2012 | Forrest et al. |
| 2012/0322692 A1 | 12/2012 | Pham et al. |
| 2013/0005047 A1 | 1/2013 | Mayer et al. |
| 2013/0023039 A1 | 1/2013 | Zaccarin et al. |
| 2013/0071849 A1 | 3/2013 | Kong et al. |
| 2013/0072768 A1 | 3/2013 | Crane et al. |
| 2013/0090537 A1 | 4/2013 | Schemmann et al. |
| 2013/0116153 A1 | 5/2013 | Bowen et al. |
| 2013/0149734 A1 | 6/2013 | Ammar et al. |
| 2013/0183676 A1 | 7/2013 | Chen et al. |
| 2013/0217007 A1 | 8/2013 | Kamtekar et al. |
| 2013/0270610 A1 | 10/2013 | Suess et al. |
| 2014/0217264 A1 | 8/2014 | Shepard et al. |
| 2014/0231879 A1 | 8/2014 | Meynants et al. |
| 2014/0252201 A1* | 9/2014 | Li .................... H04N 5/378 250/208.1 |
| 2014/0252437 A1 | 9/2014 | Oh et al. |
| 2015/0014126 A1 | 1/2015 | Snow |
| 2015/0042954 A1 | 2/2015 | Hunter et al. |
| 2015/0141267 A1 | 5/2015 | Rothberg et al. |
| 2015/0141268 A1 | 5/2015 | Rothberg et al. |
| 2015/0172526 A1 | 6/2015 | Swihart et al. |
| 2015/0173621 A1 | 6/2015 | Guo et al. |
| 2015/0293021 A1 | 10/2015 | Finkelstein et al. |
| 2015/0294998 A1 | 10/2015 | Nihtianov et al. |
| 2015/0340445 A1* | 11/2015 | Choi .................... H01L 29/36 257/292 |
| 2016/0041095 A1 | 2/2016 | Rothberg et al. |
| 2016/0084761 A1 | 3/2016 | Rothberg et al. |
| 2016/0133668 A1 | 5/2016 | Rothberg et al. |
| 2016/0181298 A1 | 6/2016 | Wan et al. |
| 2016/0338631 A1 | 11/2016 | Li et al. |
| 2016/0356718 A1 | 12/2016 | Yoon et al. |
| 2016/0377543 A1 | 12/2016 | Rothberg et al. |
| 2016/0380025 A1 | 12/2016 | Rothberg et al. |
| 2017/0107562 A1 | 4/2017 | Rothberg et al. |
| 2017/0146479 A1 | 5/2017 | Levine et al. |
| 2017/0231500 A1 | 8/2017 | Rothberg et al. |
| 2017/0322153 A1 | 11/2017 | Rothberg et al. |
| 2018/0180546 A1 | 6/2018 | Rothberg et al. |
| 2018/0259456 A1 | 9/2018 | Rothberg et al. |
| 2019/0292590 A1 | 9/2019 | Zhong et al. |
| 2019/0374107 A1 | 12/2019 | Rothberg et al. |
| 2019/0391010 A1 | 12/2019 | Thurston et al. |
| 2020/0072752 A1 | 3/2020 | Cipriany |
| 2021/0025823 A1 | 1/2021 | Rothberg et al. |
| 2021/0025824 A1 | 1/2021 | Rothberg et al. |
| 2022/0155229 A1 | 5/2022 | Rothberg et al. |
| 2022/0273174 A1 | 9/2022 | Rothberg et al. |

FOREIGN PATENT DOCUMENTS

| | | |
|---|---|---|
| CN | 1138862 C | 2/2004 |
| CN | 1867822 A | 11/2006 |
| CN | 102348406 A | 2/2012 |
| CN | 102388321 A | 3/2012 |
| CN | 102395874 A | 3/2012 |
| CN | 102713569 A | 10/2012 |
| CN | 102914525 A | 2/2013 |
| CN | 102933144 A | 2/2013 |
| CN | 103728446 A | 4/2014 |
| CN | 105300949 A | 2/2016 |
| EP | 1681356 A1 | 7/2006 |
| EP | 2182523 A1 | 5/2010 |
| EP | 2339632 A1 | 6/2011 |
| EP | 2391639 | 12/2011 |
| EP | 2134871 B1 | 3/2012 |
| EP | 2487897 A1 | 8/2012 |
| EP | 3194935 A2 | 7/2017 |
| JP | 2000-165750 A | 6/2000 |
| JP | 2002-170945 A | 6/2002 |
| JP | 2010-233843 A | 10/2010 |
| JP | 2012-132741 A | 7/2012 |
| JP | 2013-500101 A | 1/2013 |
| TW | 201248871 A | 12/2012 |
| TW | 201421655 A | 6/2014 |
| WO | WO 91/06678 A1 | 5/1991 |
| WO | WO 2004/047353 A2 | 6/2004 |
| WO | WO 2005/073407 A1 | 8/2005 |
| WO | WO 2007/015168 A2 | 2/2007 |
| WO | WO 2007/119626 A1 | 10/2007 |
| WO | WO 2010/025331 A1 | 3/2010 |
| WO | WO 2011/103497 A1 | 8/2011 |
| WO | WO 2011/103507 A1 | 8/2011 |
| WO | WO 2011/153962 A1 | 12/2011 |
| WO | WO 2013/171197 A1 | 11/2013 |
| WO | WO 2016/011534 A1 | 1/2016 |
| WO | WO 2016/022998 A2 | 2/2016 |
| WO | WO 2016/022998 A3 | 2/2016 |
| WO | WO 2016/023011 A1 | 2/2016 |
| WO | WO 2016/128198 A1 | 8/2016 |
| WO | WO 2016/187580 A1 | 11/2016 |
| WO | WO 2017/210413 A1 | 12/2017 |

OTHER PUBLICATIONS

U.S. Appl. No. 16/446,708, filed Jun. 20, 2019, Thurston et al.
U.S. Appl. No. 16/550,841, filed Aug. 26, 2019, Rothberg et al.
U.S. Appl. No. 16/984,537, filed Aug. 4, 2020, Rothberg et al.
U.S. Appl. No. 17/071,833, filed Oct. 15, 2020, Rothberg et al.
PCT/US2014/066014, Jan. 28, 2015, Invitation to Pay Additional Fees.
PCT/US2014/066014, Apr. 7, 2015, International Search Report and Written Opinion.
PCT/US2014/066014, May 26, 2016, International Preliminary Report on Patentability.
EP 15759983.8, Aug. 1, 2018, Third Party Observations.
EP 18202357.2, Mar. 15, 2019, Extended European Search Report.
PCT/US2015/044360, Nov. 20, 2015, Invitation to Pay Additional Fees.
PCT/US2015/044360, Feb. 3, 2016, International Search Report and Written Opinion.
PCT/US2015/044378, Oct. 30, 2015, Invitation to Pay Additional Fees.
PCT/US2015/044378, Jan. 15, 2016, International Search Report and Written Opinion.
PCT/US2015/044379, Nov. 2, 2015, Invitation to Pay Additional Fees.
PCT/US2015/044379, Jan. 15, 2016, International Search Report and Written Opinion.

(56) References Cited

OTHER PUBLICATIONS

PCT/US2014/066013, Jan. 28, 2015, Invitation to Pay Additional Fees.
PCT/US2014/066013, Apr. 7, 2015, International Search Report and Written Opinion.
PCT/US2014/066013, May 26, 2016, International Preliminary Report on Patentability.
PCT/US2014/066010, Jan. 28, 2015, Invitation to Pay Additional Fees.
PCT/US2014/066010, Apr. 7, 2015 International Search Report and Written Opinion.
PCT/US2014/066010, May 26, 2016, International Preliminary Report on Patentability.
PCT/US2017/068089, Mar. 27, 2018, International Search Report and Written Opinion.
PCT/US2019/038105, Sep. 16, 2019, Invitation to Pay Additional Fees.
EP 17753881.6, Sep. 19, 2019, Extended European Search Report.
PCT/US17/18278, Apr. 25, 2017, International Search Report and Written Opinion.
PCT/US2017/018278, Aug. 30, 2018, International Preliminary Report on Patentability.
PCT/US2019/038105, Nov. 26, 2019, International Search Report and Written Opinion.
PCT/US2019/048824, Dec. 9, 2019, Invitation to Pay Additional Fees.
PCT/US2019/048824, Jan. 31, 2020, International Search Report and Written Opinion.
PCT/US2019/038105, Dec. 30, 2020, International Preliminary Report on Patentability.
PCT/US2019/048824, Mar. 11, 2021, International Preliminary Report on Patentability.
PCT/US2017/068089, Jul. 4, 2019, International Preliminary Report on Patentability.
Invitation to Pay Additional Fees for International Application No. PCT/US2014/066014 mailed Jan. 28, 2015.
International Search Report and Written Opinion for International Application No. PCT/US2014/066014 dated Apr. 7, 2015.
International Preliminary Report on Patentability for International Application No. PCT/US2014/066014 dated May 26, 2016.
Invitation to Pay Additional Fees for International Application No. PCT/US2015/044360 mailed Nov. 20, 2015.
International Search Report and Written Opinion for International Application No. PCT/US2015/044360 dated Feb. 3, 2016.
Invitation to Pay Additional Fees for International Application No. PCT/US2015/044378 mailed Oct. 30, 2015.
International Search Report and Written Opinion for International Application No. PCT/US2015/044378 dated Jan. 15, 2016.
Invitation to Pay Additional Fees for International Application No. PCT/US2015/044379 mailed Nov. 2, 2015.
International Search Report and Written Opinion for International Application No. PCT/US2015/044379 dated Jan. 15, 2016.
Invitation to Pay Additional Fees for International Application No. PCT/US2014/066013 mailed Jan. 28, 2015.
International Search Report and Written Opinion for International Application No. PCT/US2014/066013 dated Apr. 7, 2015.
International Preliminary Report on Patentability for International Application No. PCT/US2014/066013 dated May 26, 2016.
Invitation to Pay Additional Fees for International Application No. PCT/US2014/066010 mailed Jan. 28, 2015.
International Search Report and Written Opinion for International Application No. PCT/US2014/066010 dated Apr. 7, 2015.
International Preliminary Report on Patentability for International Application No. PCT/US2014/066010 dated May 26, 2016.
International Search Report and Written Opinion for International Application No. PCT/US2017/068089 dated Mar. 27, 2018.
Third Party Observations for European Application No. 15759983.8 dated Aug. 1, 2018.
International Search Report and Written Opinion for International Application No. PCT/US17/18278 dated Apr. 25, 2017.
Extended European Search Report for European Application No. 18202357.2 dated Mar. 15, 2019.
Invitation to Pay Additional Fees for International Application No. PCT/US2019/038105 mailed Sep. 16, 2019.
International Preliminary Report on Patentability for International Application No. PCT/US2017/018278 dated Aug. 30, 2018.
Extended European Search Report for European Application No. 17753881.6 dated Sep. 19, 2019.
International Search Report and Written Opinion for International Application No. PCT/US2019/038105 dated Nov. 26, 2019.
Invitation to Pay Additional Fees for International Application No. PCT/US2019/048824 mailed Dec. 9, 2019.
International Search Report and Written Opinion for International Application No. PCT/US2019/048824 dated Jan. 31, 2020.
International Preliminary Report on Patentability for International Application No. PCT/US2019/038105 dated Dec. 30, 2020.
International Preliminary Report on Patentability for International Application No. PCT/US2019/048824 dated Mar. 11, 2021.
International Preliminary Report on Patentability for International Application No. PCT/US2017/068089, dated Jul. 4, 2019.
[No Author Listed] 5.2 Megapixels, 1-inch, 250fps, glob al-shutter CMOS image sensor, Anafocus, Oct. 2012, 4 pages, Sevilla, Spain.
[No Author Listed] Description of our technology, CrackerBio, 4 pages, Taiwan.
[No Author Listed] Detect Cancer with our 4 Picos ICCD camera, Stanford Computer Optics, 2013, 2 pages, http://www.stanfordcomputeroptics.com/applications/life-science/time-resolved-flim.html [last accessed May 9, 2014].
[No Author Listed] ICCD camera applications in the field of Life Science, Stanford Computer Optics, 2013, 2 pages, http://www.stanfordcomputeroptics.com/applications/life-science.html [last accessed May 9, 2014].
[No Author Listed] OLED-on-CMOS for Sensors and Microdisplays, IPMS Fraunhofer Institut Photonische Mikrosysteme, 2 pages, Dresden, Germany.
Achermann, Exciton—Plasmon Interactions in Metal—Semiconductor Nanostructures, The Journal Physical Chemistry Letters, Sep. 13, 2010, 1(19):2837-43.
Akselrod et al, Twenty-fold enhancement of molecular fluorescence by coupling to a J-aggregate critically coupled resonator. ACS Nano. Jan. 24, 2012;6(1):467-71. doi: 10.1021/nn203789t. Epub Dec. 1, 2011.
Algar et al., Interfacial Chemistry and the Design of Solid-Phase Nucleic Acid Hybridization Assays Using Immobilized Quantum Dots as Donors in Fluorescence Resonance Energy Transfer, Sensors, Jun. 2011, 11(6):6214-36.
Aouani et al., Bright unidirectional fluorescence emission of molecules in a nanoaperture with plasmonic corrugations. Nano Lett. Feb. 9, 2011;11(2):637-44. doi: 10.1021/nl103738d. Epub Jan. 19, 2011.
Aouani et al., Plasmonic Antennas for Directional Sorting of Fluorescence Emission, Nano Letters, May 18, 2011, 11(6):2400-6.
Aouani et al., Saturated excitation of fluorescence to quantify excitation enhancement in aperture antennas, Optics Express, Jul. 30, 2012, 20(16):18085-90.
Aouani et al., Supporting Information for Bright unidirectional fluorescence emission of molecules in a nanoaperture with plasmonic corrugations. Nano Lett. Feb. 9, 2011;11(2):19 pages.
Aouani et al., Supporting Information for Plasmonic Antennas for Directional Sorting of Fluorescence Emission, Nano Letters, May 18, 2011, 11(6):9 pages.
Bergman et al., Surface Plasmon Amplification by Stimulated Emission of Radiation: Quantum Generation of Coherent Surface Plasmons in Nanosystems, Physical Review Letters, Jan. 17, 2013, 90(2):027402-1-4.
Bogaerts et al., High speed 36 Gbps 12Mpixel global pipelined shutter CMOS image sensor with CDS, 2011 International Image Sensor Workshop, Jun. 8-11, 2011, 4 pages, Hokkaido, Japan.
Carretero-Palacious et al., Mechanisms for extraordinary optical transmission through bull's eye structures, Optics Express, May 23, 2011, 19(11):10429-42.

(56) References Cited

OTHER PUBLICATIONS

Chanyawadee et al., Nonradiative exciton energy transfer in hybrid organic-inorganic heterostructures, Phys. Rev. B., May 14, 2008, 77(19): 193402-1-4.

Daldosso et al., Fabrication and optical characterization of thin two-dimensional Si3N4 waveguides, Materials Science in Semiconductor Processing, Oct. 18, 2004, 7(4-6): 453-8.

Davies et al., Plasmonic Nanogap Tilings: Light-Concentrating Surfaces for Low-Loss Photonic Integration, ACS Nano, Jul. 4, 2013, 7(8):7093-100, arXiv:1305.2839v2, http://arxiv.org/abs/1305.2839v2.

Deshpande et al., Electrically driven polarized single-photon emission from an InGaN quantum dot in a GaN nanowire, Nature Communications, Apr. 9, 2013, 8 pages.

Deutsch et al., Luminescence upconversion in colloidal double quantum dots, Nature Nanotechnology Letter, Sep. 2013, 8(9):649-53.

Edel et al., Accurate Single Molecule FRET Efficiency Determination for Surface Immobilized DNA Using Maximum Likelihood Calculated Lifetimes, J. Phys. Chem, Mar. 22, 2007, 111(11):2986-90.

Eggeling et al., Monitoring conformational dynamics of a single molecule by selective fluorescence spectroscopy. Proc. Natl. Acad. Sci. 1998;95:1556-61.

Eid et al., Real-time DNA sequencing from single polymerase molecules. Science. Jan. 2, 2009;323(5910):133-8. doi:10.1126/science.1162986. Epub Nov. 20, 2008.

Eid et al., Supporting Online Material for Real-time DNA sequencing from single polymerase molecules. Science. Jan. 2, 2009;323(5910):21 pages.

Feldman et al., Wafer-Level Camera Technologies Shrink Camera Phone Handsets, Photonics.com, Aug. 1, 2007, 3 pages, http://www.photonics.com/Article.aspx?AID=30459 . [last accessed Dec. 17, 2013].

Fu et al., A microfabricated fluorescence-activated cell sorter. Nature Biotechnology. Nov. 1999; 17(11): 1109-1111.

Gorin et al., Fabrication of silicon nitride waveguides for visible-light using PECVD: a study of the effect of plasma frequency on optical properties, Optics Express, Sep. 1, 2008, 16(18):13509-16.

Gryczynski et al., Two-photon excitation by the evanescent wave from total internal reflection. Anal Biochem., Apr. 5, 1997;247(1):69-76.

Haase et al., Upconverting Nanoparticles, Angewandte Chemie International Edition, Jun. 20, 2011, 50(26):5808-29.

Hale, Fibre Optic Sensors using Adiabatically Tapered Single Mode Fibres. Dissertation submitted to the University of Cambridge. Feb. 1994. 209 pages.

Hallman et al., 3 nJ, 100 ps laser pulses generated with an asymmetric waveguide laser diode for a single-photon avalanche diode time-of-flight (SPAD TOF) rangefinder application, Measurement Science and Technology, Jan. 5, 2012, 23(2): 8 pages.

Hansard et al., Time-of-Flight Cameras: Principles, Methods and Applications, Nov. 2012, 102 pages, Springer-Verlag, London, UK.

He et al., DNA Sequencing by Capillary Electrophoresis with Four-Decay Fluorescence Detection, Anal. Chem., Dec. 15, 2000, 72(24):5865-73.

Herold et al., OLED-on-CMOS Integration for Augmented-Reality Systems, IEEE 2008 International Students and Young Scientists Workshop Photonics and Microsystems, Jun. 20-22, 2008, 19-22, Wroclaw—Szlarska Poreba, Poland.

Heucke et al., Placing Individual Molecules in the Center of Nanoapertures, Nano Letters, Feb. 12, 2014, 14(2):391-5.

Inoue et al., CMOS active pixel image sensor with in-pixel CDS for high-speed cameras, Proc. SPIE, Sensors and Camera Systems for Scientific, Industrial, and Digital Photography Applications V, 250, Jun. 7, 2004, 5301(4):8 pages.

Ishii et al., Self-matched high-voltage rectangular wave pulse generator, Rev. Sci. Instrum, Nov. 1985, 56(11):2116-8.

Jun et al., Plasmonic beaming and active control over fluorescent emission, Nature Communications, Apr. 19, 2011, 6 pages.

Juodawlkis et al., High-Power, Low-Noise Slab-Coupled Optical Waveguide (SCOW) Amplifiers and Lasers, IEEE Optical Society of America Optical Fiber Communication Conference and Exposition and the National FiberOptic Engineers Conference, Mar. 6-10, 2011, 3 pages, Los Angeles, CA.

Juodawlkis et al., High-Power, Ultralow-Noise Semiconductor External Cavity Lasers Based on Low-Confinement Optical Waveguide Gain Media, Proc. of SPIE Novel In-Plane Semiconductor Lasers IX, Feb. 12, 2010, vol. 7616:76160X-1-9.

Kano et al., Two-photon-excited fluorescence enhanced by a surface plasmon. Opt Lett. Nov. 15, 1996;21(22):1848-50.

Karow, PacBio Aims to Boost Throughput of SMRT Technology with Microchip Co-development Deal, In Sequence and Clinical Sequencing News, Jul. 24, 2012, 3 pages, GenomeWeb.

Klein et al., Controlling plasmonic hot spots by interfering Airy beams, Optics Letters, Aug. 15, 2012, 37(16): 3402-4.

Korlach et al., Real-time DNA sequencing from single polymerase molecules. Methods Enzymol. May 2010;472:431-55. doi:10.1016/S0076-6879(10)72001-2.

Kreye et al, P-200: Evaluation of different OLED-Stacks for Active-Matrix OLED Microdisplays on CMOS-Substrates, SID 06 Digest, Jun. 2006, 37(1); 979-81.

Kumar et al., Terminal phosphate labeled nucleotides: synthesis, applications, and linker effect on incorporation by DNA polymerases. Nucleosides Nucleotides Nucleic Acids. Nov. 2005;24(5-7):401-8.

Lenne et al., Fluorescence fluctuations analysis in nanoapertures: physical concepts and biological applications, Histochem Cell Biol, Sep. 2008, 130:795-805.

Leslie et al., Convex Lens-Induced Confinement for Imaging Single Molecules, Anal. Chem., Jul. 15, 2010, 82(14):6224-9.

Levy et al., An 852x600 Pixel OLED-on-Silicon Color Microdisplay Using CMOS Subthreshold-Voltage-Scaling Current Drivers, IEEE Journal of Solid-State Circuits, Dec. 2002, 37(12): 1879-89.

Lezec et al., Beaming Light from a Subwavelength Aperture, Science, Aug. 2, 2002, 297(5582):820-2.

Li et al., Employing ~100% Excitons in OLEDs by Utilizing a Fluorescent Molecule with Hybridized Local and Charge-Transfer Excited State, Advanced Functional Materials, Mar. 19, 2014, 24(11):1609-14.

Li et al., Time-Domain Fluorescence Lifetime Imaging Techniques Suitable for Solid-State Imaging Sensor Arrays. Sensors. 2012;12(12):5651-5653. DOI: 10.3390/s120505650.

Lin et al., Cosine-Gauss Plasmon Beam: A Localized Long-Range Nondiffracting Surface Wave, Physical Review Letters, Aug. 31, 2012, 109(9):093904-1-5.

McGinty et al., Wide-field fluorescence lifetime imaging of cancer, Biomedical Optics Express, Sep. 1, 2010, 1(2): 627-40.

Misra et al., White organic LEDs and their recent advancements, Semiconductor Science and Technology, Apr. 25, 2006, 21(7):R35-47.

Mitchell et al., Nanosecond Fluorescence Lifetime Imaging with gated CCD detection and pulsed laser excitation, Photonic Research Systems Ltd., May 1, 2013, 13 pages, Newhaven East Sussex UK.

Mogensen et al., A Microfluidic Device with an Integrated Waveguide Beam Splitter for Velocity Measurements of Flowing Particles by Fourier Transformation. Analytical Chemistry. Sep. 15, 2003;75(18):4931-4936.

Murshid et al., Array of concentric CMOS photodiodes for detection and de-multiplexing of spatially modulated optical channels, Optics & Laser Technology, Sep. 2009, 41(6):764-9.

Murshid et al., CMOS Detectors: Concentric photodiode array enables spatial-domain multiplexing, Laser Focus World, Apr. 1, 2009, 10 pages, http://www.laserfocusworld.com/articles/print/volume-45/issue-4/features/cmos-detectors-concentric-photodiode-array-enables-spatial-domain-multiplexing.html, [last accessed Dec. 12, 2013].

Murshid et al., Concentric octagonal CMOS photodiodes for direct detection of spatially multiplexed optical fiber channels, Optical Society of America, Oct. 2008, 1 page.

Nozik, Multiple exciton generation in semiconductor quantum dots, Chemical Physics Letters, May 20, 2008, 457(1-3):3-11.

Park et al., A dual-modality optical coherence tomography and fluorescence lifetime imaging microscopy system for simultaneous

(56) References Cited

OTHER PUBLICATIONS morphological and biochemical tissue characterization, Biochemical Optics Express, Aug. 2, 2010, 1(1):186-200.
Pfeifer et al., Improved optical outcoupling of OLED microdisplays by nanostructured substrates, IEEE Semiconductor Conference Dresden, Sep. 27-18, 2011, 4 pages, Dresden, Germany.
Poddubny et al., Photonic quasicrystalline and aperiodic structures, Physica E: Low-dimensional Systems and Nanostructures, May 2010, 42(7): 1871-95.
Pons et al., Solution-phase single quantum dot fluorescence resonance energy transfer. J Am Chem Soc., Nov. 29, 2006;128(47):15324-31.
Pudavar, Fluorescence Lifetime Imaging (FILM), Leica Microsystems Inc., Oct. 25, 2009, 60 pages, Exton, PA.
Punj et al., Plasmonic antennas and zero-mode waveguides to enhance single molecule fluorescence detection and fluorescence correlation spectroscopy toward physiological concentrations. Wiley Interdiscip Rev Nanomed Nanobiotechnol. May-Jun. 2014;6(3):268-82. doi: 10.1002/wnan.1261. Epub Feb. 24, 2014.
Ramuz et al., Coupling light from an organic light emitting diode (OLED) into a single-mode waveguide: Toward monolithically integrated optical sensors, Journal of Applied Physics, Apr. 2009, 105(8):084508-1-7.
Ran et al., Design of a 16 gray scales 320 x 240 pixels OLED-on-silicon driving circuit, Journal of Semiconductors, Jan. 2009, 30(1):015010-1-4.
Reckziegel et al., Optical sensors based on monlithic integrated organic light-emitting diodes (OLEDs), Proceedings of SPIE Optical Sensors, Apr. 28, 2008, vol. 7003: 8 pages.
Richter et al., Bidirectional OLED microdisplay: Combining display and image sensor functionality into a monolithic CMOS chip, 2011 IEEE International Solid-State Circuits Conference Digest of Technical Papers (ISSCC), Feb. 20-24, 2011, 3 pages, San Francisco, CA.
Richter et al., OLED-on-CMOS based bidirectional microdisplay for near-to-eye and sensor applications, IEEE Semiconductor Conference Dresden, Sep. 27-28, 2011, 3 pages, Dresden, Germany.
Rigneault et al., Enhancement of Single-Molecule Fluorescence Detection in Subwavelength Apertures, Physical Review Letters, Sep. 9, 2005, 95(11): 117401-1-4.
Romero-Garcia et al., Silicon nitride back-end optics for biosensor applications, Proc. of SPIE Integrated Optics: Physics and Simulations, May 7, 2013, vol. 8781: 87810W-1-11.
Romero-Garcia et al., Visible wavelength silicon nitride focusing grating coupler with AlCu/TiN reflector. Optics Letters. Jul. 15, 2013, 38(14):2521-3.
Rui et al., Demonstration of beam steering via dipole-coupled plasmonic spiral antennas, Scientific Reports, Jul. 19, 2013, 7 pages.
Sakadzic et al., Multi-photon microscopy with a low-cost and highly efficient Cr:LiCAF laser, Optics Express, Dec. 8, 2008, 16(25):20848-63.
Salthouse et al., Development of a Time Domain Fluorimeter for Fluorescent Lifetime Multiplexing Analysis, IEEE Biomed Circuits Syst., Sep. 1, 2008, 2(3): 204-11.
Schalberger et al., 60.4: Distinguished Paper: A Fully Integrated 1" AMOLED Display Using Current Feedback Based on a Five Mask LTPS CMOS Process, SID 10 Digest, May 2010, 41(1): 905-8.
Schmidt, Direct Encapsulation of OLED on CMOS, Bio and Nano Packaging Techniques for Electron Devices, Jul. 17, 2012, Chapter 29, 581-99, Springer-Verlag Berling Heidelberg.
Siegfried et al., Gap Plasmons and Near-Field Enhancement in Closely Packed Sub-10 nm Gap Resonators, Nano Lett., Oct. 10, 2013, 13(11):5449-53.
Sorokina et al., Fluorescent Lifetime Trajectories of a Single Fluorophore Reveal Reaction Intermediates During Transcription Initiation, J. Am. Chem. Soc., Jul. 22, 2009, 131(28):9630-31.
Sorokina et al., Supporting Information for Fluorescent Lifetime Trajectories of a Single Fluorophore Reveal Reaction Intermediates During Transcription Initiation, J. Am. Chem. Soc., Jul. 22, 2009, 131(28):4 pages.
Sun et al., Fluorescence lifetime imaging microscopy (FLIM) for image guided surgery, Stanford Computer Optics, 2013, 2 pages, http://www.stanfordcomputeroptics.com/applications/life-science/flim-guided-surgery.html, [last accessed May 9, 2014].
Sun et al., Fluorescence lifetime imaging microscopy for brain tumor image-guided surgery. Journal of Biomedical Optics. 2010;15(5):1-5.
Sun et al., Needle-compatible single fiber bundle image guide reflectance endoscope. JBO Letters. 2010; 15(4):1-3.
Taitt et al., Evanescent wave fluorescence biosensors. Biosens Bioelectron. Jun. 2005;20(12):2470-87. Epub Dec. 8, 2004.
Takkellapati et al., Synthesis of aminomethyl- and bis-aminomethyl-fluorescein energy transfer terminators. Nucleosides Nucleotides Nucleic Acids. Dec. 2007;26(10-12):1467-70.
Toerker et al., Integration of Top-Emitting Organic Light Emitting Diodes on CMOS Substrates, Proc. of SPIE Organic Optoelectronics and Photonics III, Apr. 16, 2008, vol. 6999, 4 pages.
Toma et al., Compact surface plasmon-enhanced fluorescence biochip, Opt. Express Apr. 22, 2013, 21(8): 10121-10132.
Toma et al., Surface plasmon-coupled emission on plasmonic Bragg gratings, Optics Express, Jun. 18, 2012, 20(13):14042-53.
Uhring et al., 200 ps FWHM and 100 MHz Repetition Rate Ultrafast Gated Camera for Optical Medical Functional Imaging, Proc. of SPIE Optical Sensing and Detection II, May 9, 2012, vol. 8439, 10 pages.
Unfricht et al., Grating-coupled surface plasmon resonance: a cell and protein microarray platform. Proteomics. Nov. 2005;5(17):4432-42.
Vogel et al., OLED-on-CMOS Integration for Optoelectronic Sensor Applications, Proc. of SPIE Silicon Photonics II, Mar. 1, 2007, vol. 6477:8 pages.
Vogel et al., Optoelectronic Sensors based on OLED-on-CMOS, 2008 2nd European Conference & Exhibition on Integration Issues of Minaturized Systems—MOMS, MOEMS, ICS, and Electronic Components (SSI), Apr. 9-10, 2008, 3 pages, Barcelona, Spain.
Von Ketteler et al., Fluorescence Lifetime-Based Glucose Sensing using NADH, Proc. of SPIE Optical Diagnostics and Sensing XII: Toward Point-of-Care Diagnostics; and Design and Performance Validation of Phantoms Used in Conjunction with Optical Measurement of Tissue IV, Feb. 1, 2012, vol. 8229, 8 pages.
Walpole, Slab-coupled optical waveguide lasers: a review, Proc. SPIE Novel In-Plane Semiconductor Lasers III, May 11, 2004, vol. 5365, 124-32.
Wenger et al., Emission and excitation contributions to enhanced single molecule fluorescence by gold nanometric apertures, Optics Express, Mar. 3, 2008, 16(5):3008-20.
Wenger et al., Enhanced fluorescence from metal nanoapertures: physical characterizations and biophotonic applications, Proc. SPIE Plasmonics in Biology and Medicine VII, Feb. 16, 2010, 8 pages.
Wenger, Aperture optical antennas, Optical Antennas, Feb. 2013, 25pages, Cambridge University Press, Cambridge, UK.
Willoughby, Elastically Averaged Precision Alignment, Massachusetts Institute of Technology, Jun. 2005, 158 pages, Cambridge, MA.
Xiong et al., Aluminum nitrade as a new material for chip-scale optomechanics and nonlinear optics, New Journal of Physics, Sep. 17, 2012, 14: 21 pages.
Yan-Yan et al., OLED-on-silicon chip with new pixel circuit, J. Cent. South Univ., May 2012 19(5):1276-82.
Yu et al., Light Propagation with Phase Discontinuities: Generalized Laws of Reflection and Refraction, Science, Oct. 21, 2011, 334 (6054):333-7.
Yuk et al. Analysis of immunoarrays using a gold grating-based dual mode surface plasmon-coupled emission (SPCE) sensor chip. Analyst. Jun. 7, 2012;137(11):2574-81. doi: 10.1039/c2an35143a. Epub Apr. 13, 2012.
Zhang et al., Continuous metal plasmonic frequency selective surfaces, Optics Express, Nov. 7, 2011, 19(23):23279-85.
Zhao et al., Plasmonic demultiplexer and guiding. ACS Nano. Nov. 23, 2010;4(11):6433-8. doi: 10.1021/nn101334a. Epub Oct. 6, 2010.
Zhu et al., Zero-Mode Waveguides for Single-Molecule Analysis, Annu. Rev. Biophys., Jun. 2012, 41:269-93.

(56) References Cited

OTHER PUBLICATIONS

Zong et al., Equivalent Circuit Model of Top-emitting OLED for the Designing of OLED-on-Silicon Microdisplay, Advanced Materials Research, Nov. 2011, 383-90:7037-42.
U.S. Appl. No. 17/533,170, filed Nov. 23, 2021, Rothberg et al.
U.S. Appl. No. 17/744,126, filed May 13, 2022, Rothberg et al.
U.S. Appl. No. 17/839,698, filed Jun. 14, 2022, Thurston et al.

* cited by examiner

INTEGRATED PHOTODETECTOR WITH DIRECT BINNING PIXEL

RELATED APPLICATIONS

This application is a continuation of U.S. patent application Ser. No. 17/071,833, titled "INTEGRATED PHOTODETECTOR WITH DIRECT BINNING PIXEL," filed Oct. 15, 2020, which claims priority to and is a continuation of U.S. patent application Ser. No. 15/852,571, titled "INTEGRATED PHOTODETECTOR WITH DIRECT BINNING PIXEL," filed Dec. 22, 2017, which claims priority to U.S. provisional patent application Ser. No. 62/438,051, titled "INTEGRATED PHOTODETECTOR WITH DIRECT BINNING PIXEL," filed Dec. 22, 2016, each of which is hereby incorporated by reference in its entirety.

This application is related to U.S. non-provisional application Ser. No. 14/821,656, titled "INTEGRATED DEVICE FOR TEMPORAL BINNING OF RECEIVED PHOTONS," filed Aug. 7, 2015, which is hereby incorporated by reference in its entirety.

BACKGROUND

Photodetectors are used to detect light in a variety of applications. Integrated photodetectors have been developed that produce an electrical signal indicative of the intensity of incident light. Integrated photodetectors for imaging applications include an array of pixels to detect the intensity of light received from across a scene. Examples of integrated photodetectors include charge coupled devices (CCDs) and Complementary Metal Oxide Semiconductor (CMOS) image sensors.

SUMMARY

Some embodiments relate to an integrated circuit, comprising: a photodetection region configured to receive incident photons, the photodetection region being configured to produce a plurality of charge carriers in response to the incident photons; at least one charge carrier storage region; and a charge carrier segregation structure configured to selectively direct charge carriers of the plurality of charge carriers directly into the at least one charge carrier storage region based upon times at which the charge carriers are produced.

Some embodiments relate to an integrated circuit, comprising: a direct binning pixel, comprising: a photodetection region configured to receive incident photons, the photodetection region being configured to produce a plurality of charge carriers in response to the incident photons; at least one charge carrier storage region; and a charge carrier segregation structure configured to selectively direct charge carriers of the plurality of charge carriers into the at least one charge carrier storage region based upon times at which the charge carriers are produced.

Some embodiments relate to an integrated circuit, comprising: a plurality of pixels, a first pixel of the plurality of pixels being a direct binning pixel comprising: a photodetection region configured to receive incident photons, the photodetection region being configured to produce a plurality of charge carriers in response to the incident photons; a plurality of charge carrier storage regions; and a charge carrier segregation structure configured to selectively direct charge carriers of the plurality of charge carriers directly into respective charge carrier storage regions of the plurality of charge carrier storage regions based upon times at which the charge carriers are produced, and to aggregate, in the plurality of charge carrier storage regions, charge carriers produced in a plurality of measurement periods.

Some embodiments relate to a photodetection method, comprising: (A) receiving incident photons at a photodetection region; and (B) selectively directing charge carriers of a plurality of charge carriers produced in response to the incident photons directly from the photodetection region into at least one charge carrier storage region based upon times at which the charge carriers are produced.

The charge carrier segregation structure may comprise at least one electrode at a boundary between the photodetection region and a first charge carrier storage region of the at least one charge carrier storage region.

The charge carrier segregation structure may comprise a single electrode at the boundary between the photodetection region and the first charge carrier storage region.

In some embodiments, no charge carrier capture region is present in the direct binning pixel and/or no charge carrier capture region is present between the photodetection region and a charge carrier storage region.

Charge carriers may be transferred to the at least one charge carrier storage region without capturing the carriers between the photodetection region and the at least one charge carrier storage region.

A charge carrier rejection region may discard charge carriers produced in the photodetection region during a rejection period.

The discarded charge carriers may be removed from the photodetection region in a different direction from a direction in which carriers are directed from the photodetection region toward a charge carrier storage region.

A charge carrier rejection region may discard charge carriers produced in the photodetection region during a rejection period by changing a voltage of an electrode at a boundary between the photodetection region and the charge carrier rejection region.

Single photons may be transferred to the at least one charge carrier storage region and aggregated in the at least one charge carrier storage region.

Charge carriers deeper than one micron below a surface of a semiconductor substrate may be rejected.

Charge carriers deeper than one micron below the surface of a semiconductor substrate may be rejected at least partially by an implant below a photodiode of the photodetection region.

The implant may provide a deep shield or a deep drain.

The implant may be N-type or P+-type.

Charge carriers deeper than one micron below the surface of a semiconductor substrate may be rejected by a drift field below the surface of the semiconductor substrate.

The photodetection region may be formed in an epitaxial region that is less than two microns deep.

The photodetection region may be an epitaxial region comprising a photodiode.

Charge carriers in the photodiode may be transferred to a rejection region during a rejection period, then a first potential barrier to a first charge carrier storage region may be lowered, then a second potential barrier to a second charge carrier storage region may be lowered.

The first potential barrier may be controlled by a first electrode and the second potential barrier may be controlled by a second electrode.

The at least one charge carrier storage region may comprise a plurality of charge carrier storage regions.

The foregoing summary is provided by way of illustration and is not intended to be limiting.

BRIEF DESCRIPTION OF DRAWINGS

In the drawings, each identical or nearly identical component that is illustrated in various figures is represented by a like reference character. For purposes of clarity, not every component may be labeled in every drawing. The drawings are not necessarily drawn to scale, with emphasis instead being placed on illustrating various aspects of the techniques and devices described herein.

FIG. 28 shows a first level, FIG. 29 shows a second level, FIG. 30 shows a third level, FIG. 31 shows a fourth level and FIG. 32 shows a fifth level.

DETAILED DESCRIPTION

Figure 1A:
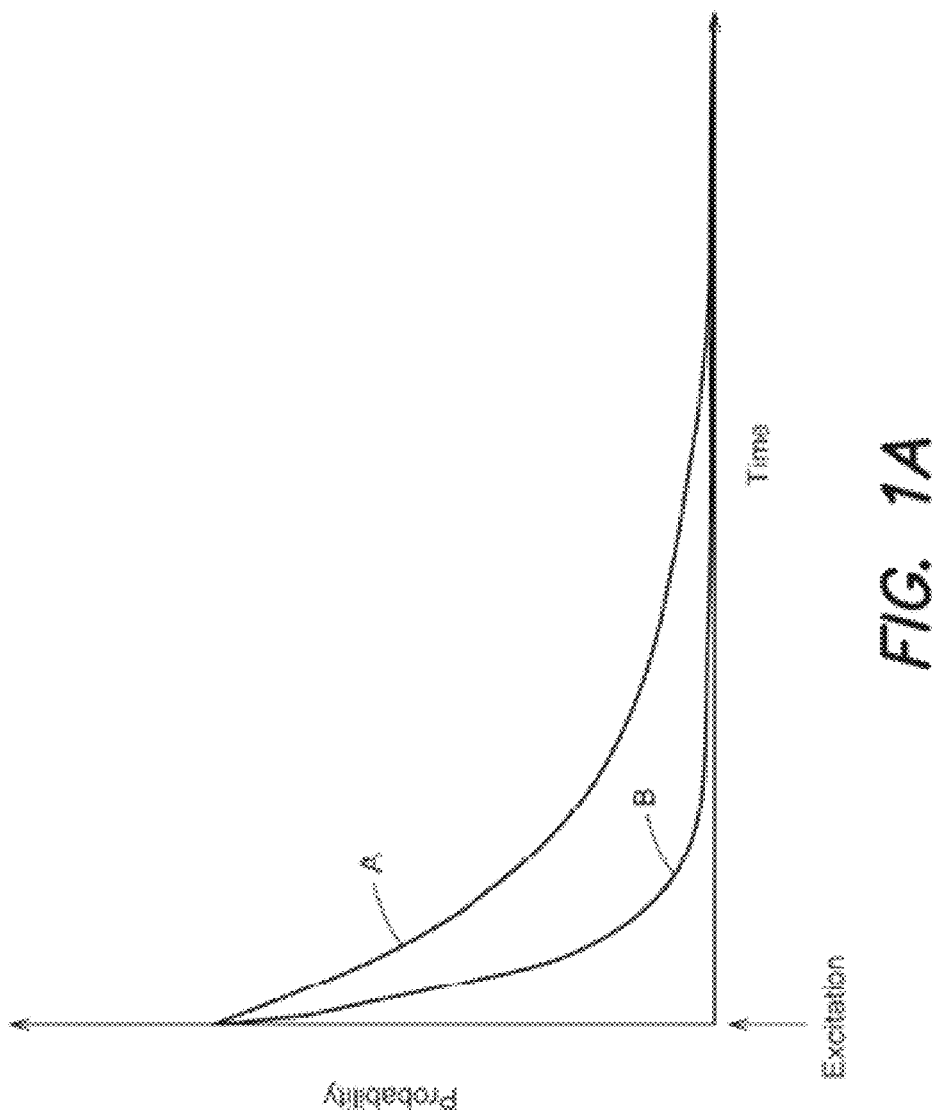
FIG. 1A plots the probability of a photon being emitted as a function of time for two markers with different lifetimes.

Described herein is an integrated photodetector that can accurately measure, or "time-bin," the timing of arrival of incident photons. In some embodiments, the integrated photodetector can measure the arrival of photons with nanosecond or picosecond resolution. Such a photodetector may find application in a variety of applications including molecular detection/quantitation, which may be applied to sequencing of nucleic acids (e.g., DNA sequencing). Such a photodetector can facilitate time-domain analysis of the arrival of incident photons from luminescent molecules used to label nucleotides, thereby enabling identification and sequencing of nucleotides based upon luminance lifetimes. Other examples of applications of the integrated photodetector include fluorescence lifetime imaging and time-of-flight imaging, as discussed further below.

Discussion of Time Domain Measurements for Molecular Detection/Quantitation

Detection and quantitation of biological samples may be performed using biological assays ("bioassays"). Bioassays conventionally involve large, expensive laboratory equipment requiring research scientists trained to operate the equipment and perform the bioassays. Bioassays are conventionally performed in bulk such that a large amount of a particular type of sample is necessary for detection and quantitation. Some bioassays are performed by tagging samples with luminescent markers that emit light of a particular wavelength. The samples are illuminated with a light source to cause luminescence, and the luminescent light is detected with a photodetector to quantify the amount of light emitted by the markers. Bioassays using luminescent tags and/or reporters conventionally involve expensive laser light sources to illuminate samples and complicated luminescent detection optics and electronics to collect the light from the illuminated samples.

In some embodiments, an integrated photodetector as described herein can detect the luminance characteristics of biological and/or chemical sample(s) in response to excitation. More specifically, such an integrated photodetector can detect the temporal characteristics of light received from the sample(s). Such an integrated photodetector can enable detecting and/or discriminating the luminance lifetime, e.g., the fluorescence lifetime, of light emitted by a luminescent molecule in response to excitation. In some embodiments, identification and/or quantitative measurements of sample(s) can be performed based on detecting and/or discriminating luminance lifetimes. For example, in some embodiments sequencing of a nucleic acid (e.g., DNA, RNA) may be performed by detecting and/or discriminating luminance lifetimes of luminescent molecules attached to respective nucleotides. Each luminescent molecule may be directly attached (e.g., bonded) to a corresponding nucleotide or indirectly attached to a corresponding nucleotide via a linker molecule that is bonded to the nucleotide and the luminescent molecule.

In some embodiments, an integrated photodetector having a number of photodetection structures and associated electronics, termed "pixels," can enable measurement and analysis of a plurality of samples in parallel (e.g., hundreds, thousands, millions or more), which can reduce the cost of performing complex measurements and rapidly advance the rate of discoveries. In some embodiments, each pixel of the photodetector may detect light from a sample, which may be a single molecule or more than one molecule. In some embodiments, such an integrated photodetector can be used for dynamic real time applications such as nucleic acid (e.g., DNA, RNA) sequencing.

Detection/Quantitation of Molecules Using Luminance Lifetimes

An integrated circuit having an integrated photodetector according to aspects of the present application may be designed with suitable functions for a variety of detection and imaging applications. As described in further detail below, such an integrated photodetector can have the ability to detect light within one or more time intervals, or "time bins." To collect information regarding the time of arrival of the light, charge carriers are generated in response to incident photons and can be segregated into respective time bins based upon their time of arrival.

An integrated photodetector according to some aspects of the present application may be used for differentiating among light emission sources, including luminescent molecules, such as fluorophores. Luminescent molecules vary in the wavelength of light they emit, the temporal characteristics of the light they emit (e.g., their emission decay time periods), and their response to excitation energy. Accordingly, luminescent molecules may be identified or discriminated from other luminescent molecules based on detecting these properties. Such identification or discrimination techniques may be used alone or in any suitable combination.

In some embodiments, an integrated photodetector as described in the present application can measure or discriminate luminance lifetimes, such as fluorescence lifetimes. Fluorescence lifetime measurements are based on exciting one or more fluorescent molecules, and measuring the time variation in the emitted luminescence. The probability of a fluorescent molecule to emit a photon after the fluorescent molecule reaches an excited state decreases exponentially over time. The rate at which the probability decreases may be characteristic of a fluorescent molecule, and may be different for different fluorescent molecules. Detecting the temporal characteristics of light emitted by fluorescent molecules may allow identifying fluorescent molecules and/or discriminating fluorescent molecules with respect to one another. Luminescent molecules are also referred to herein as luminescent markers, or simply "markers."

After reaching an excited state, a marker may emit a photon with a certain probability at a given time. The probability of a photon being emitted from an excited marker may decrease over time after excitation of the marker. The decrease in the probability of a photon being emitted over time may be represented by an exponential decay function $p(t)=e^{-t/\tau}$, where p(t) is the probability of photon emission at a time, t, and τ is a temporal parameter of the marker. The temporal parameter τ indicates a time after excitation when the probability of the marker emitting a photon is a certain value. The temporal parameter, τ, is a property of a marker that may be distinct from its absorption and emission spectral properties. Such a temporal parameter, τ, is referred to as the luminance lifetime, the fluorescence lifetime or simply the "lifetime" of a marker.

FIG. 1A plots the probability of a photon being emitted as a function of time for two markers with different lifetimes. The marker represented by probability curve B has a probability of emission that decays more quickly than the probability of emission for the marker represented by probability curve A. The marker represented by probability curve B has a shorter temporal parameter, τ, or lifetime than the marker represented by probability curve A. Markers may have fluorescence lifetimes ranging from 0.1-20 ns, in some embodiments. However, the techniques described herein are not limited as to the lifetimes of the marker(s) used.

The lifetime of a marker may be used to distinguish among more than one marker, and/or may be used to identify marker(s). In some embodiments, fluorescence lifetime measurements may be performed in which a plurality of markers having different lifetimes are excited by an excitation source. As an example, four markers having lifetimes of 0.5, 1, 2, and 3 nanoseconds, respectively, may be excited by a light source that emits light having a selected wavelength (e.g., 635 nm, by way of example). The markers may be identified or differentiated from each other based on measuring the lifetime of the light emitted by the markers.

Fluorescence lifetime measurements may use relative intensity measurements by comparing how intensity changes over time, as opposed to absolute intensity values. As a result, fluorescence lifetime measurements may avoid some of the difficulties of absolute intensity measurements. Absolute intensity measurements may depend on the concentration of fluorophores present and calibration steps may be needed for varying fluorophore concentrations. By contrast, fluorescence lifetime measurements may be insensitive to the concentration of fluorophores.

Luminescent markers may be exogenous or endogenous. Exogenous markers may be external luminescent markers used as a reporter and/or tag for luminescent labeling. Examples of exogenous markers may include fluorescent molecules, fluorophores, fluorescent dyes, fluorescent stains, organic dyes, fluorescent proteins, enzymes, and/or quantum dots. Such exogenous markers may be conjugated to a probe or functional group (e.g., molecule, ion, and/or ligand) that specifically binds to a particular target or component. Attaching an exogenous tag or reporter to a probe allows identification of the target through detection of the presence of the exogenous tag or reporter. Examples of probes may include proteins, nucleic acids such as DNA molecules or RNA molecules, lipids and antibody probes. The combination of an exogenous marker and a functional group may form any suitable probes, tags, and/or labels used for detection, including molecular probes, labeled probes, hybridization probes, antibody probes, protein probes (e.g., biotin-binding probes), enzyme labels, fluorescent probes, fluorescent tags, and/or enzyme reporters.

While exogenous markers may be added to a sample or region, endogenous markers may be already part of the sample or region. Endogenous markers may include any luminescent marker present that may luminesce or "autofluoresce" in the presence of excitation energy. Autofluorescence of endogenous fluorophores may provide for label-free and noninvasive labeling without requiring the introduction of endogenous fluorophores. Examples of such endogenous fluorophores may include hemoglobin, oxyhemoglobin, lipids, collagen and elastin crosslinks, reduced nicotinamide adenine dinucleotide (NADH), oxidized flavins (FAD and FMN), lipofuscin, keratin, and/or prophyrins, by way of example and not limitation.

Differentiating between markers by lifetime measurements may allow for fewer wavelengths of excitation light to be used than when the markers are differentiated by measurements of emission spectra. In some embodiments, sensors, filters, and/or diffractive optics may be reduced in number or eliminated when using fewer wavelengths of excitation light and/or luminescent light. In some embodiments, labeling may be performed with markers that have different lifetimes, and the markers may be excited by light having the same excitation wavelength or spectrum. In some embodiments, an excitation light source may be used that emits light of a single wavelength or spectrum, which may reduce the cost. However, the techniques described herein are not limited in this respect, as any number of excitation light wavelengths or spectra may be used. In some embodiments, an integrated photodetector may be used to determine both spectral and temporal information regarding received light. In some embodiments a quantitative analysis of the types of molecule(s) present may be performed by determining a temporal parameter, a spectral parameter, or a combination of the temporal and spectral parameters of the emitted luminescence from a marker.

An integrated photodetector that detects the arrival time of incident photons may reduce additional optical filtering (e.g., optical spectral filtering) requirements. As described below, an integrated photodetector according to the present application may include a drain to remove photogenerated carriers at particular times. By removing photogenerated carriers in this manner, unwanted charge carriers produced in response to an excitation light pulse may be discarded without the need for optical filtering to prevent reception of light from the excitation pulse. Such a photodetector may reduce overall design integration complexity, optical and/or filtering components, and/or cost.

In some embodiments, a fluorescence lifetime may be determined by measuring the time profile of the emitted luminescence by aggregating collected charge carriers in one or more time bins of the integrated photodetector to detect luminance intensity values as a function of time. In some embodiments, the lifetime of a marker may be determined by performing multiple measurements where the marker is excited into an excited state and then the time when a photon emits is measured. For each measurement, the excitation source may generate a pulse of excitation light directed to the marker, and the time between the excitation pulse and subsequent photon event from the marker may be determined. Additionally or alternatively, when an excitation pulse occurs repeatedly and periodically, the time between when a photon emission event occurs and the subsequent excitation pulse may be measured, and the measured time may be subtracted from the time interval between excitation pulses (i.e., the period of the excitation pulse waveform) to determine the time of the photon absorption event.

By repeating such experiments with a plurality of excitation pulses, the number of instances a photon is emitted from the marker within a certain time interval after excitation may be determined, which is indicative of the probability of a photon being emitted within such a time interval after excitation. The number of photon emission events collected may be based on the number of excitation pulses emitted to the marker. The number of photon emission events over a measurement period may range from 50-10,000,000 or more, in some embodiments, however, the techniques described herein are not limited in this respect. The number of instances a photon is emitted from the marker within a certain time interval after excitation may populate a histogram representing the number of photon emission events that occur within a series of discrete time intervals or time bins. The number of time bins and/or the time interval of each bin may be set and/or adjusted to identify a particular lifetime and/or a particular marker. The number of time bins and/or the time interval of each bin may depend on the sensor used to detect the photons emitted. The number of time bins may be 1, 2, 3, 4, 5, 6, 7, 8, or more, such as 16, 32, 64, or more. A curve fitting algorithm may be used to fit a curve to the recorded histogram, resulting in a function representing the probability of a photon to be emitted after excitation of the marker at a given time. An exponential decay function, such as $p(t)=e^{-t/\tau}$ may be used to approximately fit the histogram data. From such a curve fitting, the temporal parameter or lifetime may be determined. The determined lifetime may be compared to known lifetimes of markers to identify the type of marker present.

Figure 1B:
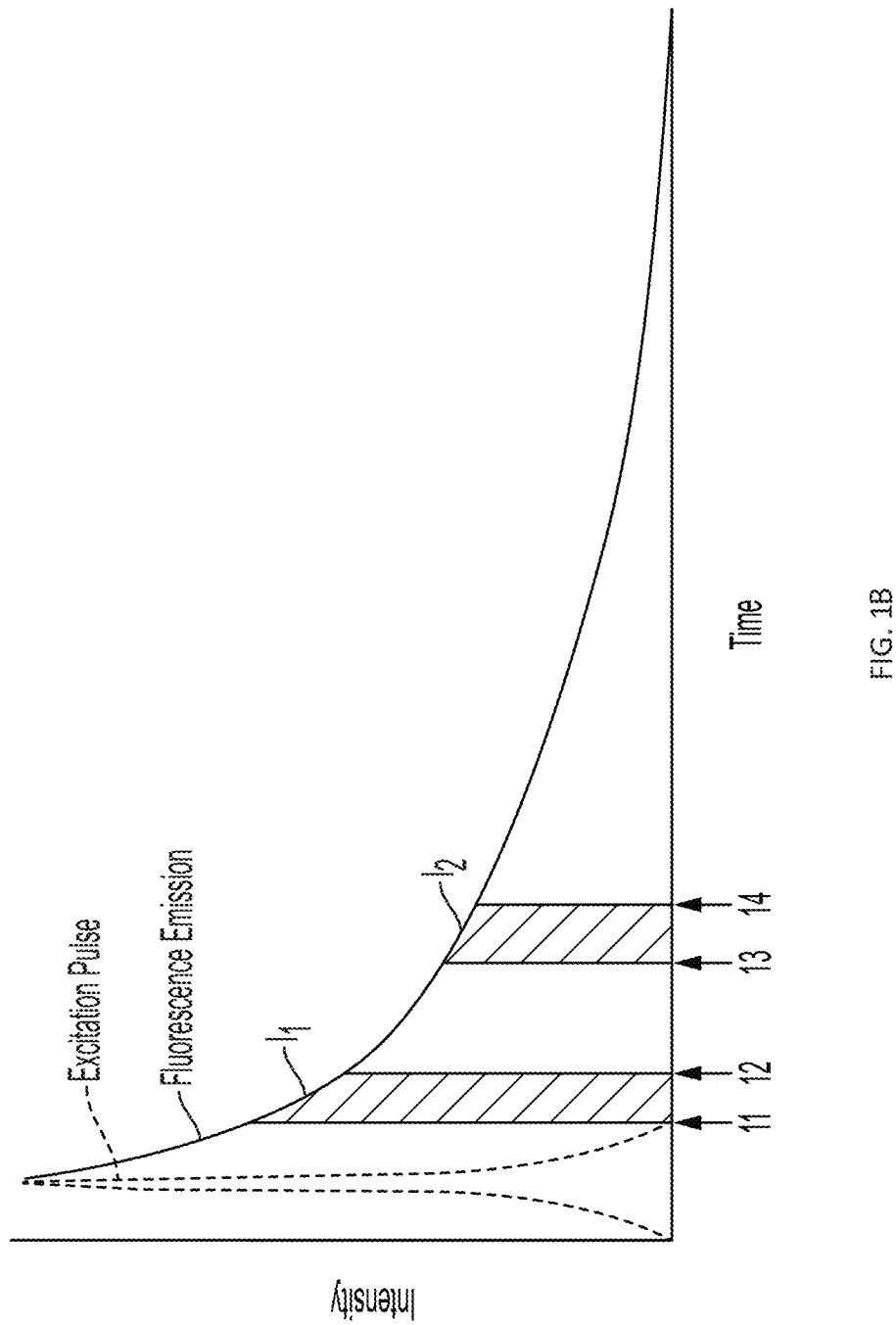
FIG. 1B shows example intensity profiles over time for an example excitation pulse (dotted line) and example fluorescence emission (solid line).

A lifetime may be calculated from the intensity values at two time intervals. FIG. 1B shows example intensity profiles over time for an example excitation pulse (dotted line) and example fluorescence emission (solid line). In the example shown in FIG. 1B, the photodetector measures the intensity over at least two time bins. The photons that emit luminescence energy between times t1 and t2 are measured by the photodetector as intensity I1 and luminescence energy emitted between times t3 and t4 are measured as I2. Any suitable number of intensity values may be obtained although only two are shown in FIG. 1B. Such intensity measurements may then be used to calculate a lifetime. When one fluorophore is present at a time, then the time binned luminescence signal may be fit to a single exponential decay. In some embodiments, only two time bins may be needed to accurately identify the lifetime for a fluorophore. When two or more fluorophores are present, then individual lifetimes may be identified from a combined luminescence signal by fitting the luminescence signal to multiple exponential decays, such as double or triple exponentials. In some embodiments two or more time bins may be needed in order to accurately identify more than one fluorescence lifetime from such a luminescence signal. However, in some instances with multiple fluorophores, an average fluorescence lifetime may be determined by fitting a single exponential decay to the luminescence signal.

In some instances, the probability of a photon emission event and thus the lifetime of a marker may change based on the surroundings and/or conditions of the marker. For example, the lifetime of a marker confined in a volume with a diameter less than the wavelength of the excitation light may be smaller than when the marker is not in the volume. Lifetime measurements with known markers under conditions similar to when the markers are used for labeling may be performed. The lifetimes determined from such measurements with known markers may be used when identifying a marker.

Sequencing Using Luminance Lifetime Measurements

Individual pixels of an integrated photodetector may be capable of fluorescence lifetime measurements used to identify fluorescent tags and/or reporters that label one or more targets, such as molecules or specific locations on molecules. Any one or more molecules of interest may be labeled with a fluorophore, including proteins, amino acids, enzymes, lipids, nucleotides, DNA, and RNA. When combined with detecting spectra of the emitted light or other labeling techniques, fluorescence lifetime may increase the total number of fluorescent tags and/or reporters that can be used. Identification based on lifetime may be used for single molecule analytical methods to provide information about characteristics of molecular interactions in complex mixtures where such information would be lost in ensemble averaging and may include protein-protein interactions, enzymatic activity, molecular dynamics, and/or diffusion on membranes. Additionally, fluorophores with different fluorescence lifetimes may be used to tag target components in various assay methods that are based on presence of a labeled component. In some embodiments, components may be separated, such as by using microfluidic systems, based on detecting particular lifetimes of fluorophores.

Measuring fluorescence lifetimes may be used in combination with other analytical methods. For an example, fluorescence lifetimes may be used in combination with fluorescence resonance energy transfer (FRET) techniques to discriminate between the states and/or environments of donor and acceptor fluorophores located on one or more molecules. Such measurements may be used to determine the distance between the donor and the acceptor. In some instances, energy transfer from the donor to the acceptor may decrease the lifetime of the donor. In another example, fluorescence lifetime measurements may be used in combination with DNA sequencing techniques where four fluorophores having different lifetimes may be used to label the four different nucleotides (A, T, G, C) in a DNA molecule with an unknown sequence of nucleotides. The fluorescence lifetimes, instead of emission spectra, of the fluorophores may be used to identify the sequence of nucleotides. By using fluorescence lifetime instead of emission spectra for certain techniques, accuracy and measurement resolution may increase because artifacts due to absolute intensity measurements are reduced. Additionally, lifetime measurements may reduce the complexity and/or expense of the system because fewer excitation energy wavelengths are required and/or fewer emission energy wavelengths need be detected.

The methods described herein may be used for sequencing of nucleic acids, such as DNA sequencing or RNA sequencing. DNA sequencing allows for the determination of the order and position of nucleotides in a target nucleic acid molecule. Technologies used for DNA sequencing vary greatly in the methods used to determine the nucleic acid sequence as well as in the rate, read length, and incidence of errors in the sequencing process. A number of DNA sequencing methods are based on sequencing by synthesis, in which the identity of a nucleotide is determined as the nucleotide is incorporated into a newly synthesized strand of nucleic acid that is complementary to the target nucleic acid. Many sequencing by synthesis methods require the presence of a population of target nucleic acid molecules (e.g., copies of a target nucleic acid) or a step of amplification of the target nucleic acid to achieve a population of target nucleic acids. Improved methods for determining the sequence of single nucleic acid molecules is desired.

There have been recent advances in sequencing single nucleic acid molecules with high accuracy and long read length. The target nucleic acid used in single molecule sequencing technology, for example the SMRT technology developed by Pacific Biosciences, is a single stranded DNA template that is added to a sample well containing at least one component of the sequencing reaction (e.g., the DNA polymerase) immobilized or attached to a solid support such as the bottom of the sample well. The sample well also contains deoxyribonucleoside triphosphates, also referred to a "dNTPs," including adenine, cytosine, guanine, and thymine dNTPs, that are conjugated to detection labels, such as fluorophores. Preferably each class of dNTPs (e.g. adenine dNTPs, cytosine dNTPs, guanine dNTPs, and thymine dNTPs) are each conjugated to a distinct detection label such that detection of the signal indicates the identity of the dNTP that was incorporated into the newly synthesized nucleic acid. The detection label may be conjugated to the dNTP at any position such that the presence of the detection label does not inhibit the incorporation of the dNTP into the newly synthesized nucleic acid strand or the activity of the polymerase. In some embodiments, the detection label is conjugated to the terminal phosphate (the gamma phosphate) of the dNTP.

Any polymerase may be used for single molecule DNA sequencing that is capable of synthesizing a nucleic acid complementary to a target nucleic acid. Examples of polymerases include $E.\ coli$ DNA polymerase I, T7 DNA polymerase, bacteriophage T4 DNA polymerase φ29 (psi29) DNA polymerase, and variants thereof. In some embodiments, the polymerase is a single subunit polymerase. Upon base pairing between a nucleobase of a target nucleic acid and the complementary dNTP, the polymerase incorporates the dNTP into the newly synthesized nucleic acid strand by forming a phosphodiester bond between the 3' hydroxyl end of the newly synthesized strand and the alpha phosphate of the dNTP. In examples in which the detection label conjugated to the dNTP is a fluorophore, its presence is signaled by excitation and a pulse of emission is detected during the step of incorporation. For detection labels that are conjugated to the terminal (gamma) phosphate of the dNTP, incorporation of the dNTP into the newly synthesized strand results in release the beta and gamma phosphates and the detection label, which is free to diffuse in the sample well, resulting in a decrease in emission detected from the fluorophore.

The techniques described herein are not limited as to the detection or quantitation of molecules or other samples, or to performing sequencing. In some embodiments, an integrated photodetector may perform imaging to obtain spatial information regarding a region, object or scene and temporal information regarding the arrival of incident photons using the region, object or scene. In some embodiments, the integrated photodetector may perform luminescence lifetime imaging of a region, object or sample, such as fluorescence lifetime imaging.

Additional Applications

Although the integrated photodetector described herein may be applied to the analysis of a plurality of biological and/or chemical samples, as discussed above, the integrated photodetector may be applied to other applications, such as imaging applications, for example.

In some embodiments, the integrated photodetector may include a pixel array that performs imaging of a region, object or scene, and may detect temporal characteristics of the light received at individual pixels from different regions of the region, object or scene. For example, in some embodiments the integrated photodetector may perform imaging of tissue based on the temporal characteristics of light received from the tissue, which may enable a physician performing a procedure (e.g., surgery) to identify an abnormal or diseased region of tissue (e.g., cancerous or pre-cancerous). In some embodiments, the integrated photodetector may be incorporated into a medical device, such as a surgical imaging tool. In some embodiments, time-domain information regarding the light emitted by tissue in response to a light excitation pulse may be obtained to image and/or characterize the tissue. For example, imaging and/or characterization of tissue or other objects may be performed using fluorescence lifetime imaging.

Although the integrated photodetector may be applied in a scientific or diagnostic context such as by performing imaging or analysis of biological and/or chemical samples, or imaging tissue, as described above, such an integrated photodetector may be used in any other suitable contexts. For example, in some embodiments, such an integrated photodetector may image a scene using temporal characteristics of the light detected in individual pixels. An example of an application for imaging a scene is range imaging or time-of-flight imaging, in which the amount of time light takes to reach the photodetector is analyzed to determine the distance traveled by the light to the photodetector. Such a technique may be used to perform three-dimensional imaging of a scene. For example, a scene may be illuminated with a light pulse emitted from a known location relative to the integrated photodetector, and the reflected light detected by the photodetector. The amount of time that the light takes to reach the integrated photodetector at respective pixels of the array is measured to determine the distance(s) light traveled from respective portions of the scene to reach respective pixels of the photodetector. In some embodiments, the integrated photodetector may be incorporated into a consumer electronic device such as a camera, cellular telephone, or tablet computer, for example, to enable such devices to capture and process images or video based on the range information obtained.

In some embodiments, the integrated photodetector described in the present application may be used to measure low light intensities. Such a photodetector may be suitable for applications that require photodetectors with a high sensitivity, such as applications that may currently use single photon counting techniques, for example. However, the techniques described herein are not limited in this respect, as the integrated photodetector described in the present applications may measure any suitable light intensities.

Additional Luminescence Lifetime Applications

Imaging and Characterization Using Lifetimes

As mentioned above, the techniques described herein are not limited to labeling, detection and quantitation using exogenous fluorophores. In some embodiments, a region, object or sample may be imaged and/or characterized using fluorescence lifetime imaging techniques though use of an integrated photodetector. In such techniques, the fluorescence characteristics of the region, object or sample itself may be used for imaging and/or characterization. Either exogenous markers or endogenous markers may be detected through lifetime imaging and/or characterization. Exogenous markers attached to a probe may be provided to the region, object, or sample in order to detect the presence and/or location of a particular target component. The exogenous marker may serve as a tag and/or reporter as part of a labeled probe to detect portions of the region, object, or sample that contains a target for the labeled probe. Autofluorescence of endogenous markers may provide a label-free and noninvasive contrast for spatial resolution that can be readily utilized for imaging without requiring the introduction of endogenous markers. For example, autofluorescence signals from biological tissue may depend on and be indicative of the biochemical and structural composition of the tissue.

Fluorescence lifetime measurements may provide a quantitative measure of the conditions surrounding the fluorophore. The quantitative measure of the conditions may be in addition to detection or contrast. The fluorescence lifetime for a fluorophore may depend on the surrounding environment for the fluorophore, such as pH or temperature, and a change in the value of the fluorescence lifetime may indicate a change in the environment surrounding the fluorophore. As an example, fluorescence lifetime imaging may map changes in local environments of a sample, such as in biological tissue (e.g., a tissue section or surgical resection). Fluorescence lifetime measurements of autofluorescence of endogenous fluorophores may be used to detect physical and metabolic changes in the tissue. As examples, changes in tissue architecture, morphology, oxygenation, pH, vascularity, cell structure and/or cell metabolic state may be detected by measuring autofluorescence from the sample and determining a lifetime from the measured autofluorescence. Such methods may be used in clinical applications, such as screening, image-guided biopsies or surgeries, and/or endoscopy. In some embodiments, an integrated photodetector of the present application may be incorporated into a clinical tool, such as a surgical instrument, for example, to perform fluorescence lifetime imaging. Determining fluorescence lifetimes based on measured autofluorescence provides clinical value as a label-free imaging method that allows a clinician to quickly screen tissue and detect small cancers and/or pre-cancerous lesions that are not apparent to the naked eye. Fluorescence lifetime imaging may be used for detection and delineation of malignant cells or tissue, such as tumors or cancer cells which emit luminescence having a longer fluorescence lifetime than healthy tissue. For example, fluorescence lifetime imaging may be used for detecting cancers on optically accessible tissue, such as gastrointestinal tract, bladder, skin, or tissue surface exposed during surgery.

In some embodiments, fluorescence lifetimes may be used for microscopy techniques to provide contrast between different types or states of samples. Fluorescence lifetime imaging microscopy (FLIM) may be performed by exciting a sample with a light pulse, detecting the fluorescence signal as it decays to determine a lifetime, and mapping the decay time in the resulting image. In such microscopy images, the pixel values in the image may be based on the fluorescence lifetime determined for each pixel in the photodetector collecting the field of view.

Imaging a Scene or Object Using Temporal Information

As discussed above, an integrated photodetector as described in the present application may be used in scientific and clinical contexts in which the timing of light emitted may be used to detect, quantify, and or image a region, object or sample. However, the techniques described herein are not limited to scientific and clinical applications, as the integrated photodetector may be used in any imaging application that may take advantage of temporal information regarding the time of arrival of incident photons. An example of an application is time-of-flight imaging.

Time-of-Flight Applications

In some embodiments, an integrated photodetector may be used in imaging techniques that are based on measuring a time profile of scattered or reflected light, including time-of-flight measurements. In such time-of-flight measurements, a light pulse may be is emitted into a region or sample and scattered light may be detected by the integrated photodetector. The scattered or reflected light may have a distinct time profile that may indicate characteristics of the region or sample. Backscattered light by the sample may be detected and resolved by their time of flight in the sample. Such a time profile may be a temporal point spread function (TPSF). The time profile may be acquired by measuring the integrated intensity over multiple time bins after the light pulse is emitted. Repetitions of light pulses and accumulating the scattered light may be performed at a certain rate to ensure that all the previous TPSF is completely extinguished before generating a subsequent light pulse. Time-resolved diffuse optical imaging methods may include spectroscopic diffuse optical tomography where the light pulse may be infrared light in order to image at a further depth in the sample. Such time-resolved diffuse optical imaging methods may be used to detect tumors in an organism or in part of an organism, such as a person's head.

Additionally or alternatively, time-of-flight measurements may be used to measure distance or a distance range based on the speed of light and time between an emitted light pulse and detecting light reflected from an object. Such time-of-flight techniques may be used in a variety of applications including cameras, proximity detection sensors in automobiles, human-machine interfaces, robotics and other applications that may use three-dimensional information collected by such techniques.

Integrated Photodetector for Time Binning Photogenerated Charge Carriers

Some embodiments relate to an integrated circuit having a photodetector that produces charge carriers in response to incident photons and which is capable of discriminating the timing at which the charge carriers are generated by the arrival of incident photons with respect to a reference time (e.g., a trigger event). In some embodiments, a charge carrier segregation structure segregates charge carriers generated at different times and directs the charge carriers into one or more charge carrier storage regions (termed "bins") that aggregate charge carriers produced within different time periods. Each bin stores charge carriers produced within a selected time interval. Reading out the charge stored in each bin can provide information about the number of photons that arrived within each time interval. Such an integrated circuit can be used in any of a variety of applications, such as those described herein.

An example of an integrated circuit having a photodetection region and a charge carrier segregation structure will be described. In some embodiments, the integrated circuit may include an array of pixels, and each pixel may include one or more photodetection regions and one or more charge carrier segregation structures, as discussed below.

Overview of Pixel Structure and Operation

Figure 2A:
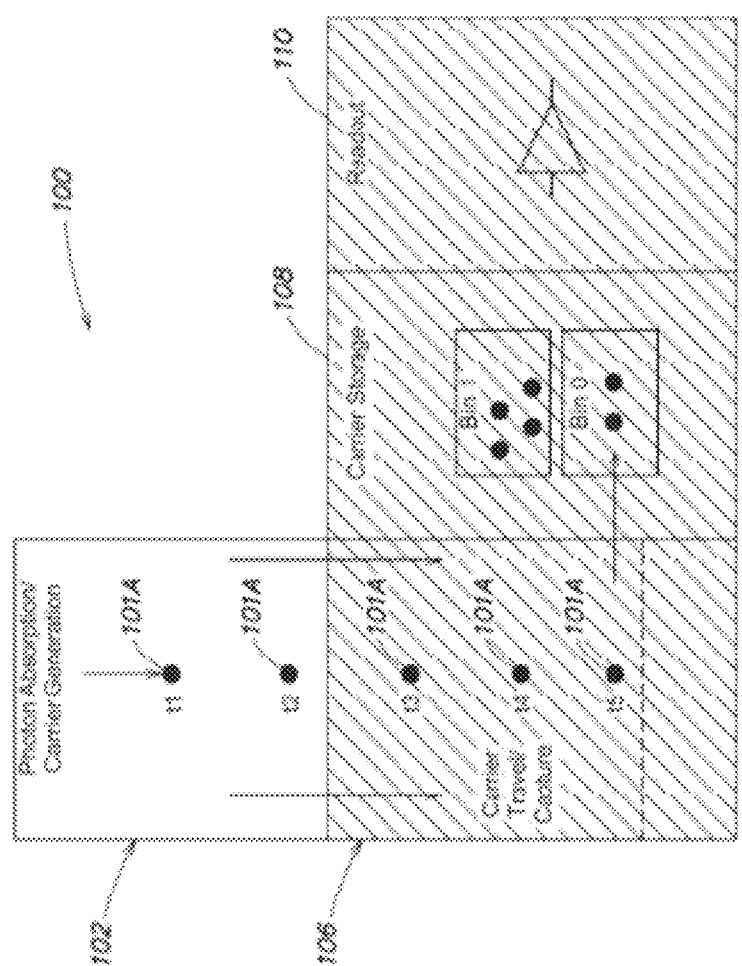
FIG. 2A shows a diagram of a pixel of an integrated photodetector.

FIG. 2A shows a diagram of a pixel 100, according to some embodiments. Pixel 100 includes a photon absorption/carrier generation region 102 (also referred to as a photodetection region), a carrier travel/capture region 106, a carrier storage region 108 having one or more charge carrier storage regions, also referred to herein as "charge carrier storage bins" or simply "bins," and readout circuitry 110 for reading out signals from the charge carrier storage bins.

The photon absorption/carrier generation region 102 may be a region of semiconductor material (e.g., silicon) that can convert incident photons into photogenerated charge carriers. The photon absorption/carrier generation region 102 may be exposed to light, and may receive incident photons. When a photon is absorbed by the photon absorption/carrier generation region 102 it may generate photogenerated charge carriers, such as an electron/hole pair. Photogenerated charge carriers are also referred to herein simply as "charge carriers."

An electric field may be established in the photon absorption/carrier generation region 102. In some embodiments, the electric field may be "static," as distinguished from the changing electric field in the carrier travel/capture region 106. The electric field in the photon absorption/carrier generation region 102 may include a lateral component, a vertical component, or both a lateral and a vertical component. The lateral component of the electric field may be in the downward direction of FIG. 2A, as indicated by the arrows, which induces a force on photogenerated charge carriers that drives them toward the carrier travel/capture region 106. The electric field may be formed in a variety of ways.

In some embodiments one or more electrodes may be formed over the photon absorption/carrier generation region 102. The electrodes(s) may have voltages applied thereto to establish an electric field in the photon absorption/carrier generation region 102. Such electrode(s) may be termed "photogate(s)." In some embodiments, photon absorption/carrier generation region 102 may be a region of silicon that is fully depleted of charge carriers.

In some embodiments, the electric field in the photon absorption/carrier generation region 102 may be established by a junction, such as a PN junction. The semiconductor material of the photon absorption/carrier generation region 102 may be doped to form the PN junction with an orientation and/or shape that produces an electric field that induces a force on photogenerated charge carriers that drives them toward the carrier travel/capture region 106. Producing the electric field using a junction may improve the quantum efficiency with respect to use of electrodes overlying the photon absorption/carrier generation region 102 which may prevent a portion of incident photons from reaching the photon absorption/carrier generation region 102. Using a junction may reduce dark current with respect to use of photogates. It has been appreciated that dark current may be generated by imperfections at the surface of the semiconductor substrate that may produce carriers. In some embodiments, the P terminal of the PN junction diode may connected to a terminal that sets its voltage. Such a diode may be referred to as a "pinned" photodiode. A pinned photodiode may promote carrier recombination at the surface, due to the terminal that sets its voltage and attracts carriers, which can reduce dark current. Photogenerated charge carriers that are desired to be captured may pass underneath the recombination area at the surface. In some embodiments, the lateral electric field may be established using a graded doping concentration in the semiconductor material.

In some embodiments, an absorption/carrier generation region 102 that has a junction to produce an electric field may have one or more of the following characteristics:

1) a depleted n-type region that is tapered away from the time varying field, 2) a p-type implant surrounding the n-type region with a gap to transition the electric field laterally into the n-type region, and/or 3) a p-type surface implant that buries the n-type region and serves as a recombination region for parasitic electrons.

In some embodiments, the electric field may be established in the photon absorption/carrier generation region 102 by a combination of a junction and at least one electrode. For example, a junction and a single electrode, or two or more electrodes, may be used. In some embodiments, one or more electrodes may be positioned near carrier travel/capture region 106 to establish the potential gradient near carrier travel/capture region 106, which may be positioned relatively far from the junction.

As illustrated in FIG. 2A, a photon may be captured and a charge carrier 101A (e.g., an electron) may be produced at time t1. In some embodiments, an electrical potential gradient may be established along the photon absorption/carrier generation region 102 and the carrier travel/capture region 106 that causes the charge carrier 101A to travel in the downward direction of FIG. 2A (as illustrated by the arrows shown in FIG. 2A). In response to the potential gradient, the charge carrier 101A may move from its position at time t1 to a second position at time t2, a third position at time t3, a fourth position at time t4, and a fifth position at time t5. The charge carrier 101A thus moves into the carrier travel/capture region 106 in response to the potential gradient.

The carrier travel/capture region 106 may be a semiconductor region. In some embodiments, the carrier travel/capture region 106 may be a semiconductor region of the same material as photon absorption/carrier generation region 102 (e.g., silicon) with the exception that carrier travel/capture region 106 may be shielded from incident light (e.g., by an overlying opaque material, such as a metal layer).

In some embodiments, and as discussed further below, a potential gradient may be established in the photon absorption/carrier generation region 102 and the carrier travel/capture region 106 by electrodes positioned above these regions. However, the techniques described herein are not limited as to particular positions of electrodes used for producing an electric potential gradient. Nor are the techniques described herein limited to establishing an electric potential gradient using electrodes. In some embodiments, an electric potential gradient may be established using a spatially graded doping profile and/or a PN junction. Any suitable technique may be used for establishing an electric potential gradient that causes charge carriers to travel along the photon absorption/carrier generation region 102 and carrier travel/capture region 106.

A charge carrier segregation structure may be formed in the pixel to enable segregating charge carriers produced at different times. In some embodiments, at least a portion of the charge carrier segregation structure may be formed over the carrier travel/capture region 106. The charge carrier segregation structure may include one or more electrodes formed over the carrier travel/capture region 106, the voltage of which may be controlled by control circuitry to change the electric potential in the carrier travel/capture region 106.

The electric potential in the carrier travel/capture region 106 may be changed to enable capturing a charge carrier. The potential gradient may be changed by changing the voltage on one or more electrodes overlying the carrier travel/capture region 106 to produce a potential barrier that can confine a carrier within a predetermined spatial region. For example, the voltage on an electrode overlying the dashed line in the carrier travel/capture region 106 of FIG. 2A may be changed at time t5 to raise a potential barrier along the dashed line in the carrier travel/capture region 106 of FIG. 2A, thereby capturing charge carrier 101A. As shown in FIG. 2A, the carrier captured at time t5 may be transferred to a bin "bin0" of carrier storage region 108. The transfer of the carrier to the charge carrier storage bin may be performed by changing the potential in the carrier travel/capture region 106 and/or carrier storage region 108 (e.g., by changing the voltage of electrode(s) overlying these regions) to cause the carrier to travel into the charge carrier storage bin.

Changing the potential at a certain point in time within a predetermined spatial region of the carrier travel/capture region 106 may enable trapping a carrier that was generated by photon absorption that occurred within a specific time interval. By trapping photogenerated charge carriers at different times and/or locations, the times at which the charge carriers were generated by photon absorption may be discriminated. In this sense, a charge carrier may be "time binned" by trapping the charge carrier at a certain point in time and/or space after the occurrence of a trigger event. The time binning of a charge carrier within a particular bin provides information about the time at which the photogenerated charge carrier was generated by absorption of an incident photon, and thus likewise "time bins," with respect to the trigger event, the arrival of the incident photon that produced the photogenerated charge carrier.

Figure 2B:
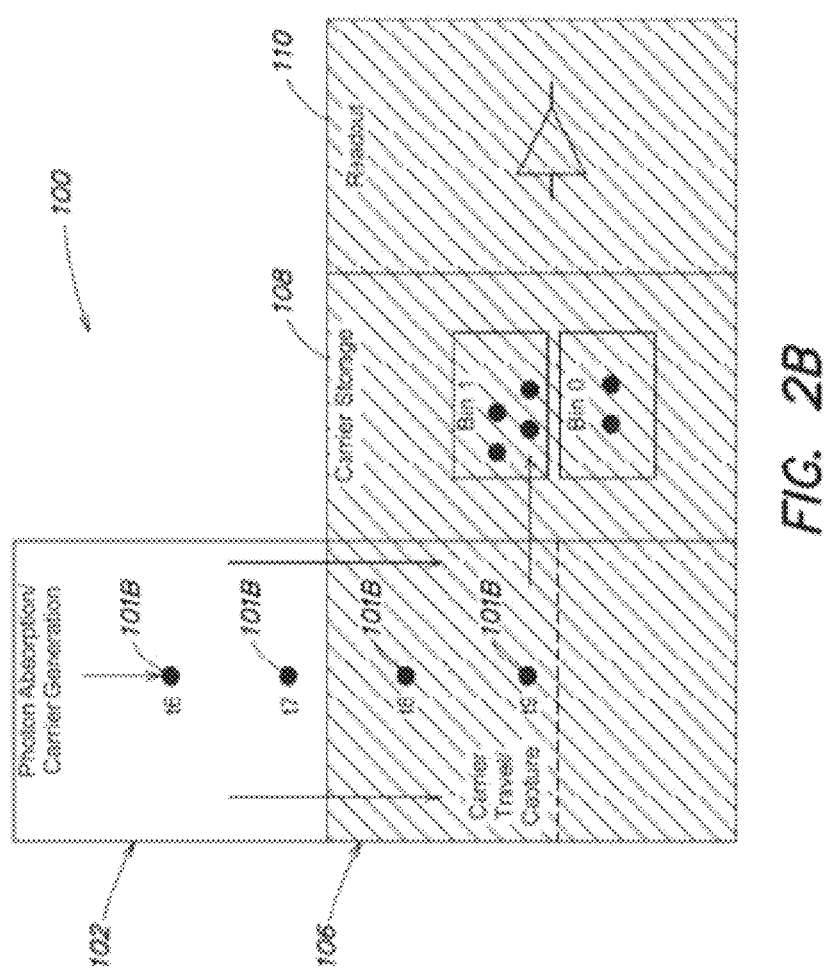
FIG. 2B illustrates capturing a charge carrier at a different point in time and space than in FIG. 2A.

FIG. 2B illustrates capturing a charge carrier at a different point in time and space. As shown in FIG. 2B, the voltage on an electrode overlying the dashed line in the carrier travel/capture region 106 may be changed at time t9 to raise a potential barrier along the dashed line in the carrier travel/capture region 106 of FIG. 2B, thereby capturing carrier 101B. As shown in FIG. 2B, the carrier captured at time t9 may be transferred to a bin "bin1" of carrier storage region 108. Since charge carrier 101B is trapped at time t9, it represents a photon absorption event that occurred at a different time (i.e., time t6) than the photon absorption event (i.e., at t1) for carrier 101A, which is captured at time t5.

Direct Binning Pixel

Figure 3:
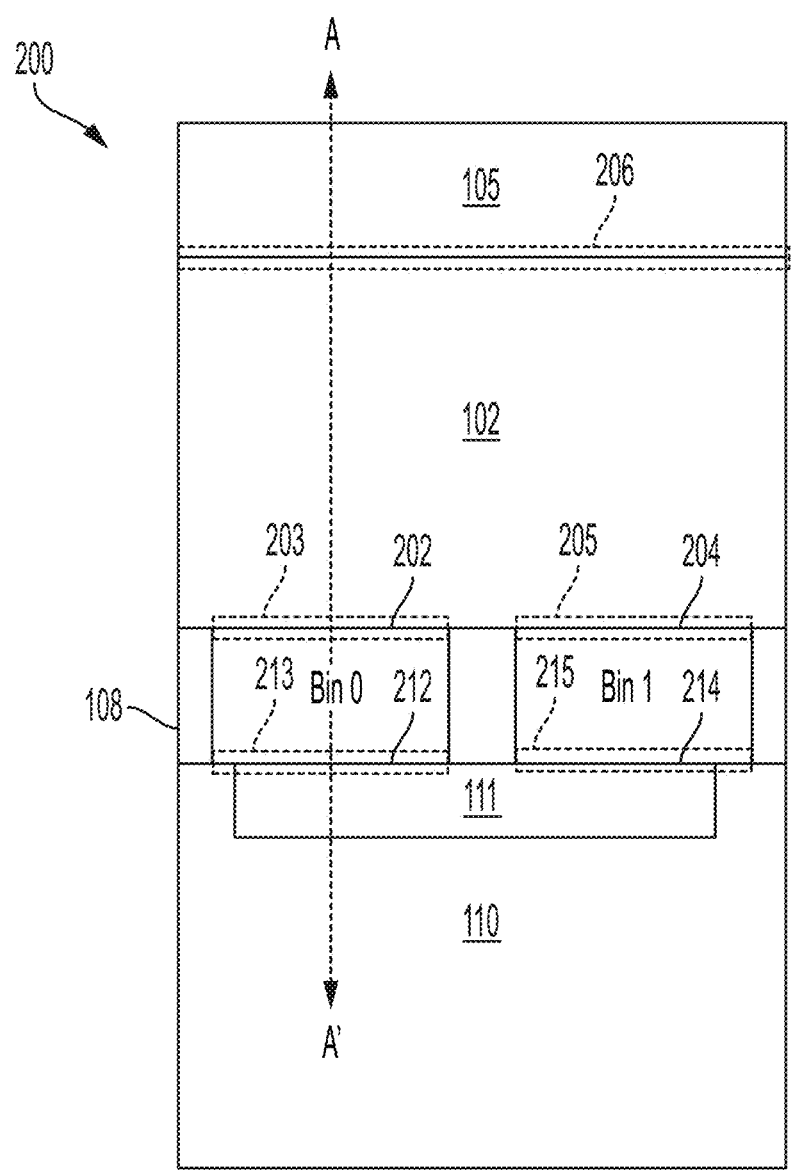
FIG. 3 shows an example of a direct binning pixel.

FIG. 3 shows an example of a pixel 200 in which charge carriers generated in the photon absorption/carrier generation region 102 may be directly transferred to a charge storage bin in charge carrier storage region 108. Such a pixel is termed a "direct binning pixel." As shown in FIG. 3, pixel 200 does not include a carrier travel/capture region 106. Rather than capturing carriers in carrier travel/capture region 106, charge carriers may be directly transferred from photon absorption/carrier generation region 102 into a bin of charge carrier storage region 108. The bin to which a charge carrier is transferred is based on the time of arrival of a photon in photon absorption/carrier generation region 102 that produces the charge carrier. The area of a direct binning pixel may be reduced at least in part due to omission of carrier travel/capture region 106. Advantageously, in some embodiments, a direct binning pixel may take up a smaller area on of a semiconductor chip, which may enable forming many pixels on the chip, such as thousands or millions of pixels, or more. Providing a large number of pixels on a chip may enable performing a large number of measurements in parallel, or performing imaging with high spatial resolution. Alternatively or additionally, a direct binning pixel may have reduced power consumption. Since charging and discharging each electrode of the pixel may consume power, pixel 200 may have reduced power consumption due to the presence of fewer electrodes, i.e., the electrodes for capturing charge carriers in carrier travel/capture region 106 can be omitted.

FIG. 3 shows an example of a pixel 200 having two bins in charge carrier storage region 108: bin 0 and bin 1. As discussed above, bin 0 may aggregate charge carriers received in one period following a trigger event, and bin 1 may aggregate charge carriers received in a later time period with respect to a trigger event. However, charge storage region 108 may have any number of bins, such as one bin, three bins, four bins, or more.

Figure 8:
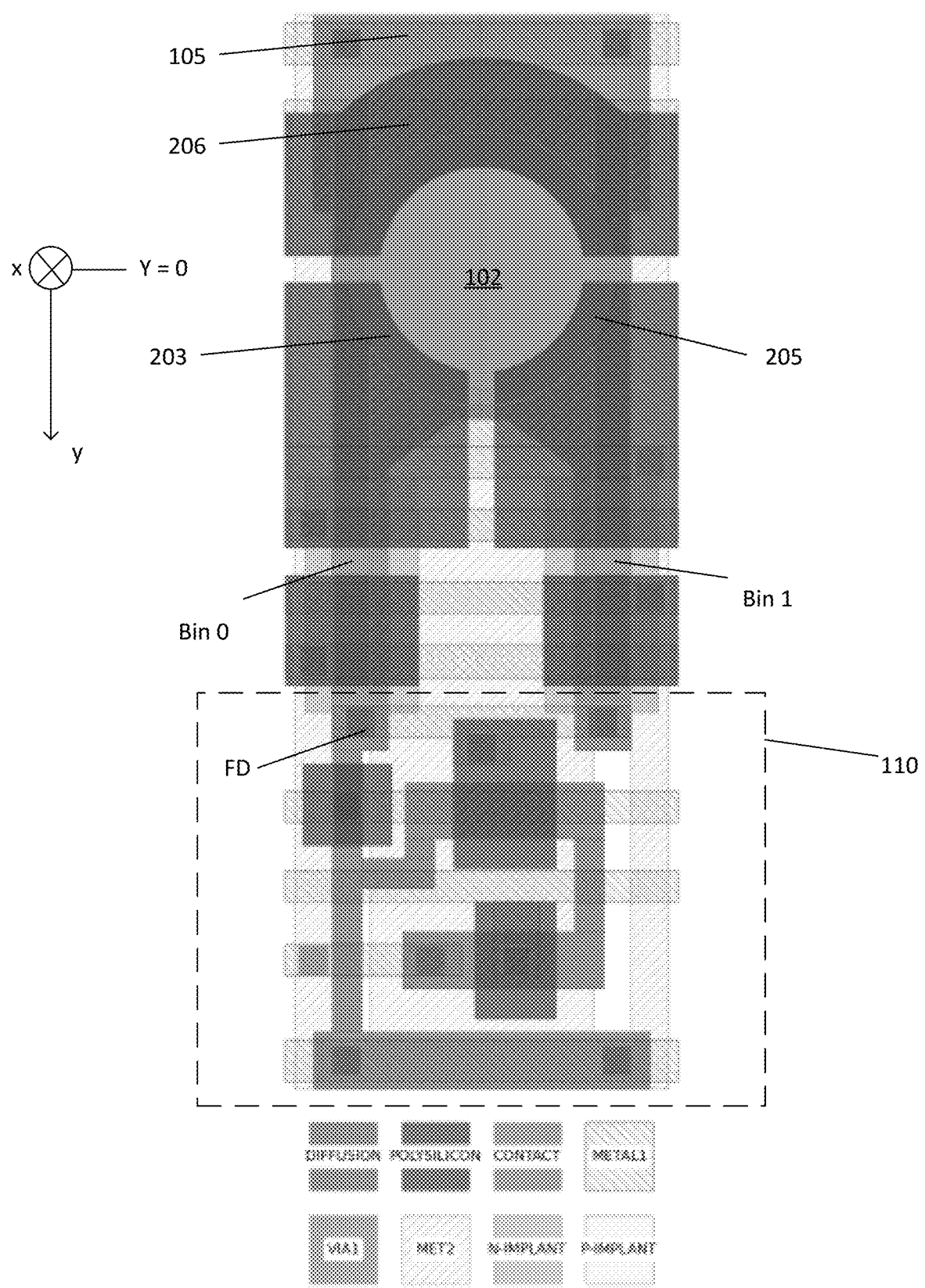
FIG. 8 shows a plan view of an example of a direct binning pixel.

The photon absorption/carrier generation region 102 may include a semiconductor region, which may be formed of any suitable semiconductor, such as silicon, for example. In some embodiments, the photon absorption/carrier generation region 102 may include a photodiode, such as a pinned photodiode. The photodiode may be fully depleted. In some embodiments, the photodiode may remain essentially depleted of electrons at all times. In some embodiments, the photodiode is configured to collect single photons. In such embodiments, a single photoelectron may be generated and confined in the photodiode. If formed by a CMOS process, the photodiode may be fully depleted by potentials available within devices produced by a CMOS process. Electrodes 203, 205 and 206 may be coupled to the diode at least partially surrounding the perimeter of the diode, as shown in more detail in FIG. 8. However, it should be noted that this the embodiment depicted in FIG. 8 is merely one example of a geometry suitable for electrodes 203, 205 and 206. The electrodes 203 and 205 may allow rapid charge transfer of confined carriers. Prior to discussing transfer of charge carriers to the bins, the rejection of unwanted carriers by transfer of the unwanted carriers into a rejection region 105 will be described.

Referring again to FIG. 3, direct binning pixel 200 may include a rejection region 105 to drain or otherwise discard charge carriers produced in photon absorption/carrier generation region 102 during a rejection period. A rejection period may be timed to occur during a trigger event, such as an excitation light pulse. Since an excitation light pulse may produce a number of unwanted charge carriers in photon absorption/carrier generation region 102, a potential gradient may be established in pixel 200 to drain such charge carriers to rejection region 105 during a rejection period. As an example, rejection region 105 may include a high potential diffusion area where electrons are drained to a supply voltage. Rejection region 105 may include an electrode 206 that charge couples region 102 directly to rejection region 105. In some embodiments, the electrode 206 may overlie the semiconductor region. The voltage of the electrode 206 may be varied to establish a desired potential gradient in photon absorption/carrier generation region 102. During a rejection period, the voltage of the electrode 206 may be set to a level that draws carriers from the photon absorption/carrier generation region 102 into the electrode 206, and out to the supply voltage. For example, the voltage of the electrode 206 may be set to a positive voltage to attract electrons, such that they are drawn away from the photon absorption/carrier generation region 102 to rejection region 105. During a rejection period, electrodes 203 and 205 may be set to a potential that forms potential barriers 202 and 204 to prevent the unwanted charge carriers from reaching the bins. Rejection region 105 may be considered a "lateral rejection region" because it allows transferring carriers laterally from region 102 to a drain. In some embodiments the rejection is in the opposite direction from the photodetection region with respect to the storage bins.

Following the rejection period, a photogenerated charge carrier produced in photon absorption/carrier generation region 102 may be time-binned. Individual charge carriers may be directed to a bin based on their time of arrival. To do so, the electrical potential between photon absorption/carrier generation region 102 and charge carrier storage region 108 may be changed in respective time periods to establish a potential gradient that causes the photogenerated charge carriers to be directed to respective time bins. For example, during a first time period a potential barrier 202 formed by electrode 203 may be lowered, and a potential gradient may be established from photon absorption/carrier generation region 102 to bin 0, such that a carrier generated during this period is transferred to bin 0. Then, during a second time period, a potential barrier 204 formed by electrode 205 may be lowered, and a potential gradient may be established from photon absorption/carrier generation region 102 to bin 1, such that a carrier generated during this later period is transferred to bin 1.

Figure 4:
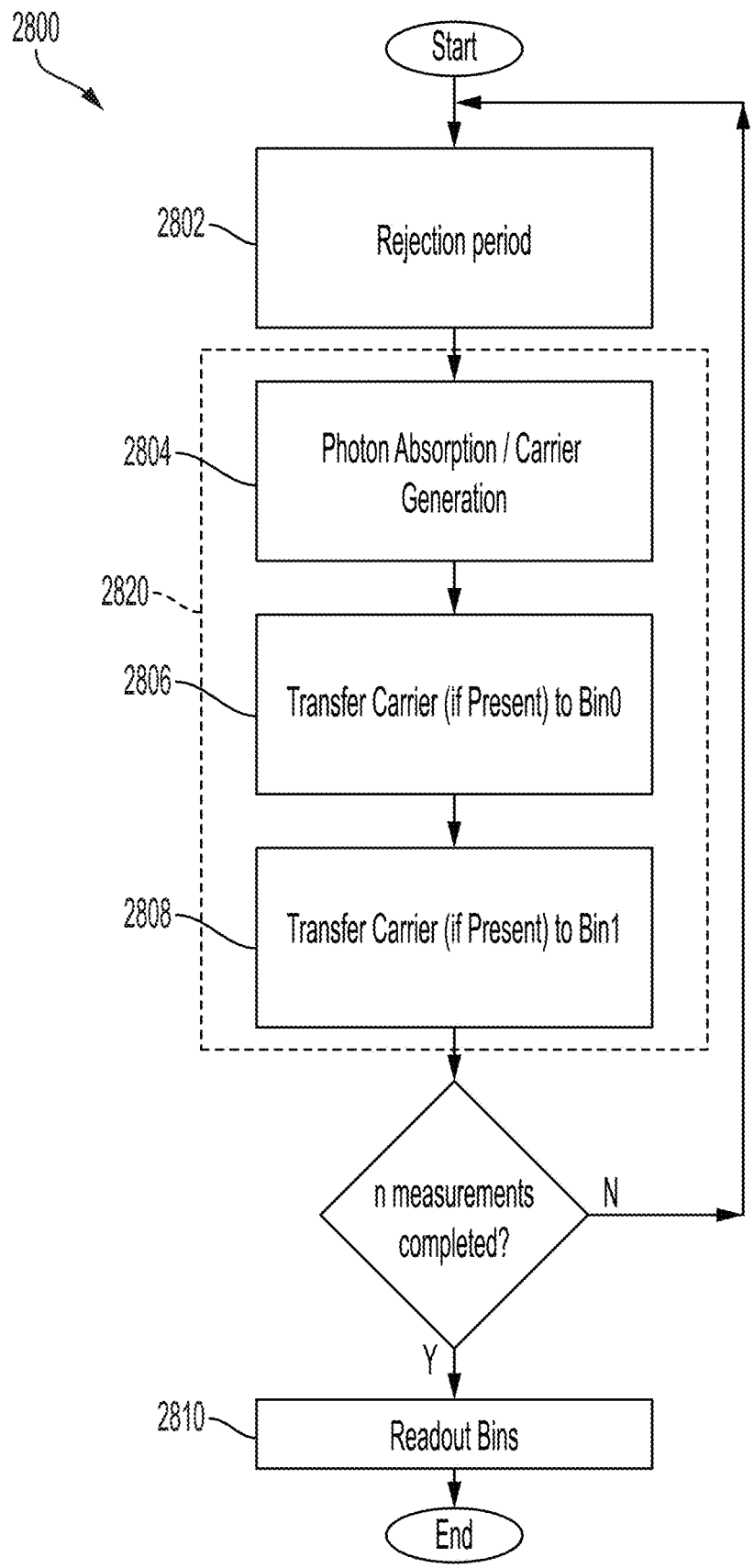
FIG. 4 shows a flowchart of a method of operating a direct binning pixel.

FIG. 4 shows a flowchart of a method 2800 of operating pixel 200 that includes performing a plurality of measurements 2820, according to some embodiments. In some embodiments, a "measurement" may include receiving a photon and transferring the captured carrier to a charge storage node corresponding to a particular time period or bin. A measurement may be repeated a plurality of times to gather statistical information about the times at which photons arrive at the photodetector. Such a method may be performed at least partially by an integrated device as described herein.

Step 2802 may be timed to occur during a trigger event. A trigger event may be an event that serves as a time reference for time binning arrival of a photon. The trigger event may be an optical pulse or an electrical pulse, for example, and could be a singular event or a repeating, periodic event. In the context of fluorescence lifetime detection, the trigger event may be the generation of a light excitation pulse to excite a fluorophore. In the context of time-of-flight imaging, the trigger event may be a pulse of light (e.g., from a flash) emitted by an imaging device comprising the integrated photodetector. The trigger event can be any event used as a reference for timing the arrival of photons or carriers.

The generation of the light excitation pulse may produce a significant number of photons, some of which may reach the pixel 200 and may produce charge carriers in the photon absorption/carrier generation area 102. Since photogenerated carriers from the light excitation pulse are not desired to be measured, they may be rejected by directing them to a drain. This can reduce the amount of unwanted signal that otherwise may need to be prevented from arriving by complex optical components, such as a shutter or filter, which may add additional design complexity and/or cost.

Figure 5A:
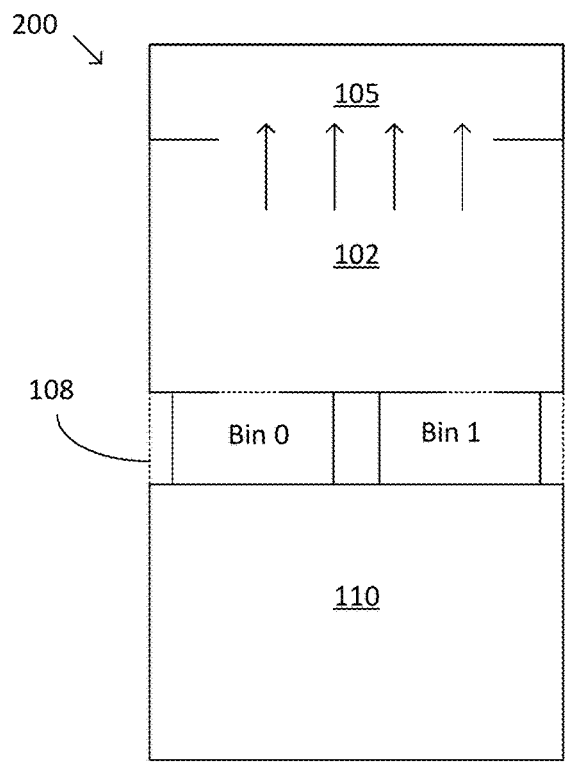
FIG. 5A-F show the direct binning pixel at various stages of the method of FIG. 4.

Step 2802 corresponds to a rejection period. The operation of pixel 200 during step 2802 is illustrated in FIG. 5A. In step 2802, the pixel 200 is operated to reject charge carriers produced in region 102 by transferring them to rejection region 105. For example, step 2802 may include controlling electrode 206 to produce a potential gradient that drives charge carriers produced in region 102 to rejection region 105. Carriers are rejected by directing them in the upward direction of FIG. 5A.

In step 2804, photon absorption and carrier generation may be performed in region 102. As discussed above, in some applications the probability of receiving a photon and generating a carrier in response to a trigger event may be low (e.g., about 1 in 10,000). Accordingly, step 2804 may not be performed for each trigger event, as often no photons may be received in response to a trigger event. However, in some embodiments, the quantity of photons received may be higher.

Figure 5B:
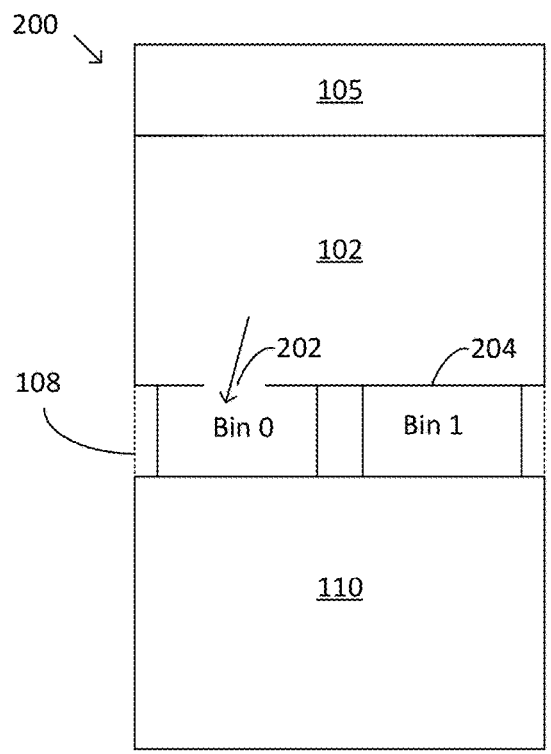
Figure 5C:
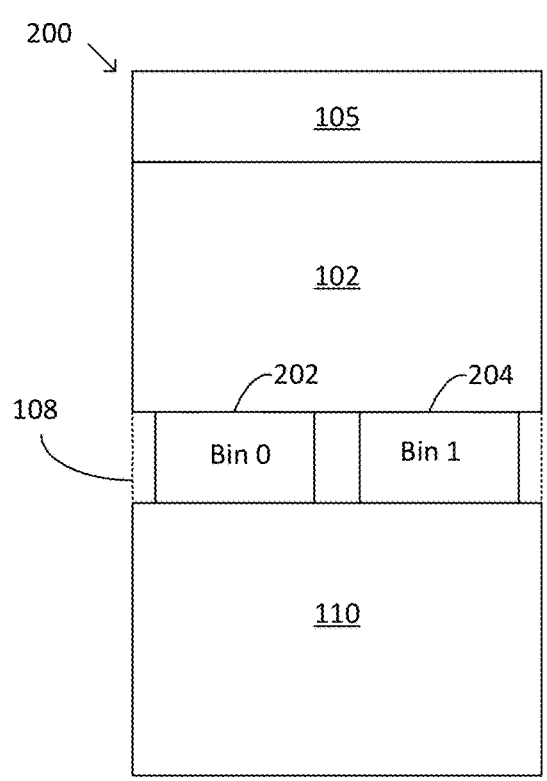

During step 2804, a potential barrier exists between photodetection region 102 and rejection region 105 to prevent photogenerated charge carriers from being rejected. During step 2804, a potential barrier 202 to bin 0 may be lowered, as shown in FIG. 5B, or may be raised, as shown in FIG. 5C. If the potential barrier 202 to bin 0 is lowered, a charge carrier may pass directly to bin 0 (step 2806). If the potential barrier 202 to bin 0 is raised, a charge carrier may be confined in region 102 until step 2806.

In step 2806, a carrier (if present) is transferred to bin 0. The potential barrier 202 to bin 0 is lowered or remains lowered. If a photogenerated charge carrier is produced in the time period following step 2802, the lowering of the potential barrier 202 allows the charge carrier to be transferred to bin 0. The potential barrier 202 may be raised or lowered by controlling the voltage of an electrode 203 at the boundary between region 102 and bin 0 (FIG. 3, FIG. 5B). Such an electrode may be positioned over the semiconductor region that controls the potential in the semiconductor region. In some embodiments, only a single electrode 203 may be disposed at the boundary between region 102 and bin 0 to control the potential barrier 202 that allows or prevents transfer of a charge carrier to bin 0. However, in some embodiments, the potential barrier 202 may be produced by more than one electrode. Unlike charge carrier capture region 106 of FIG. 2A, the electrode(s) 206 that produce potential barrier 202 may not trap a charge carrier at a location outside of a bin. Rather, the electrode(s) 206 may control a potential barrier 202 to either allow or prevent a charge carrier from entering bin 0. Also, unlike charge carrier capture region 106, which produces a number of potential barriers between region 102 and a bin, the potential barrier 202 may be a single potential barrier between region 102 and bin 0. The same or similar characteristics as described in this paragraph may be present in bin 1, potential barrier 204 and the electrode(s) 205 that produce potential barrier 204.

In some embodiments, after the rejection period a potential gradient may be formed that only allows charge to flow in one direction, that is, in the direction from region 102 to a time bin. Charge flows to one of the bins in the downward direction of FIGS. 5A-D. A suitable potential gradient may be established in the semiconductor region to cause generated carriers to travel through the semiconductor region in the downward direction of the figures toward carrier storage region 108. Such a potential gradient may be established in any suitable way, such as using a graded doping concentration and/or one or more electrodes at selected potentials. Accordingly, a photogenerated charge carrier produced in region 102 after step 2802 is transferred to bin 0, thus time binning the arrival of the photogenerated charge carrier in bin 0.

Following step 2806, the potential barrier 202 to bin 0 is raised, as illustrated in FIG. 5C. Optionally, both the potential barrier 202 to bin 0 and the potential barrier 204 to bin 1 may be raised for a period of time. If both barrier 202 and barrier 204 are raised, a charge carrier produced following step 2806 may be confined in region 102 until step 2808.

Figure 5D:
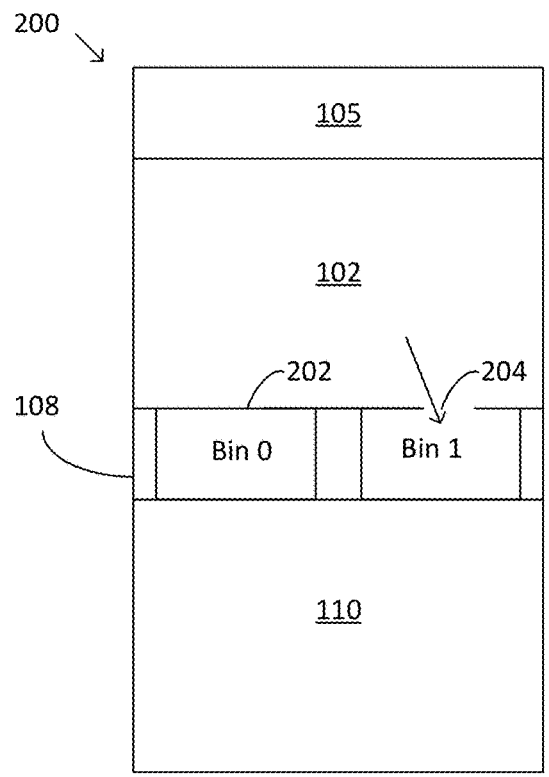

In step 2808, a carrier (if present) is transferred to bin 1, as illustrated in FIG. 5D. The potential barrier 204 to bin 1 is lowered. If a photogenerated charge carrier is produced in the time period following step 2806, the lowering of the potential barrier 204 allows the charge carrier to be transferred to bin 1. The potential barrier 204 may be raised or lowered by controlling the voltage of an electrode 205 at the boundary between region 102 and bin 1. Such an electrode may be positioned over the semiconductor region. Accordingly, a photogenerated charge carrier produced in region 102 after step 2806 is transferred to bin 1, thus time binning the arrival of the photogenerated charge carrier in bin 1. Following step 2808, the potential barrier 202 may be raised.

Following step 2808 the measurement 2820 may be repeated n−1 times to obtain information (e.g., statistical information) regarding the time periods at which photons tend to arrive after a trigger event. Time-binned charge carriers may be aggregated in the corresponding charge storage bins as the measurement 2820 is repeated. Repeating the measurement 2820 may enable aggregating a sufficient number of charge carriers in the charge carrier storage bins to provide statistically meaningful results. For example, in the context of fluorescence lifetime measurement, it may be expected that a photon absorption event in response to a photon received from a fluorophore may occur relatively rarely. For example, such an event may be expected to occur once in about 10,000 measurements. Accordingly, a large number of measurements 2820 may need to be performed to aggregate a sufficient number of charge carriers in the charge carrier storage bins such that the results are statistically meaningful and/or have a sufficient signal to noise ratio. In some embodiments, the number of measurements n of a fluorophore that may be performed for fluorescence lifetime measurement may be 50,000 or more, 100,000 or more, 200,000 or more, 300,000 or more, 400,000 or more 500,000 or more, one million or more, two million or more five million or more, to enable capturing and binning a sufficient number of charge carriers in each bin (i.e., tens or hundreds, or more, in some embodiments). The measurements may be repeated at a frequency in the MHz range, such as between 50 MHz and 100 MHz, between 25 MHz and 200 MHz, between 10 MHz and 500 MHz, or between 1 MHz and 500 MHz, all ranges being inclusive of endpoints, or at another frequency. In some embodiments, after the measurement is repeated n−1 times, about one hundred carriers (e.g., electrons) may be accumulated in the time bins. However, this of course depends on the number of photons received. In some embodiments, the number of carriers accumulated in the time bins may be between 10 and 10,000, such as between 50 and 1,000, or any other suitable number. Method 2800 may be performed over any suitable time period in which photons are desired to be captured. In the context of fluorescence lifetime measurement, a suitable period for performing method 2800 may be 10 milliseconds, for example. In some embodiments, a measurement 2820 may be repeated at a frequency that is the MHz range. In some embodiments, the time bins may have a resolution on the scale of picoseconds or nanoseconds.

Figure 5E:
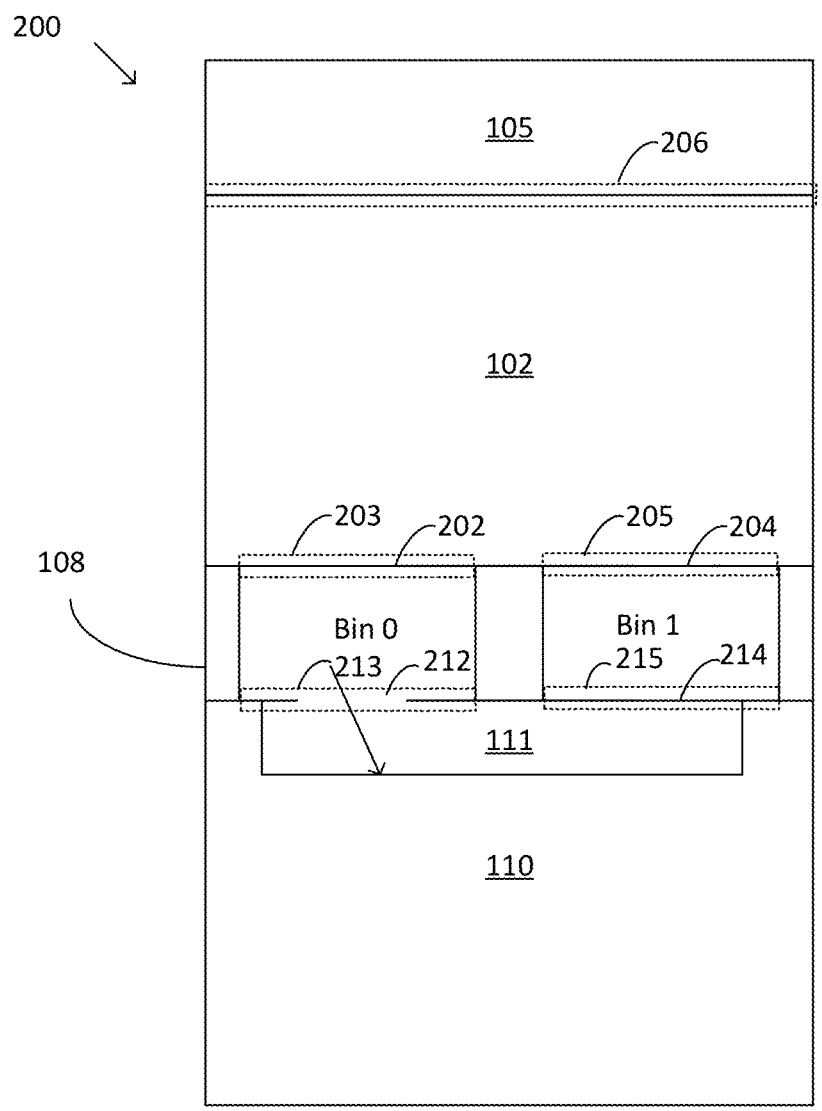
Figure 5F:
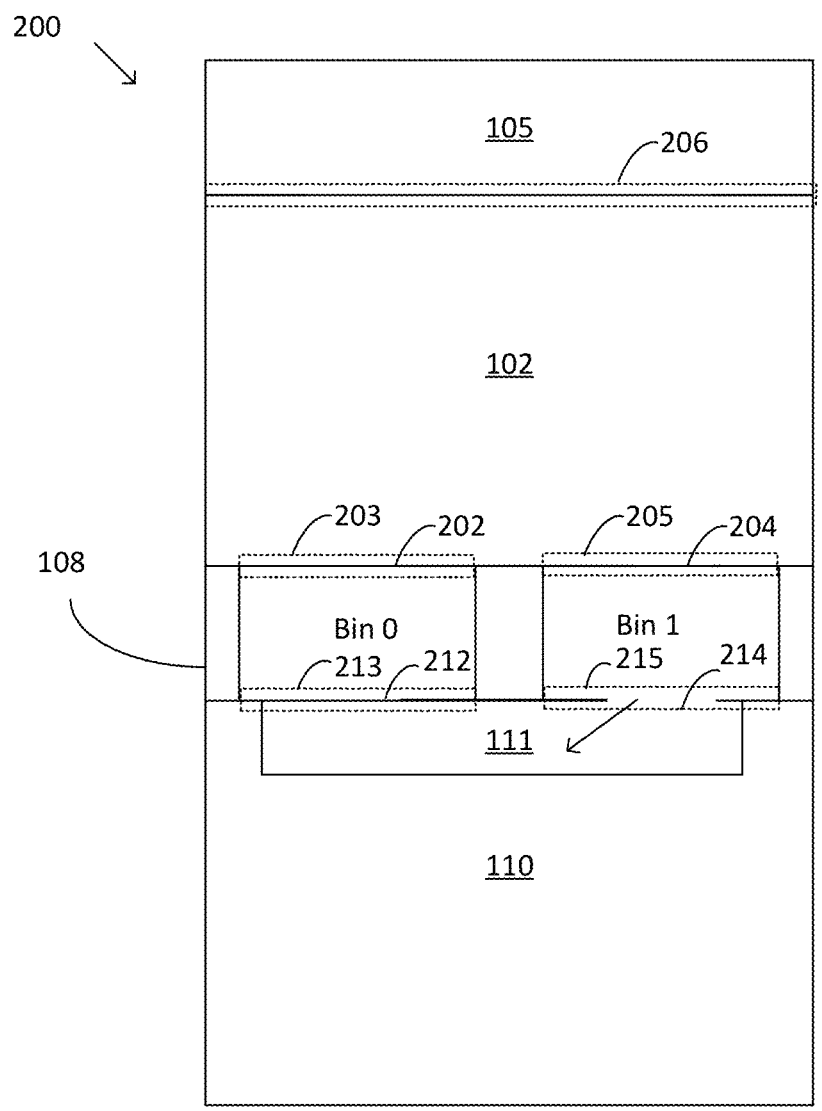
Figure 6:
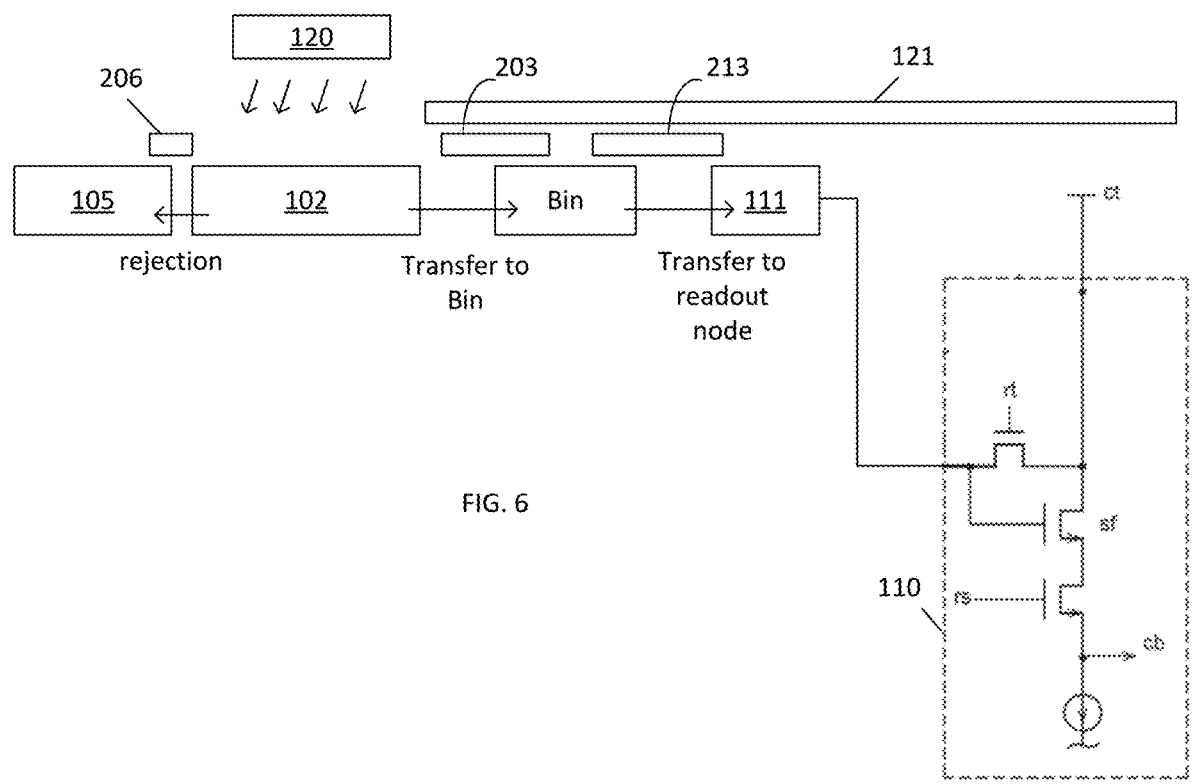
FIG. 6 shows a cross-sectional view of a direct binning pixel.

Once the allotted number of measurements n has been performed, the method proceeds to step 2810 of reading out the time bins. In step 2810, charge is transferred from the bins to a readout node 111, which may include a floating diffusion. Charge may be transferred from individual bins sequentially to readout node 111. For each bin, the charge is transferred to readout node 111 and then may be converted into a voltage using readout circuitry 110, an example of which is shown in FIG. 6. To transfer the charge from each bin, the voltages on electrodes 213 and/or 214 (FIG. 3) may be changed to lower a potential barrier between the bin and the readout node 111. An example of a readout sequence is to reset the voltage of readout node 111, then transfer the charge from bin 0 to readout node 111 by changing the voltage on electrode 213 to lower a potential barrier 212 between bin 0 and readout node 111. A potential gradient may be established that causes the charge to flow from bin 0 to readout node 111. This is illustrated in FIG. 5E. The charge transferred to readout node 111 may then be converted into a voltage and read out. The voltage of readout node 111 may then be reset. Then, the charge is transferred from bin 1 to readout node 111 by changing the voltage on electrode 215 to lower a potential barrier 214 between bin1 and readout node 111. A potential gradient may be established that causes the charge to flow from bin 1 to readout node 111. This is illustrated in FIG. 5F.

FIG. 6 shows a cross-sectional view of an example of pixel 200 along the line A-A' in FIG. 3. As illustrated, electrodes 206, 203 and 213 are formed on or over a semiconductor substrate. Light is received from a light source 120 at photon absorption/carrier generation area 102. Light source 120 may be any type of light source, including a luminescent sample (e.g., linked to a nucleic acid) or a region or scene to be imaged in imaging applications, by way of example and not limitation. Light source 120 may include unwanted excitation laser light. A light shield 121 prevents light from reaching another portion of the substrate, for example to prevent charges from being generated directly in the storage bins or readout nodes by stray excitation light, or other stray light. Light shield 121 may be formed of any suitable material, such a metal layer of the integrated circuit, by way of example and not limitation. FIG. 6 illustrates the opposite direction of charge transfer during rejection (to the left) and transfer to the bin (right).

Example Readout Circuitry and Sequences

As illustrated in FIG. 6, pixel 200 may include readout circuitry 110 that allows reading out the charge stored in the charge storage bin(s) of the charge carrier storage region 108. Pixel 200 may be an active pixel, such that readout circuitry 110 includes a readout amplifier, or a passive pixel in which readout circuitry 110 does not include a readout amplifier. Any suitable type of active pixel or passive pixel readout circuitry may be used. If readout circuitry 110 includes a readout amplifier, the readout amplifier may take the charge accumulated in a charge storage bin (e.g., bin 0, bin 1) as an input and produce a voltage representative of the charge in the charge storage bin as an output.

If readout circuitry 110 includes a readout amplifier, any suitable type of amplifier may be used. Examples of suitable amplifiers include amplifiers abased on a common source configuration and amplifiers abased on a source-follower configuration. One example of readout circuitry 110 based on a source-follower configuration is illustrated in FIG. 6. As shown in FIG. 6, readout region 110 may include a source follower buffer transistor sf, a reset transistor rt, and a row select transistor rs. However, the techniques described herein are not limited as to any particular amplifier configuration. In some embodiments, one or more transfer electrodes 213, 215 may be part of readout circuitry 110.

Any suitable readout techniques may be used, including noise reduction techniques. In some embodiments, readout circuitry 110 may read out the charge carrier storage bins using correlated double sampling. Correlated double sampling is technique in which a first sample may be taken of a node at a reset voltage level which includes an undetermined amount of noise, and a second sample may be taken of a signal level at the node including the same undetermined noise. The noise can be subtracted out by subtracting the sampled reset level from the sampled signal level.

Reading out the time bins may include converting the amount of charge aggregated in each of the charge storage bins into corresponding voltages, as discussed above. Readout from the time bins may be performed at any suitable rate, such as 50 Hz to 100 Hz, 10 Hz to 500 Hz, or another rate. In some embodiments, readout from the charge carrier storage bins of a pixel may be performed at the same time as collection of charge carriers in one or more charge carrier storage bins of the same pixel.

Transfer electrodes 213 and 215 may be charge coupled to each bin separately. A common readout node 111 may be charge coupled to all transfer electrodes. As illustrated in FIG. 6, the readout node 111 may be connected to the source of the reset transistor rt. The drains of the reset transistor rt and row select transistor rs may be connected to a high voltage supply. The gates of the reset transistor rt and row select transistor rs may be controlled by a row driver circuit. In some embodiments, the source of the transistor sf may be connected to the drain of the row select transistor rs. The gate of transistor sf may be connected to the readout node 111. In some embodiments, the source of the source follower may be connected to the column line readout.

Number and Timing of Time Bins

Any suitable number of time bins may be used. In FIG. 3, an example of a pixel with two bins has been illustrated. However, a pixel having any suitable number of bins may be produced based on the desired temporal resolution and other factors. Increasing the number of bins may increase the area taken up by each pixel, and may be achieved by reducing the overall number of pixels or by using a fabrication process having a smaller feature size. Using a small number of bins may allow increasing the number of pixels that can fit on a chip. In some embodiments, a single bin may be used to determine the number of photons arriving within a particular time period.

The timing of the time bins may be chosen in any suitable way. In some embodiments, the timing for the time bins may be a fixed such that the timing is the same in each measurement period. The timing may be set based upon a global timing signal. For example, a timing signal may establish the start of a measurement period, and time bins may be controlled to start and end based upon a predetermined amount of time having elapsed from the timing signal. In the fluorescence lifetime measurement context, the timing for the time bins may be set with respect to the timing of an excitation pulse based upon the possible range of fluorescence lifetimes that are expected to be detected. In the time-of-flight imaging context, the timing of the time bins may be set based on an expected distance range for the scene to be imaged. However, in some embodiments the timing of the time bins may be variable or programmable.

In some embodiments, the timing for the time bins may be set based upon the timing of a trigger event that initiates a measurement period for a measurement 2820. In the fluorescence lifetime measurement context, the timing for the time bins may be set in response to detecting the timing of an excitation pulse that excites a fluorophore. For example, when a light excitation pulse reaches the pixel 200, a surge of carriers may travel from the photon absorption/carrier generation region 102 to the drain. The accumulation of photogenerated carriers at the drain in response to the excitation pulse may cause a change in voltage of the drain. Accordingly, in some embodiments the excitation pulse may be detected by detecting the voltage of the drain. For example, a comparator may compare the voltage of the drain to a threshold, and may produce a pulse when the voltage of the drain exceeds the threshold. The timing of the pulse may be indicate the timing of the trigger event, and the timing of the time bins may be set based upon this timing. However, the techniques described herein are not limited in this respect, as any suitable technique may be used to detect the start of a measurement.

In some embodiments, the integrated device may be programmable to enable changing the timing of the time bins. In some embodiments, the timing of the time bins may be programmed for a particular set of measurements to be performed. For example, if the integrated device is used for a first type of test using a first set of markers having lifetimes within a first range, the time bins may be programmed to suitable values for discriminating lifetimes of the markers within that range. However, if the integrated device is used for another type of test that uses different markers having different lifetimes, the time bins may be changed by programming them to correspond to different time intervals suitable for the markers used in the second type of test. In some embodiments, the timing of the time bins may be controlled adaptively between measurements based on the results of a set of measurements.

Example Storage Bins

There are several ways to implement a charge storage bin as a potential well within the semiconductor region. In some embodiments, the potential well may be partially within the electrode 203 or 205. There are two types of transfer for moving charge in and out of the well. The accumulation transfer moves charge into the well. The readout transfer moves charge out of the well.

The following are possible characteristics of the potential well:

- The well may be of sufficient depth to store accumulated charge of at least 100 electrons for 10 ms at 30° C.
- The electrode 203 or 205 charge couples region 102 to the well.
- The well may be at least partially within the electrode 203 or 205.
- The well may be at higher potential during accumulation transfer than the full depletion voltage of region 102.
- The well's full depletion voltage may be at lower potential than the floating diffusion reset level during readout transfer.
- The well's potential may be dynamically modulated in order to serve both the requirements of accumulation transfer and readout transfer.

Figure 7:
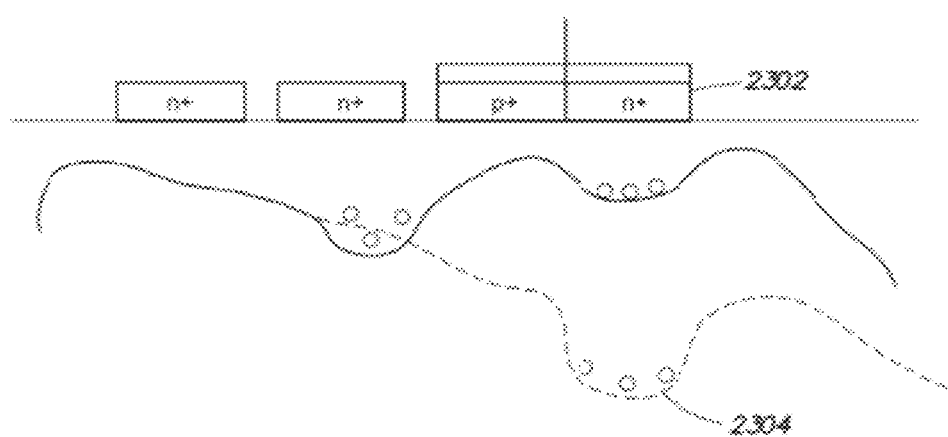
FIG. 7 shows a split-doped electrode having a p+ region and an n+ region.

There are a number of techniques to create the potential well for a bin, such as bin 0 or bin 1. As one example, one or more of electrodes 203, 205, 213 and 215 may be complementary-doped (split-doped). FIG. 7 shows a split-doped electrode 2302 having a p+ region and an n+ region. As shown in FIG. 7, the n+ region of split-doped electrode 2302 may produce a potential well under the n+ region that can confine charge carriers (e.g., electrons). FIG. 7 illustrates that keeping the voltage of the split-doped electrode 2302 high may produce a potential gradient as shown in dashed lines, which may confine charge carriers (e.g., electrons) in a potential well 2304. Lowering the voltage of split-doped electrode 2302 may raise the electric potential under the split-doped electrode 2302 to enable transferring charge trapped in the potential well 2304 to a charge storage bin, for example.

Electrode 2302 may be doped P+ on the side of region 102 and N+ on the bin side. The work function difference may create a voltage gradient, such as 1 volt, for example. A second option is to place a buried channel n-type implant at the well location that is modulated by the electrode. When the electrode is at high potential the well potential increases beyond the collection region. A third option is to produce a replica diode that is the same as the diode of region 102. The diode may be a buried diode, as with the diode of region 102, that has the same implants. It may be formed between the barriers 202 or 204 and the transfer electrode 213. The depletion voltage may be adjusted with n-type implant that extends across the readout transfer gate. The electrode forming barrier 202 or 204 may be doped N+ while the readout transfer electrode may be doped P+. In some embodiments, a combination of the above-described techniques may be used to form the potential well for a bin.

FIG. 8 shows a plan view of an example of a direct binning pixel 200, according to some embodiments. As illustrated, region 102 may have a circular shape, though the techniques described herein are not limited in the respect.

Figure 9:
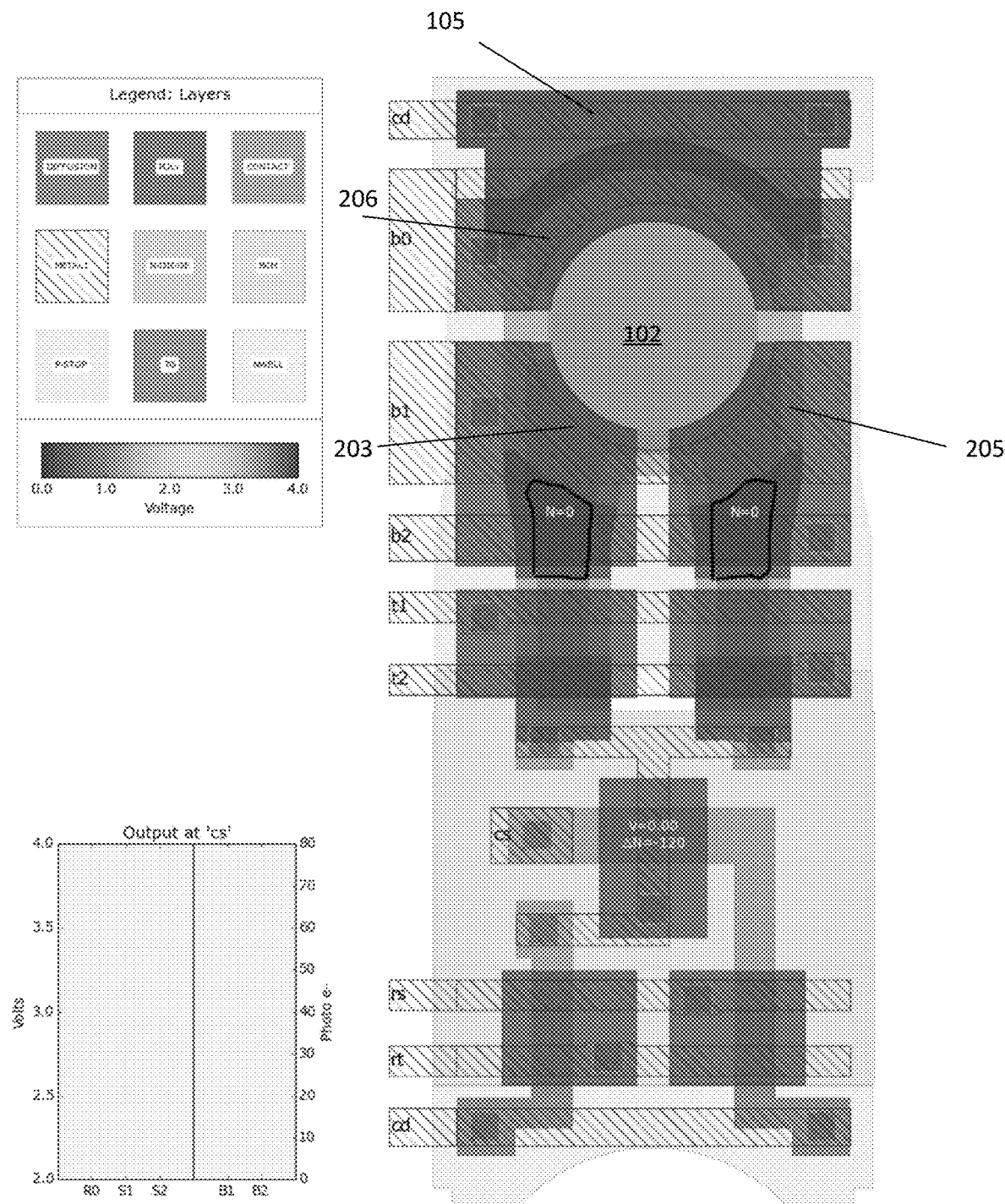
FIG. 9 shows a plan view of another example of a direct binning pixel.

FIG. 9 shows a plan view of another example of a direct binning pixel 200, according to some embodiments. FIG. 9 shows metal terminals overlying and electrically connected to the underlying polysilicon electrodes. Metal region cd is connected to rejection region 105, metal region b0 is connected to electrode 206, metal region b1 is connected to electrode 203, and metal region b2 is connected to electrode 205. Metal region t1 connects to a polysilicon electrode that serves as a transfer gate to bin 0, which allows transferring out the charge stored in bin 0 for readout. Similarly, metal region t2 connects to another polysilicon electrode that serves as a transfer gate to bin 1, which allows transferring out the charge stored in bin 1 for readout.

There are pocket implants that are positioned on the lower part of electrodes 203 and 205, as shown with the "TG" layer. The intersection between the diffusion and pocket implants is labeled with N=0. Due to side wall implants, the black markings are where pocket potential occurs. In this example, a pocket extends between the electrodes. However, the techniques and devices described herein are not limited in this respect.

The position of a bin may be under an electrode, in a region not covered by the electrode, or both under an electrode and in a region not covered by an electrode. For example, bin 0 may be under electrode 203, in the region not under electrode 203 between electrode 203 and the polysilicon transfer electrode connected to t1, or both under electrode 203 and in a region not under electrode 203.

FIGS. 10-14 show the doping concentration in the semiconductor material and the potential gradient of pixel 200 at various steps of method 2800 for an embodiment of a pixel 200.

Figure 10:
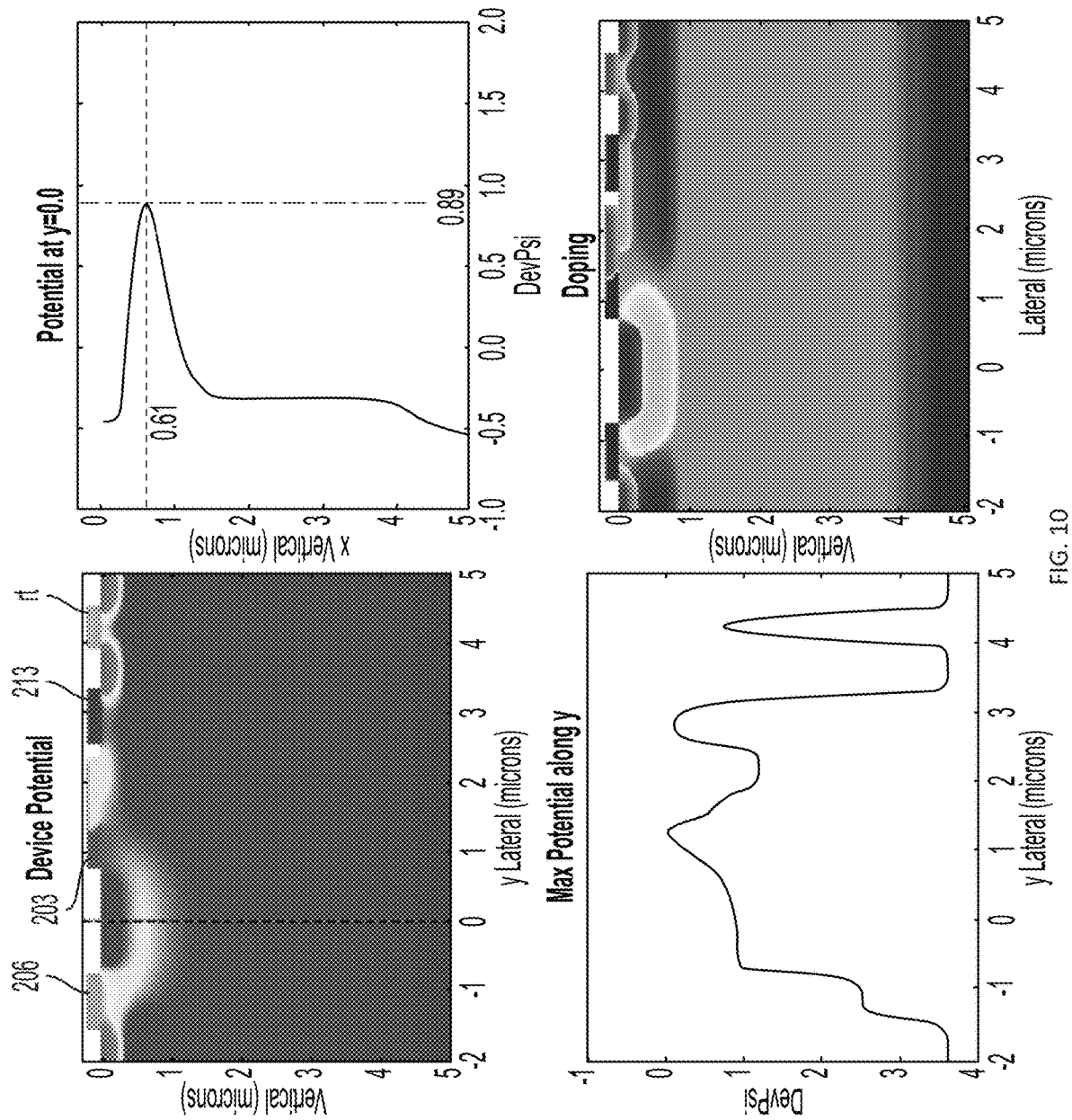
FIG. 10 shows the potential in the direct binning pixel during the rejection period.

FIG. 10 shows the potential during the rejection period of step 2802, which also corresponds to FIG. 5A. The plot in the bottom left shows the potential along the y dimension of FIG. 8. The photon absorption/carrier generation region 102 is centered at y=0. As seen in the plots on the bottom left and the upper left, when the electrode of the rejection region to the left of y=0 goes high, the potential drops toward the rejection region at the left of y=0. Accordingly, carriers are transferred from photon absorption/carrier generation region 102 to the rejection region 105. The plot in the bottom right shows the doping concentration.

Figure 11:
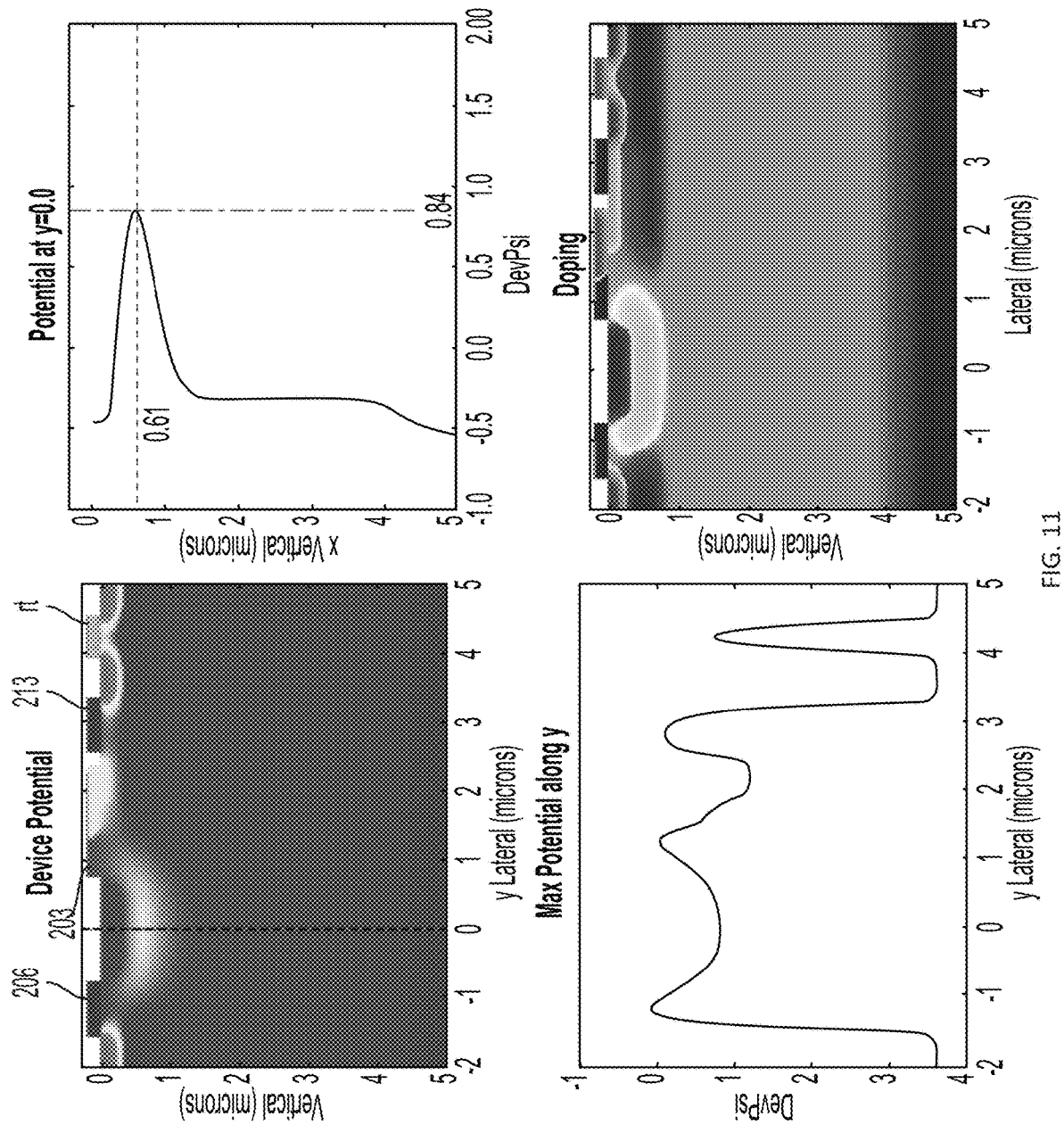
FIG. 11 shows the potential in the direct binning pixel during a period in which potential barriers to the rejection region and the bins are raised.

FIG. 11 shows the potential during a period in which potential barriers to the rejection region and the bins are raised (as in FIG. 5C). In this state, any charge carriers produced in region 102 are confined in region 102 due to the bowl-shaped potential well produced around y=0.

Figure 12:
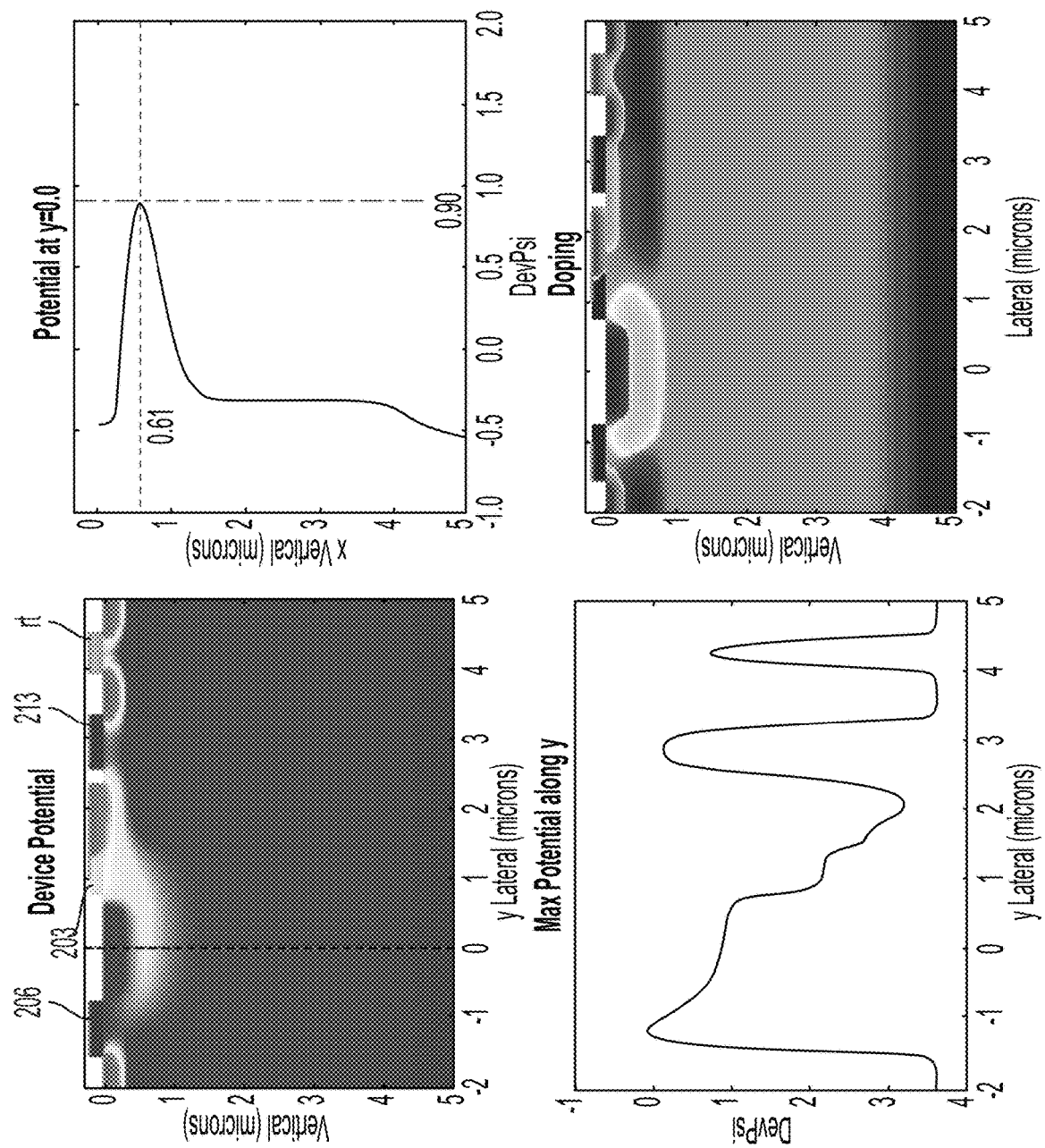
FIG. 12 shows the potential in the direct binning pixel in a period where charge may be transferred to a bin.

FIG. 12 shows the potential during steps 2806 and 2808 where charge may be transferred to a bin, corresponding to FIGS. 5B and 5D. The potential in the y dimension is similar for the cases where charge is transferred to bin 0 and bin 1. In this respect, FIG. 12 does not show the gradient along the lateral dimension of FIG. 8 that would drive a carrier toward one bin vs. the other bin. As shown in FIG. 12, the potential falls off to the right of region 102 toward the bin, which would drive any carrier that is present into the corresponding bin.

Figure 13:
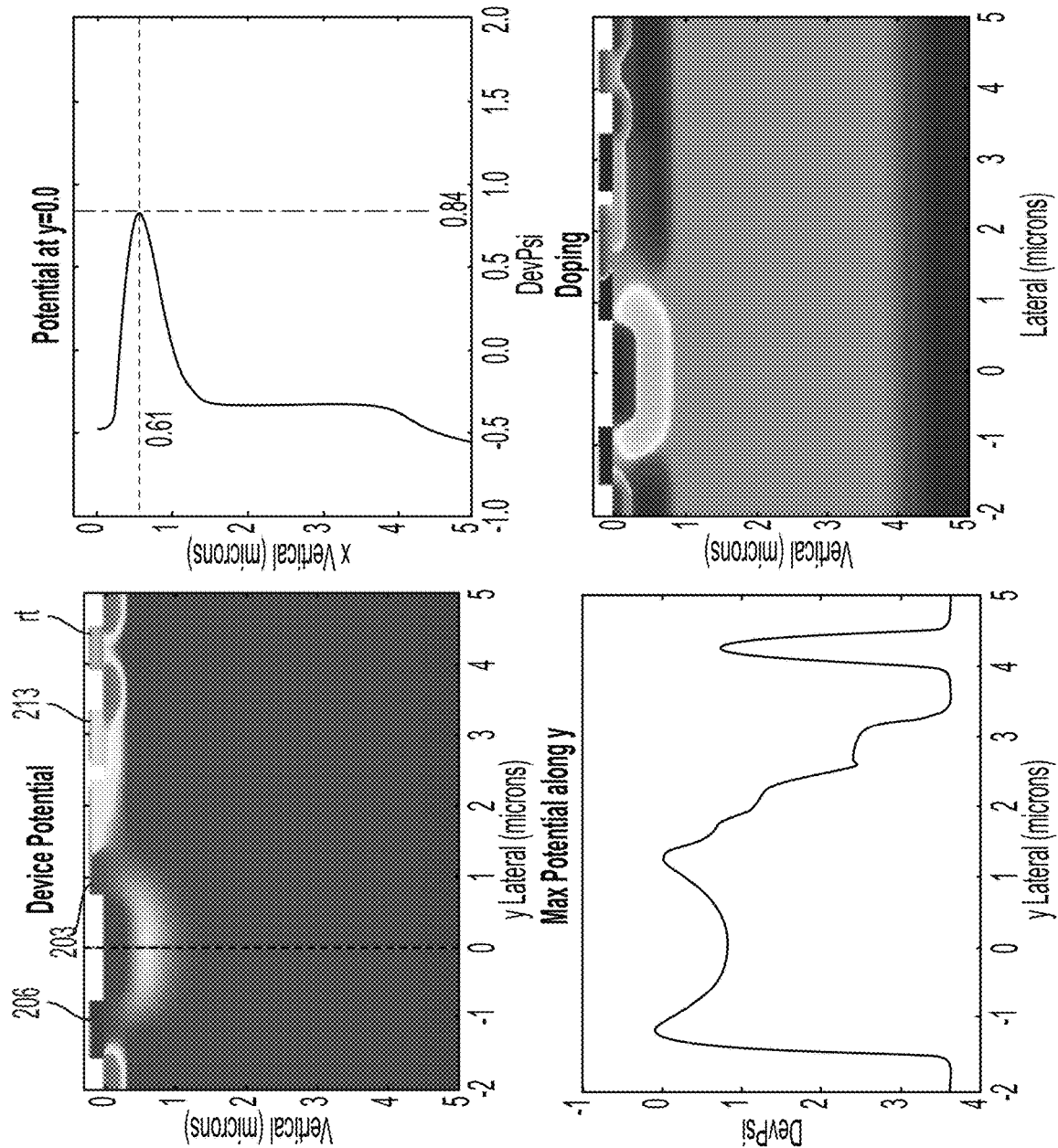
FIG. 13 shows transfer of the charge stored in a bin to the floating diffusion FD by lowering a potential barrier produced by a transfer gate.
Figure 14:
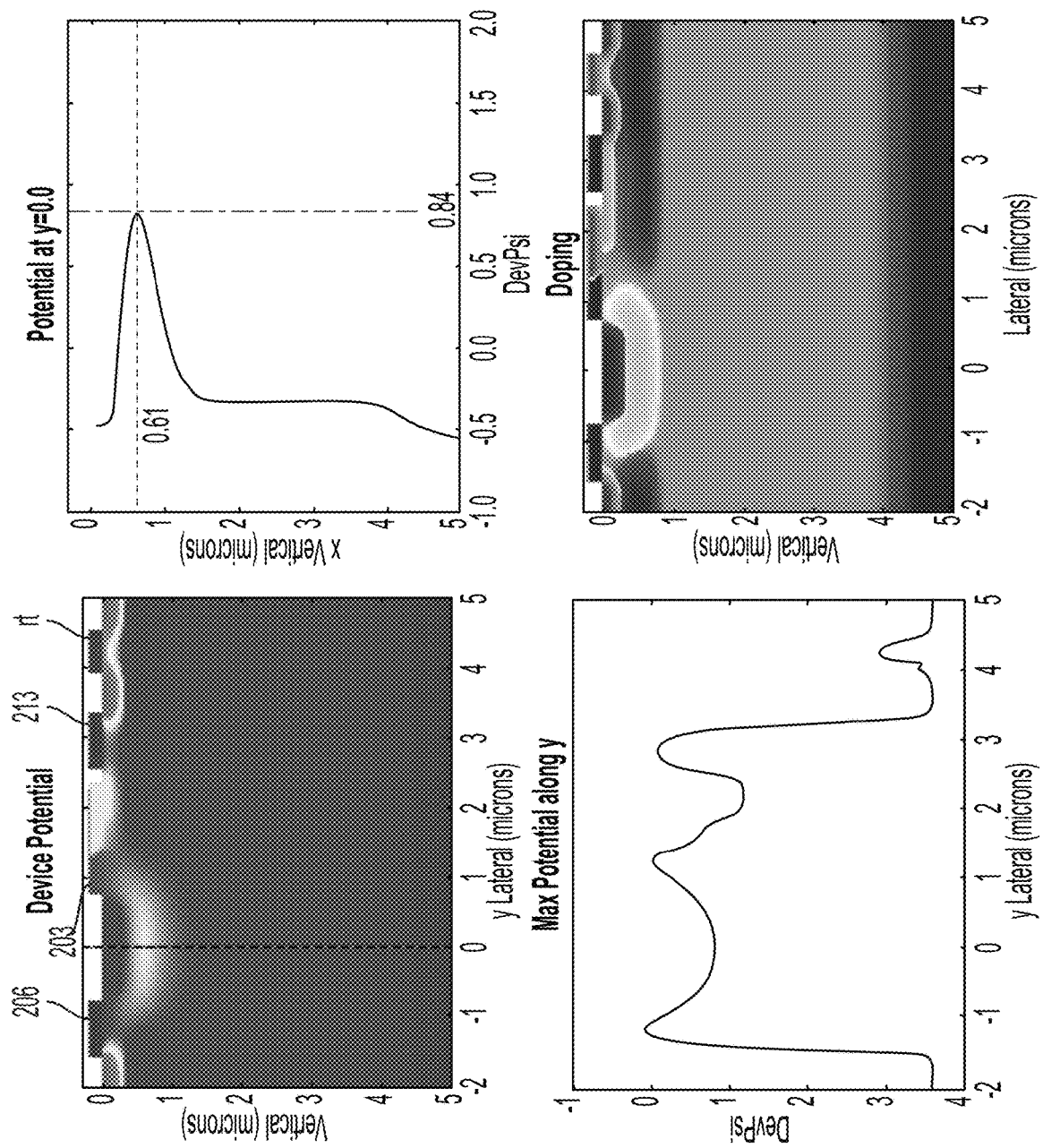
FIG. 14 illustrates resetting the floating diffusion FD.

FIGS. 13 and 14 illustrate the potential during the readout phase. FIG. 13 shows transfer of the charge stored in a bin to the floating diffusion FD by lowering a potential barrier produced by a transfer gate. FIG. 14 illustrates resetting the floating diffusion FD.

Vertical Rejection

The inventors have recognized and appreciated a problem arising from photogeneration of charge carriers deep within a semiconductor substrate. Since there may be no significant potential gradient deep within the substrate, carriers that are generated in this region may be slow-moving, and may not take a predictable path. In some cases, deep-generated carriers may ultimately travel to the surface and become confined in region 102. Collecting such carriers in region 102 is undesirable, as they do not correspond to photons that arrived during the current measurement period, and therefore are noise that should be rejected. The inventors have developed structures and techniques to reject deep-generated carriers that may be used in a direct-binning pixel or another type of pixel. Prior to discussing such structures and techniques, the generation and movement of deep-generated carriers will be discussed.

Figure 15:
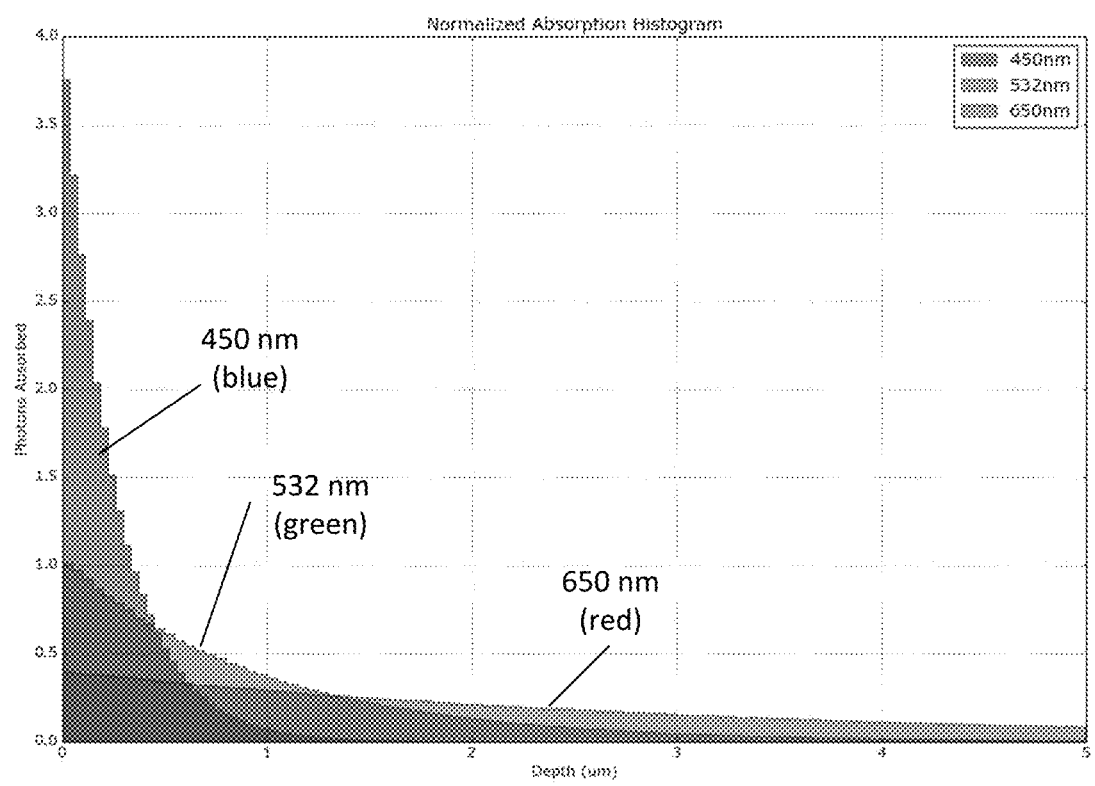
FIG. 15 shows a plot of absorption depth as a function of wavelength.

As shown in FIG. 15, absorption depth is a function of wavelength such that longer wavelengths penetrate deeper into a semiconductor before the light is absorbed. The absorption depth is given by the inverse of the absorption coefficient, or 1/a. The intensity decays exponentially into the substrate such that the absorption depth is the distance into the material at which the light drops to about 36% of the surface intensity, 1/e, or 1 tau ($\tau$). Short wavelength light (blue) has a large absorption coefficient such that it is absorbed within a short distance of the surface, while longer wavelength light (red) is absorbed at a lower rate.

An epi-wafer includes a lightly doped (e.g., $2\times10^{15}$ cm$^{-3}$) epitaxy region, 3-5 microns thick, with highly doped handle. There is no potential gradient in the active area so the electric field is minimal. Carriers undergo motion from 3 sources:

1) Thermal
2) Drift
3) Diffusion

With no electric field or doping gradient, carriers collide with vibrating atoms of the semiconductor in a stochastic process. The carriers electrostatically interact with dopants and other carriers. The mean time between free collisions at 300° K is about $1e^{-13}$ s with a thermal velocity of $1e^{-7}$ cm/s. The characteristic mean free path is about 10 nm.

Figure 16:
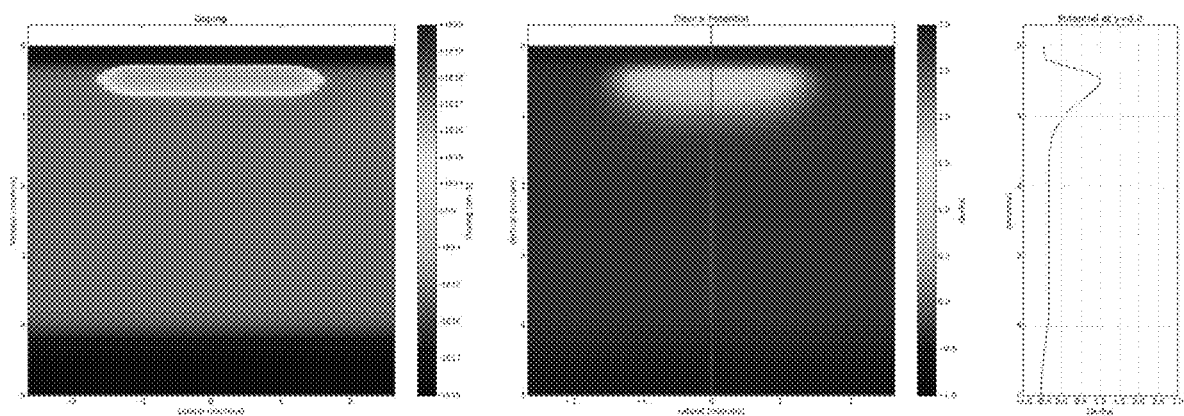
FIG. 16 shows the doping profile and potential for an example of a photodiode.

FIG. 16 shows the doping profile and potential for the photodiode of region 102. A fully depleted lightly doped buried n-type region of ($1\times10^{16}$ cm$^{-3}$) produces an electric field that pulls carriers into the region of highest potential. Carriers generated below the depletion region diffuse into the electric field before becoming confined. The diffusion process is slow and causes carriers to arrive well after they are generated.

The depth of the buried diode region may be limited by the CMOS process at the stage the implant is implemented (energy <400 keV). The active region and extension of the electric field may be less than 1.5 µm deep, which results in about 20% of photo-electrons entering a region with flat electric field. In a 10 ns cycle, after simulating 1 million photons, about 1 in 40 photons are still lagging in the substrate after half the cycle, or 5 ns. Within the first 100 ps, about 1 in 10 photons are still lagging. This represents a best case rejection ratio of 10 to 1 using a 100 ps rejection latency.

It is desired to drain the deep-generated carriers and/or at least prevent them from reaching the photodiode region near the surface. The inventors have developed structures and techniques for doing so. In some embodiments, "deep-generated carriers" refers to carriers generated more than 1 micron below the surface. However, the invention is not limited in this respect, as the depth at which the carriers may become an issue may vary for different materials and process technologies.

Figure 17:
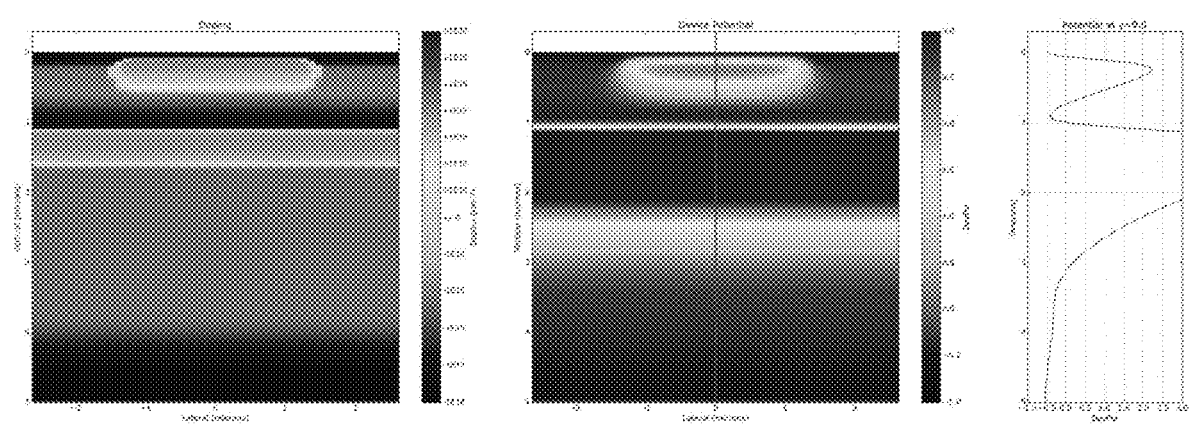
FIG. 17 shows a deep doped region that may prevent deep-generated carriers from reaching the surface.
Figure 18:
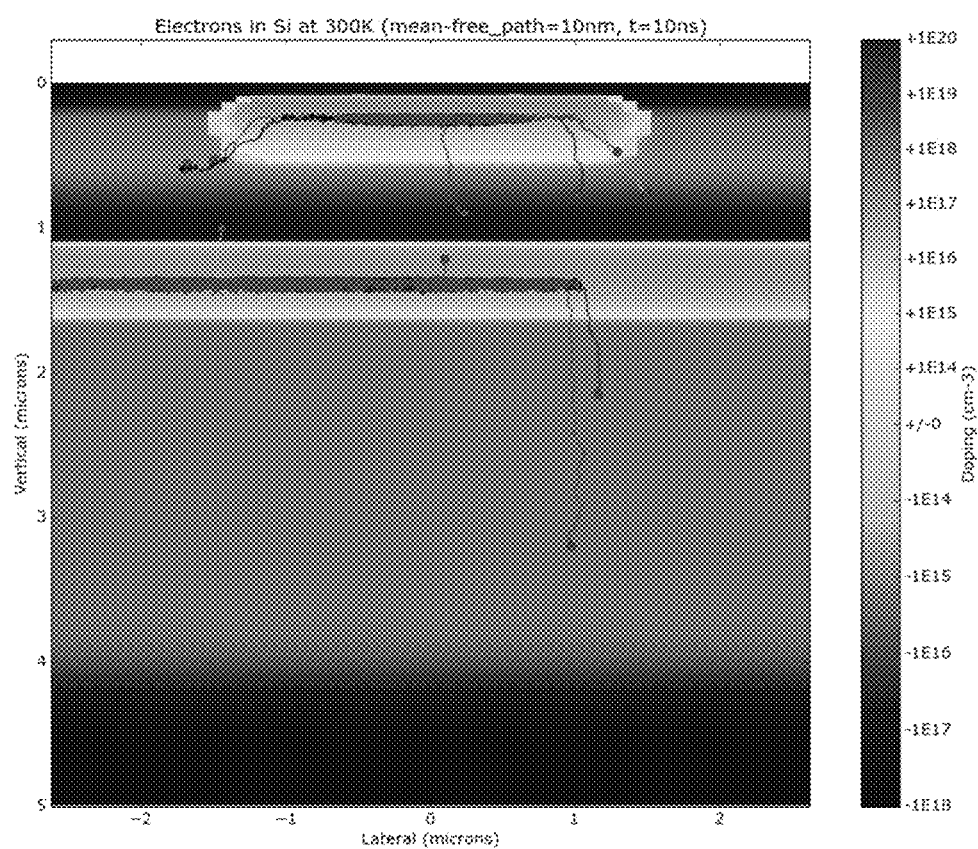
FIG. 18 shows a simulation of the electron motion for 10 ns, illustrating carriers are drawn into the deep n-well region.

One technique is to form a drain or barrier below the photodiode that blocks deep-generated carriers from entering the photodiode. FIG. 17 shows a deep doped region that may prevent deep-generated carriers from reaching the surface. The deep doped region may be a deep implant using an energy of 900 keV, or any other suitable energy. In some embodiments, the deep implant may be non-continuous (such as in FIG. 20, for example) to allow the surface to be at the same potential as the bottom of the substrate. FIG. 18 shows a simulation of the electron motion for 10 ns, illustrating carriers are drawn into the deep n-well region.

If the deep doped region is n-type, it may be connected to the rejection region, and thus a supply voltage, to collect and transfer deep-generated carriers to a drain. If the deep doped region is p-type, it may form a barrier that blocks deep doped carriers and prevents them from reaching the photodiode.

Deep carriers may be rejected when using an epitaxy substrate of 3-5 um thickness, or any other suitable thickness. The photogenerated carriers within 1 um of the surface may be collected into the depleted diode N-region.

Figure 19:
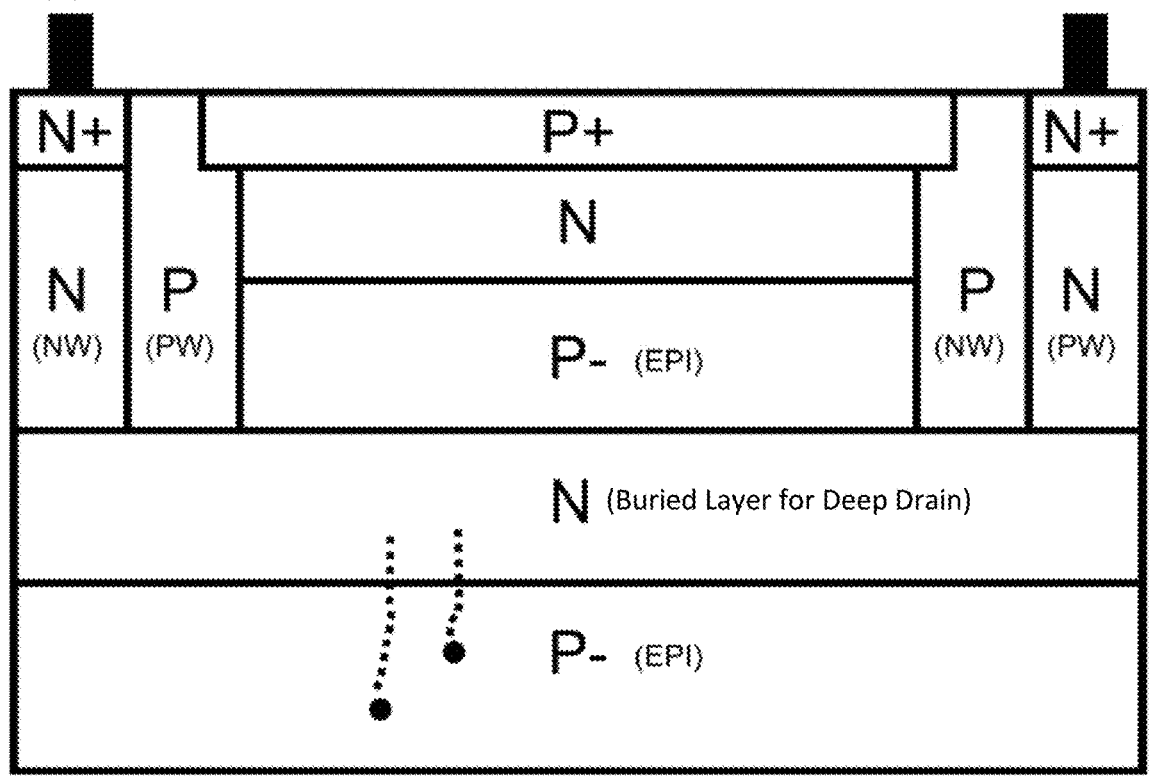
FIG. 19 shows an N-type buried layer (deep drain) is biased at high potential.
Figure 20:
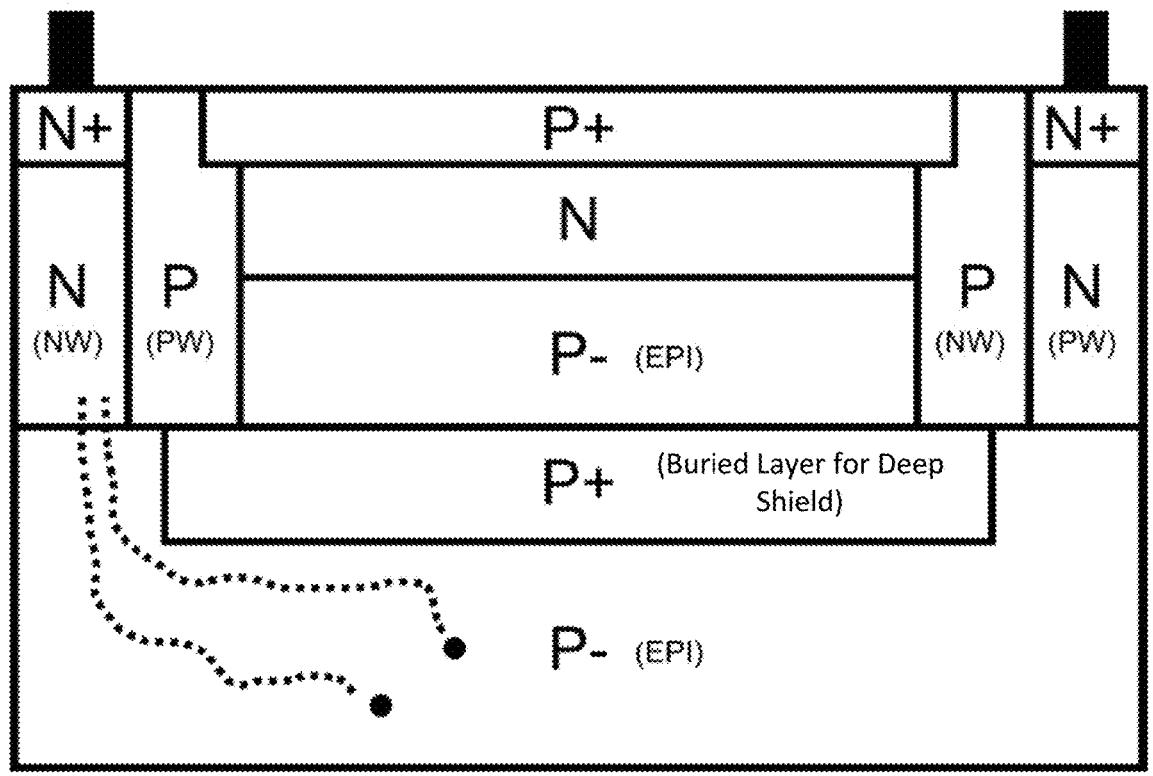
FIG. 20 shows a P+-type buried layer (deep shield) in contact with the substrate.

Two separate techniques may be implemented to handle deep carriers:

1) One technique is a buried drain. FIG. 19 shows an example, in which an N-type buried layer (deep drain) is biased at high potential (e.g., 3 volts). Deep photo-electrons are pulled into the N-type buried layer and drained away at the contacts.
2) Another technique is a buried shield. FIG. 20 shows a P+-type buried layer (deep shield) in contact with the substrate. Deep photo-electrons are repelled from the P+-type buried layer and diffuse into N-type pickups and drained away at the contacts. The P+-type buried layer is non-continuous and allows the diode structure to remain biased to substrate potential from the bottom side at low potential. For fast dynamic switching of the electrodes interfacing to the diode, this can be an advantage because the diode depletion voltage remains fixed even at high frequency.

The N and P region on the left and right sides of the buried diode may be implemented using standard NWELL (NW) and PWELL (PW) processing. The N+ taps to the NWELL may be standard source drain highly doped implants. The deep N region may be a high energy phosphorus implant above 1000 keV. The deep P+ region may be a high energy boron implant above 500 keV.

Another technique to drain deep generated carriers is to produce a drift field in the substrate that pulls deep-generated carriers away from the surface. The drift field may be generated by producing a vertical potential gradient in the substrate.

Another technique to avoid deep generated carriers is to make the semiconductor region (e.g., an epitaxial region) very thin, such as thinner than three microns, thinner than two microns or thinner than 1 micron.

Additional Embodiments

Figure 21:
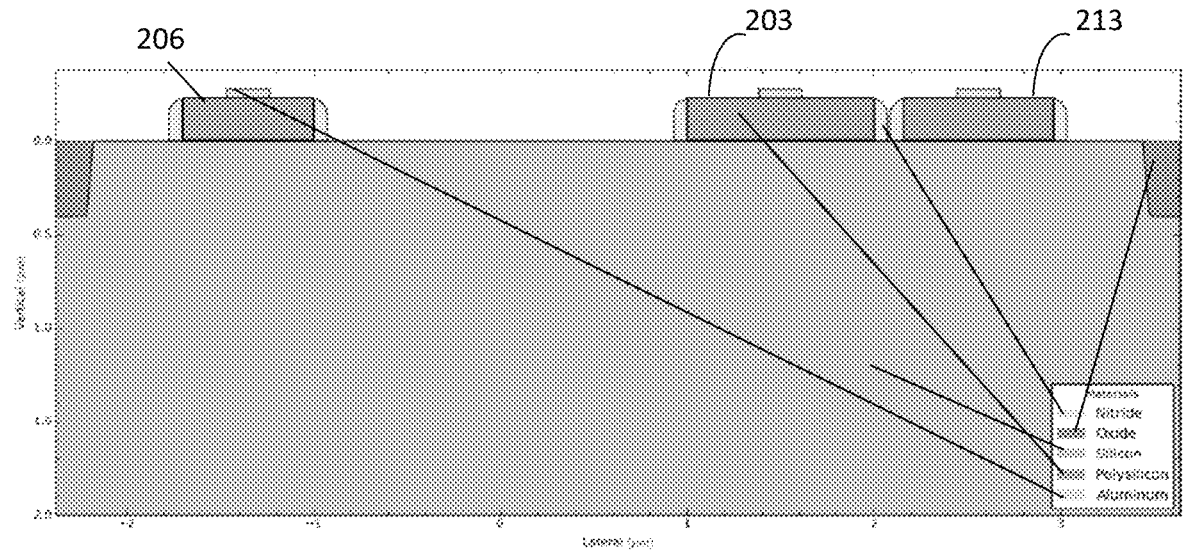
FIG. 21 shows examples of materials from which the integrated circuit may be fabricated.

FIG. 21 shows examples of materials from which the integrated circuit may be fabricated. A pixel may be formed in a semiconductor region, which in some embodiments may be silicon. Insulating regions, such as silicon oxide regions, may insulate areas of the integrated circuit from one another. The electrodes (e.g., electrodes 206, 203 and 213) may be formed of polysilicon or another conductor. Insulating spacers may be positioned at the sides of the electrodes. For example, the insulating regions may be formed of silicon nitride. A metal such as aluminum may be disposed on the electrodes to make electrical contact thereto. However, other materials may be used, as the devices described herein are not limited as to particular materials.

Figure 22:
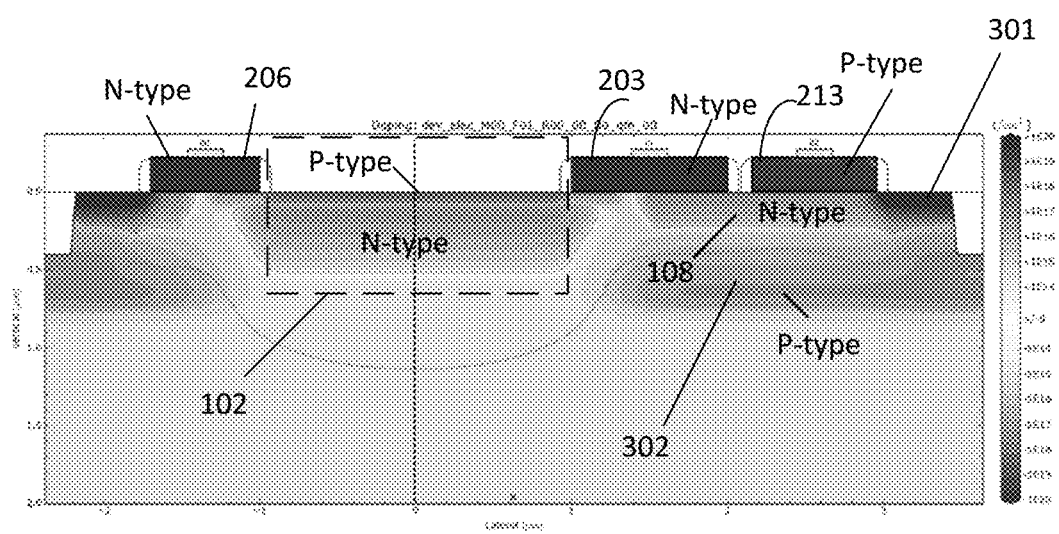
FIG. 22 shows an example of a doping profile for a direct binning pixel, according to some embodiments.

FIG. 22 shows an example of a doping profile for a pixel 200, according to some embodiments. The photodetection region 102 includes a photodiode having a P-type region at the surface and a buried N-type region. Electrodes 206 and 203 may be doped N-type. Electrode 213 may be doped P-type. The difference in doping between electrode 203 and electrode 213 may create a workfunction difference that allows one implant to be formed in region 108 to allow for confining charge carriers, as opposed to a plurality of implants. However, this is optional, and in some embodiments region 108 may include a plurality of implants. The charge storage region 108 below the electrodes 203 and/or 213 is doped N-type in this example. A highly doped region 301 may be formed in the semiconductor region to the far side of the electrode 213 opposite the photodiode. A barrier implant 302 may be formed to prevent carriers from entering the charge storage region 108 from deep in the substrate. In this example, the barrier implant may be P-type.

The bin may include an implant that spans half of the electrode 203 through the 213 electrode into the diffusion. The bin barrier to the output may be formed by the workfunction difference between a P+ and N+ doped gate electrode. This can form a sufficient 1.1V barrier difference. This difference can be extended by applying a difference voltage between electrode 203 and electrode 213. For example, electrode 213 can be set to 0V and electrode 203 can be set to 0.4V. This creates a 1.5V difference.

The potential barrier to the input may be formed by a boron implant at the diode interface. The barrier potential is relative to the maximum depletion voltage of the bin implant. The bin implant dose and energy may determine the maximum potential depth of the bin. This may tuned in the process to allow for a sufficient barrier to the input side of the bin. The output side has a robust barrier due to the work function difference and is also tunable by voltages. The input barrier is more important to tune. The bin potential depth may be tuned by applied voltage to the electrode 203. However, this also affects the barrier to the input diode. The barrier to the input diode may be gate controlled. Therefore, the bin implant dose and energy may be tuned in order to deliver a sufficient barrier at maximum bin depletion potential. Using the same mask as the bin implant, a deep, high dose boron implant may form a barrier to the substrate which prevents pick up of stray electrons.

Figure 23:
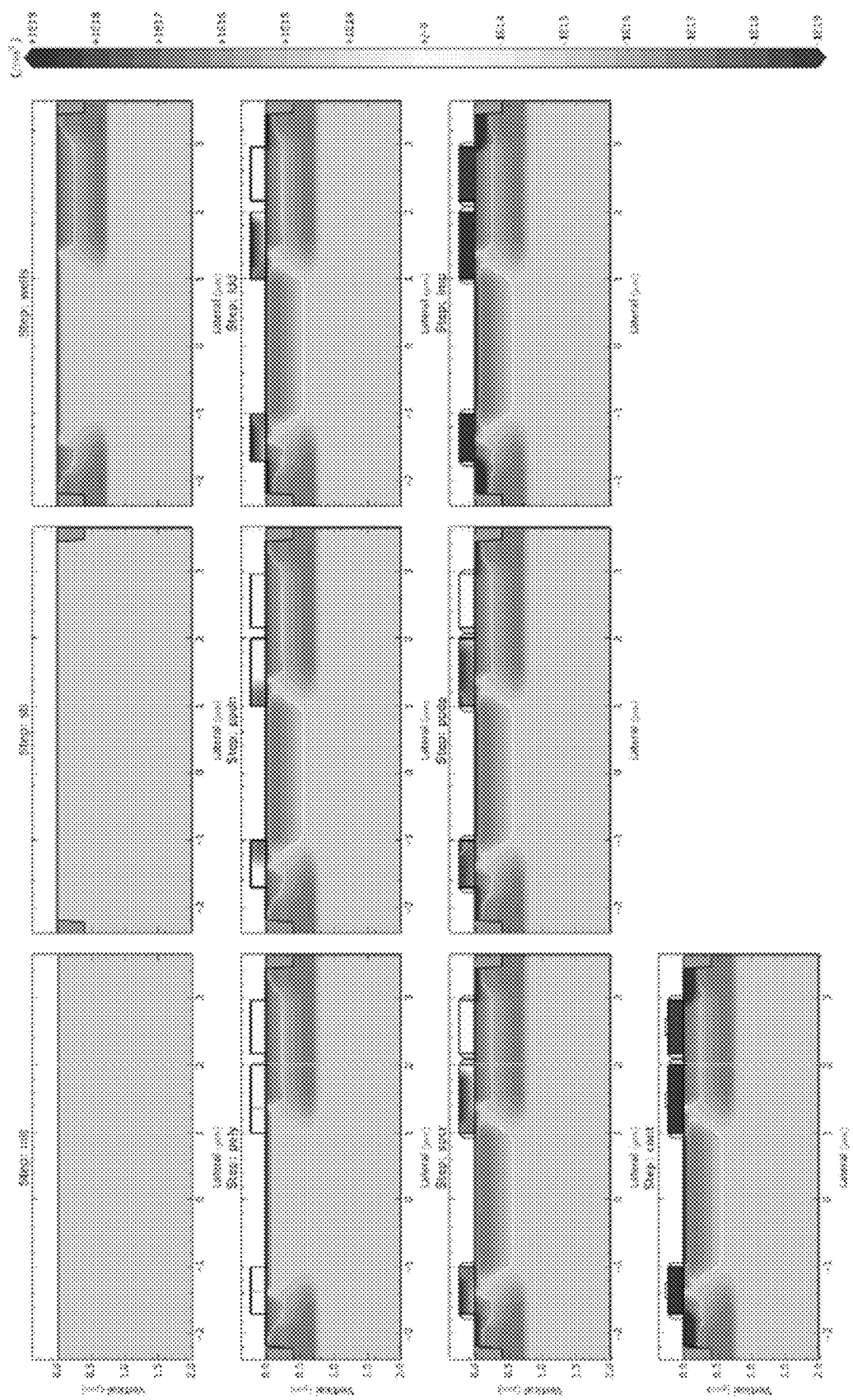
FIG. 23 shows an exemplary process sequence for forming the direct binning pixel with the doping profile illustrated in FIG. 22.

FIG. 23 shows an exemplary process sequence for forming the pixel 200 with the doping profile illustrated in FIG. 22. The process may include any suitable sequence of dopant implants and/or diffusions. However, it should be appreciated that the process of FIG. 23 is by way of example, and other suitable processes may be used.

Figure 24:
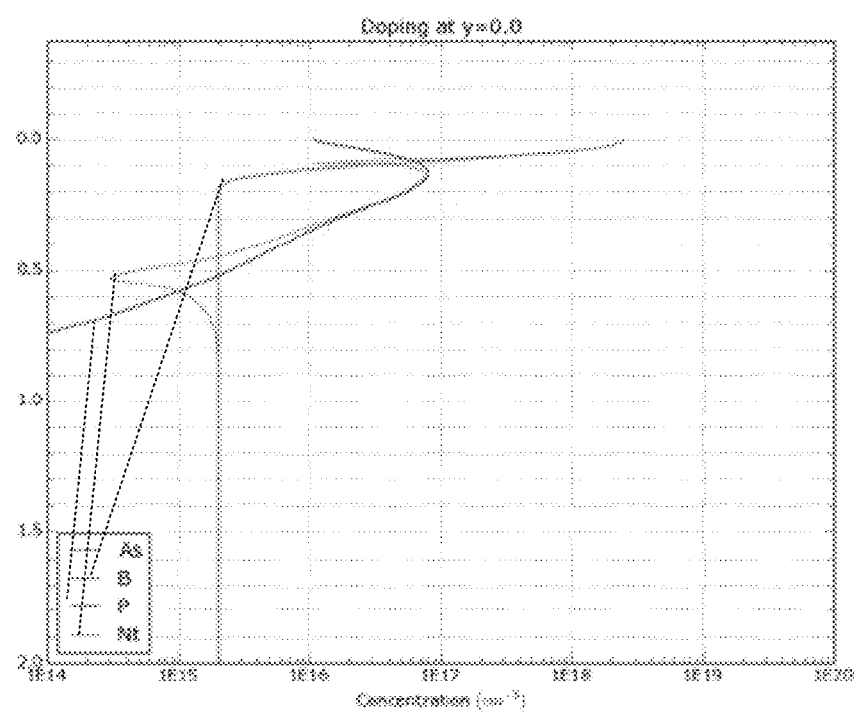
FIG. 24 shows a plot of an exemplary doping profile for arsenic, boron, phosphorous, and nitrogen along the line y=0 of FIG. 22.

FIG. 24 shows a plot of an exemplary doping profile for arsenic, boron, phosphorous, and Nt along the line y=0 of FIG. 22. Depth into the substrate is shown on the vertical axis, and concentration on the horizontal axis.

Figure 25:
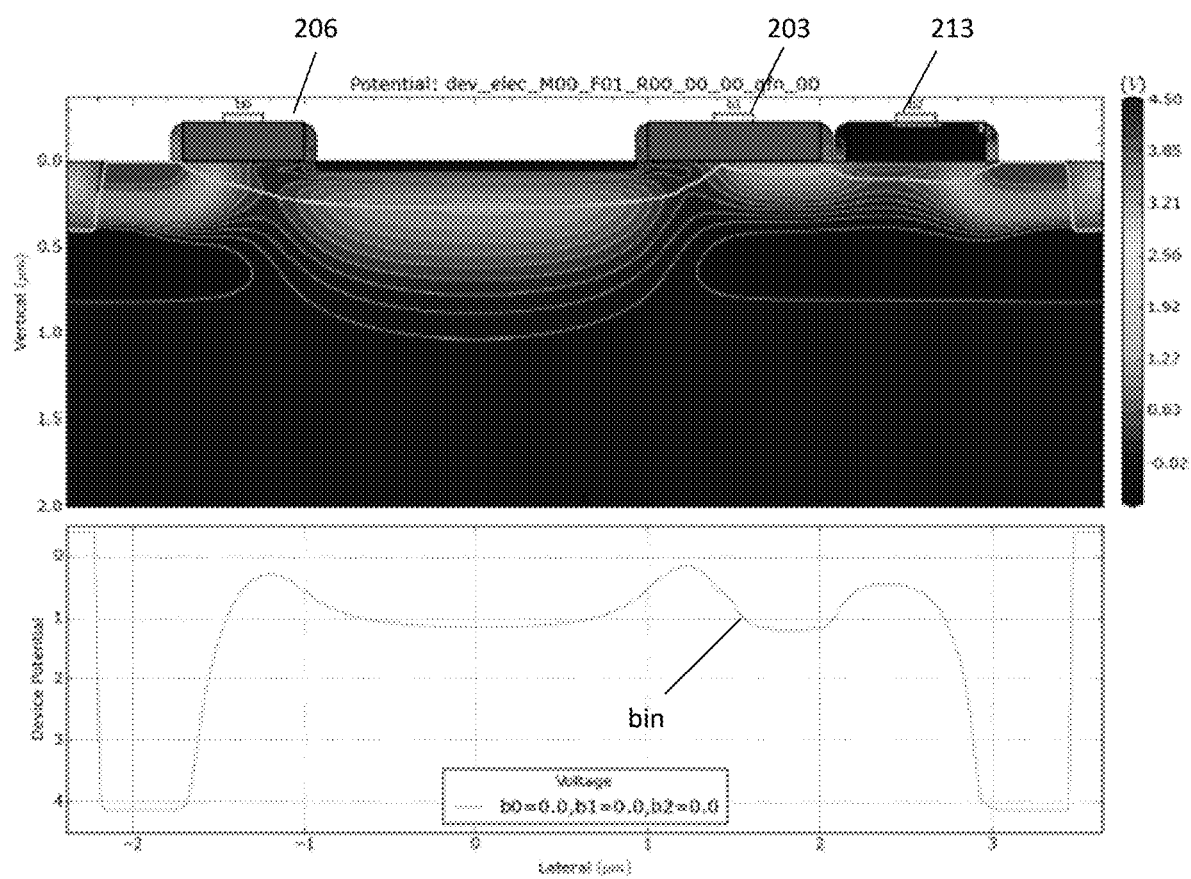
FIG. 25 shows a plot of electric potential in the pixel of FIG. 23 when all the barriers are closed by setting the voltages of all electrodes to 0V.

FIG. 25 shows a plot of electric potential in the pixel of FIG. 22 when all the barriers are closed by setting the voltages of all electrodes to 0V. As illustrated, a potential well is produced that allows confining carriers in the bin.

Figure 26:
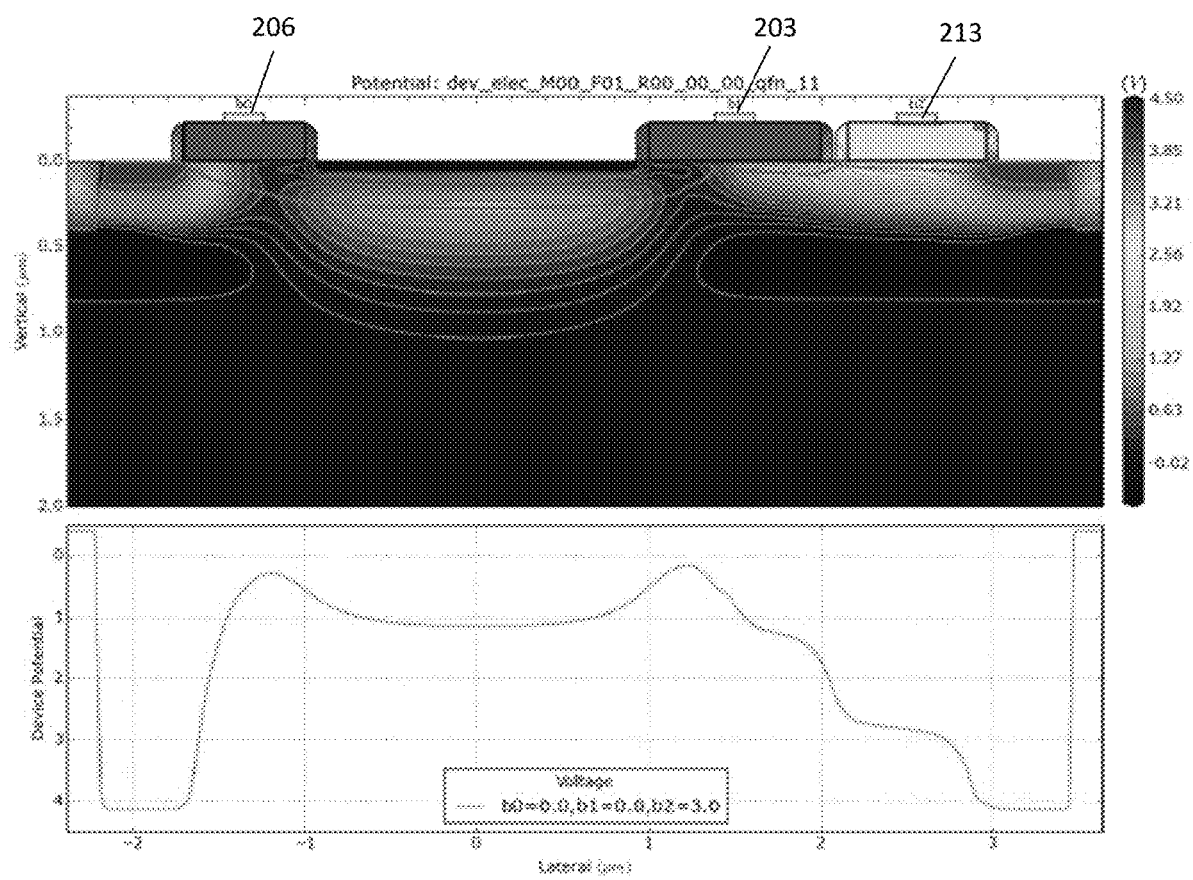
FIG. 26 shows a plot of the electric potential in the pixel of FIG. 23 when the voltage of electrode 213 is set to 3V.

FIG. 26 shows a plot of the electric potential in the pixel of FIG. 22 when the voltage of electrode 213 is set to 3V. Raising the voltage on electrode 213 lowers the barrier between the bin and the readout node 111.

Figure 27:
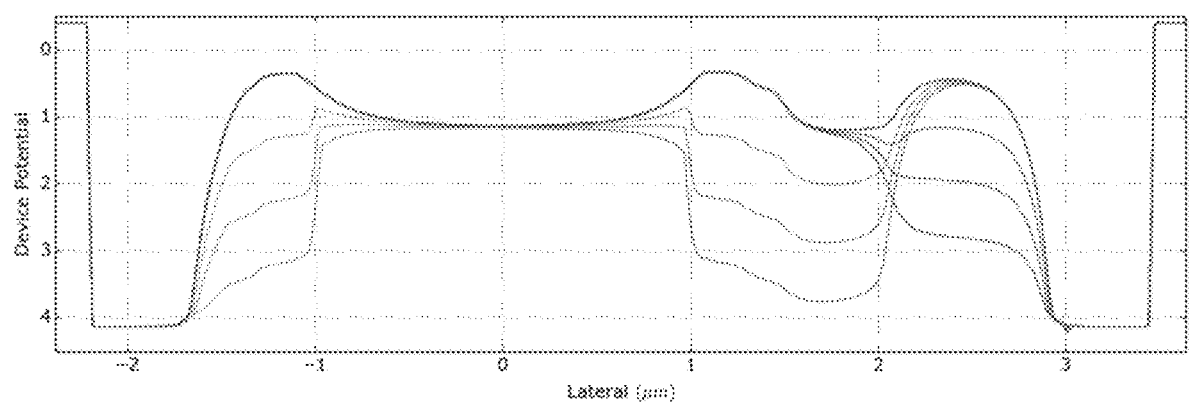
FIG. 27 shows curves of potential within the substrate as the voltages of the electrodes are varied.

FIG. 27 shows curves of potential within the substrate as the voltages of the electrodes 206, 203 and 213 are varied.

Figure 28:
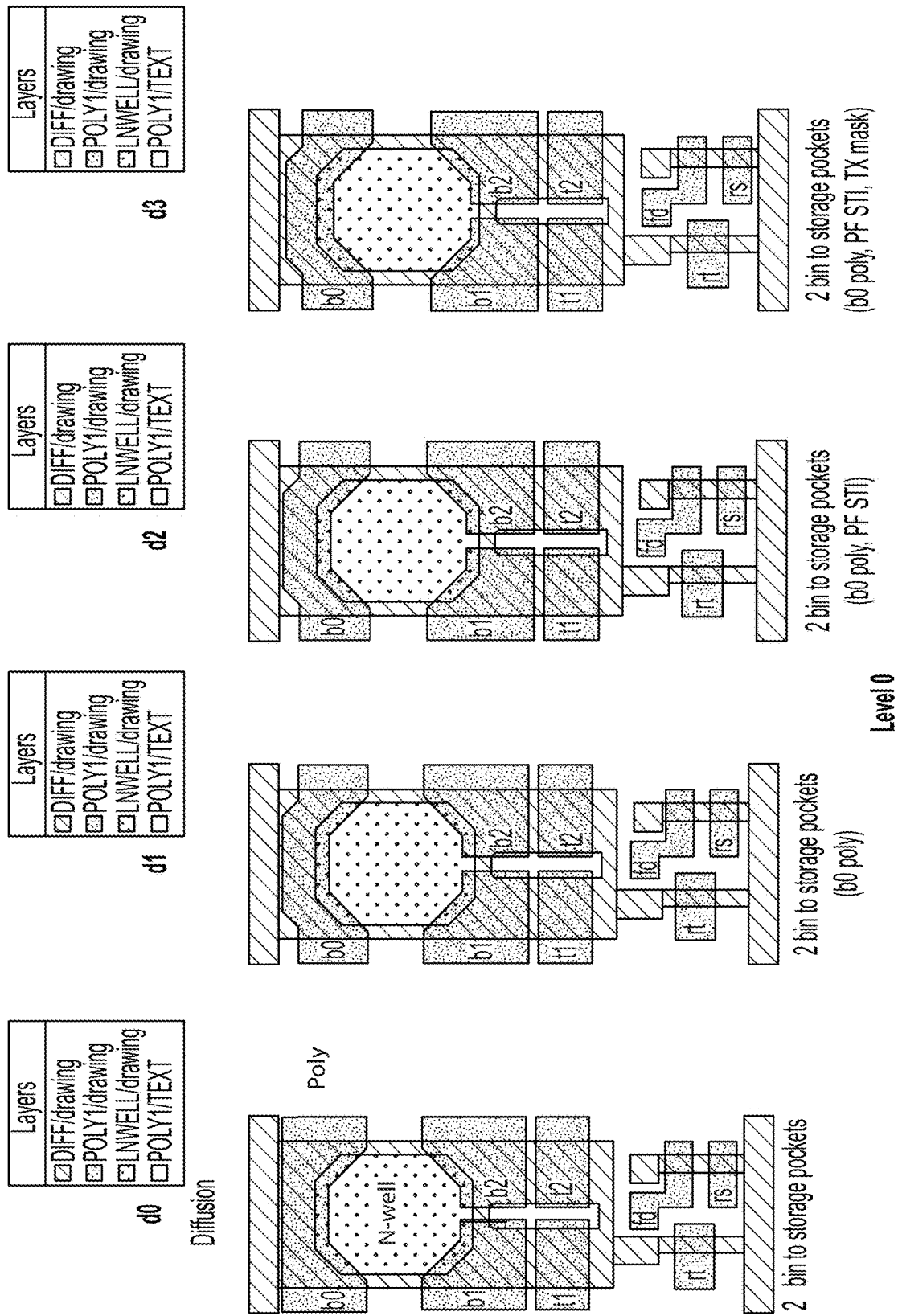
FIGS. 28-32 show an exemplary process of forming the photodetector and four different pixel designs d0-d3.
Figure 29:
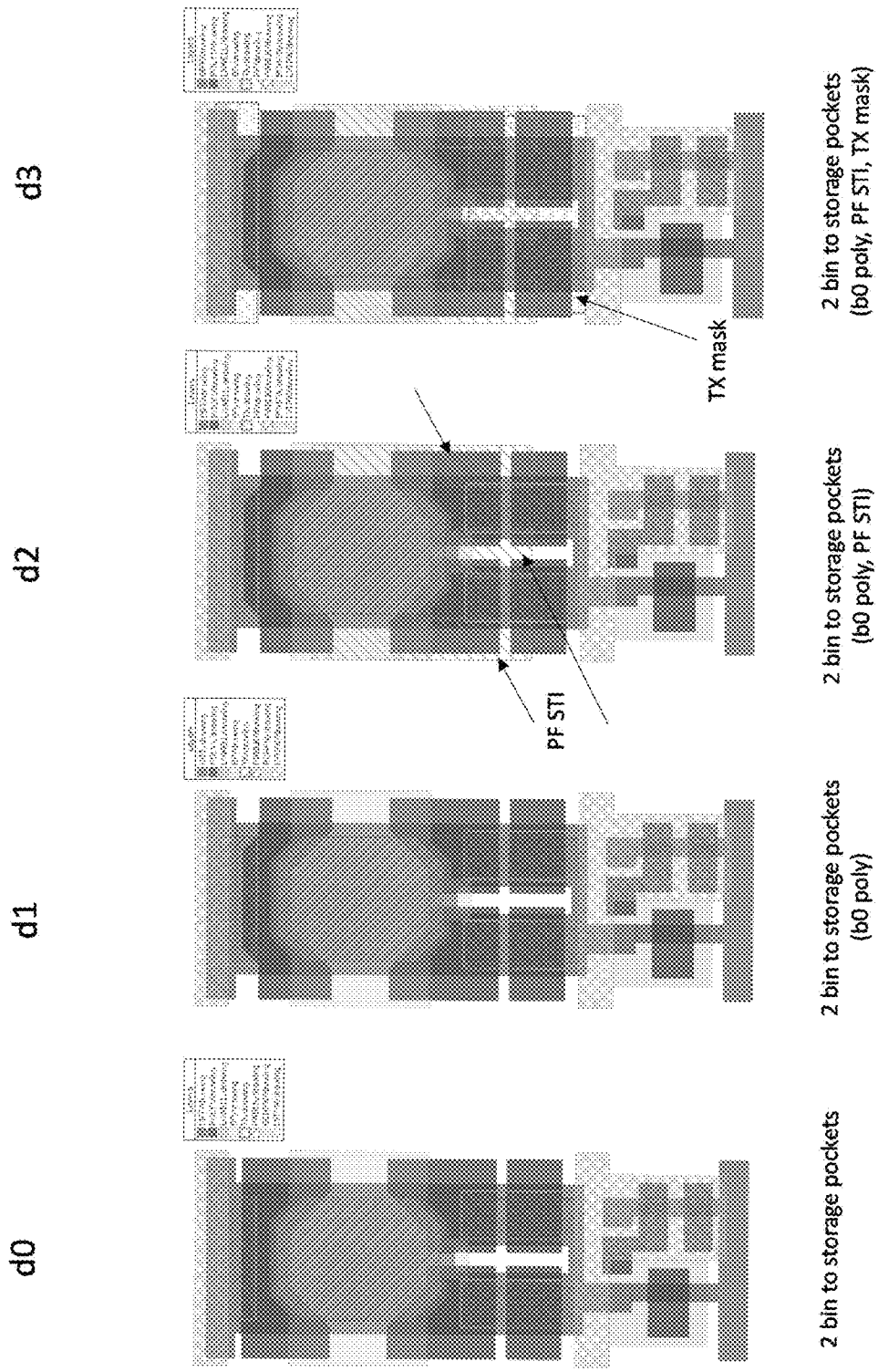
Figure 30:
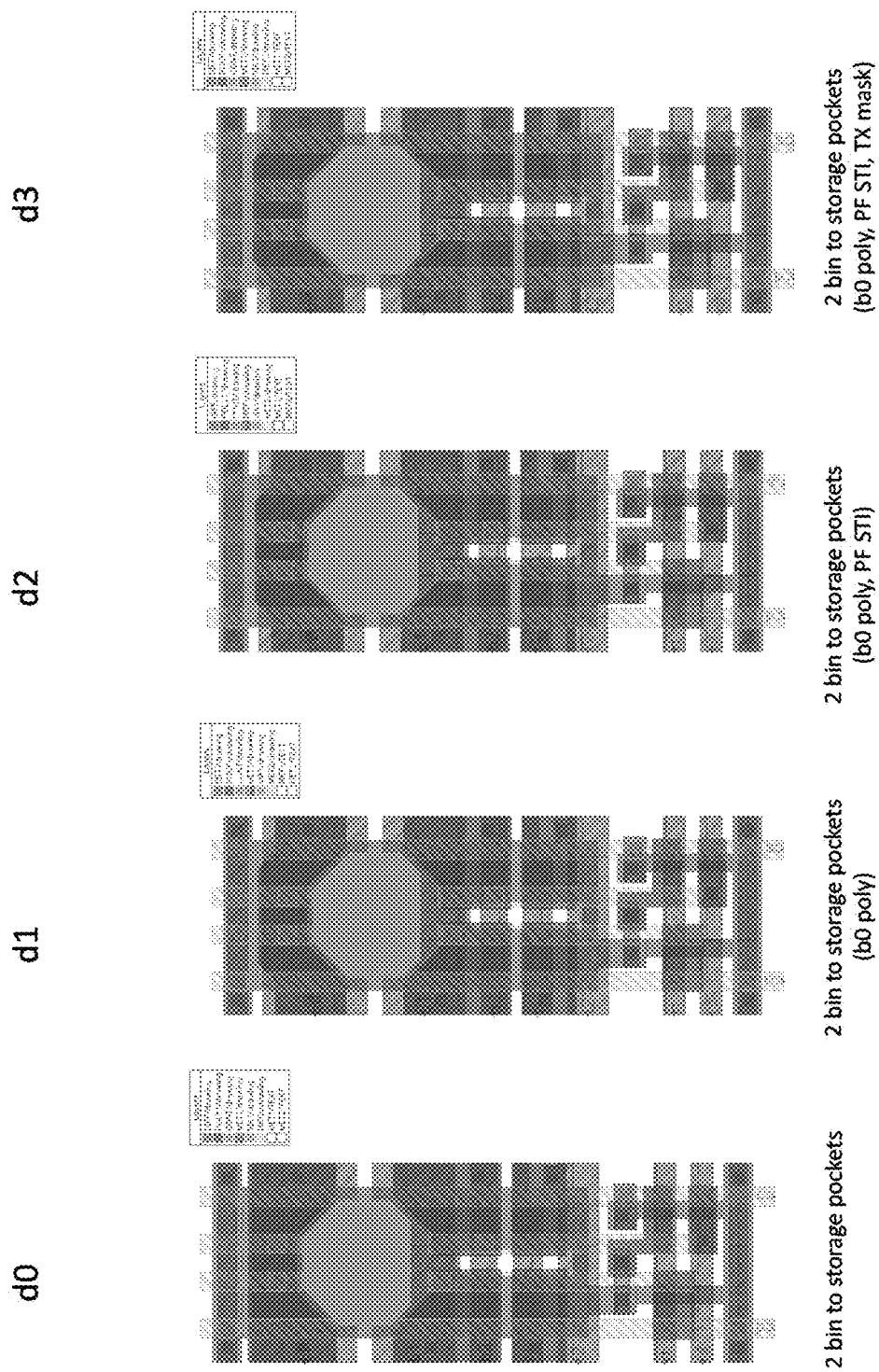
Figure 31:
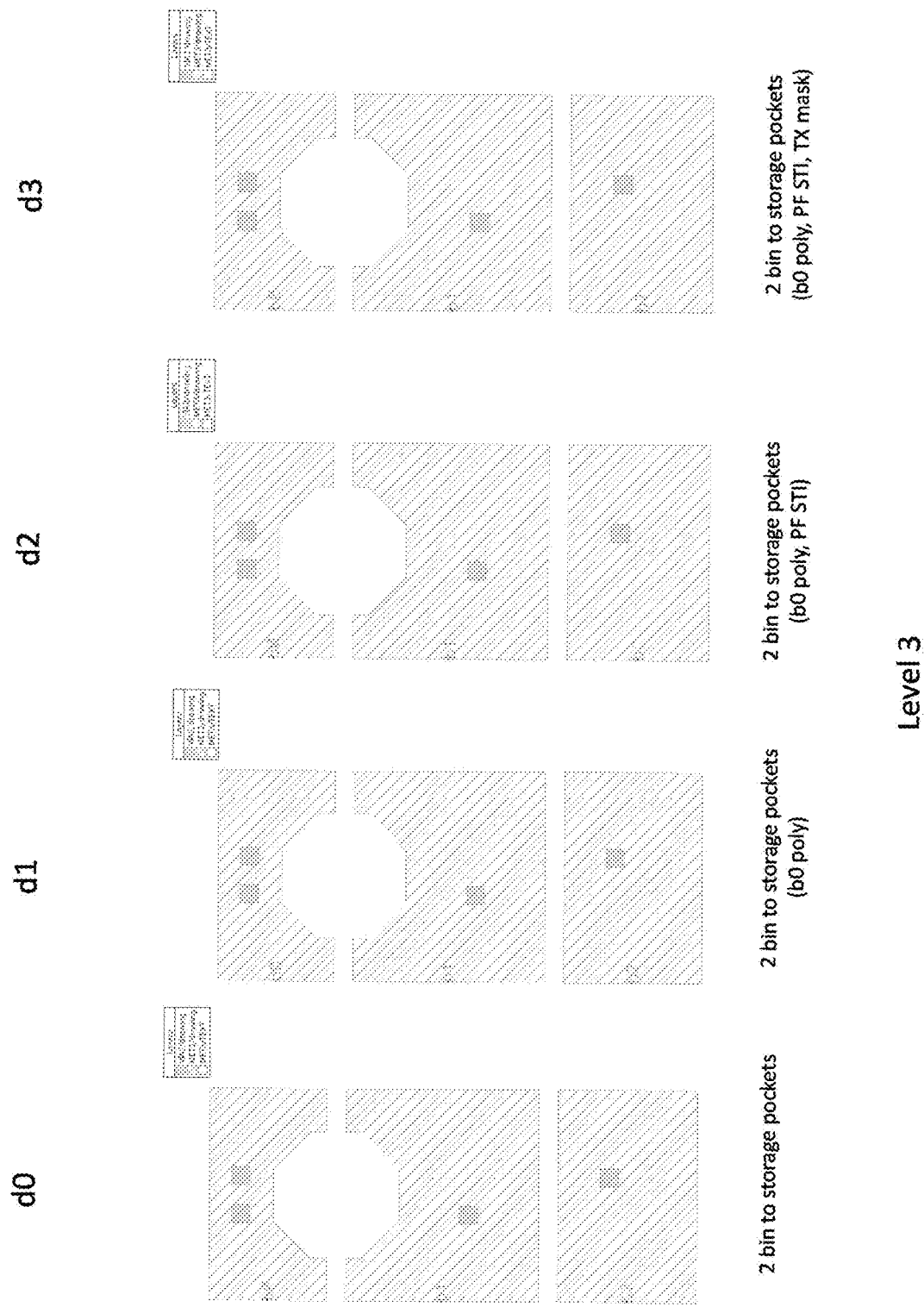
Figure 32:
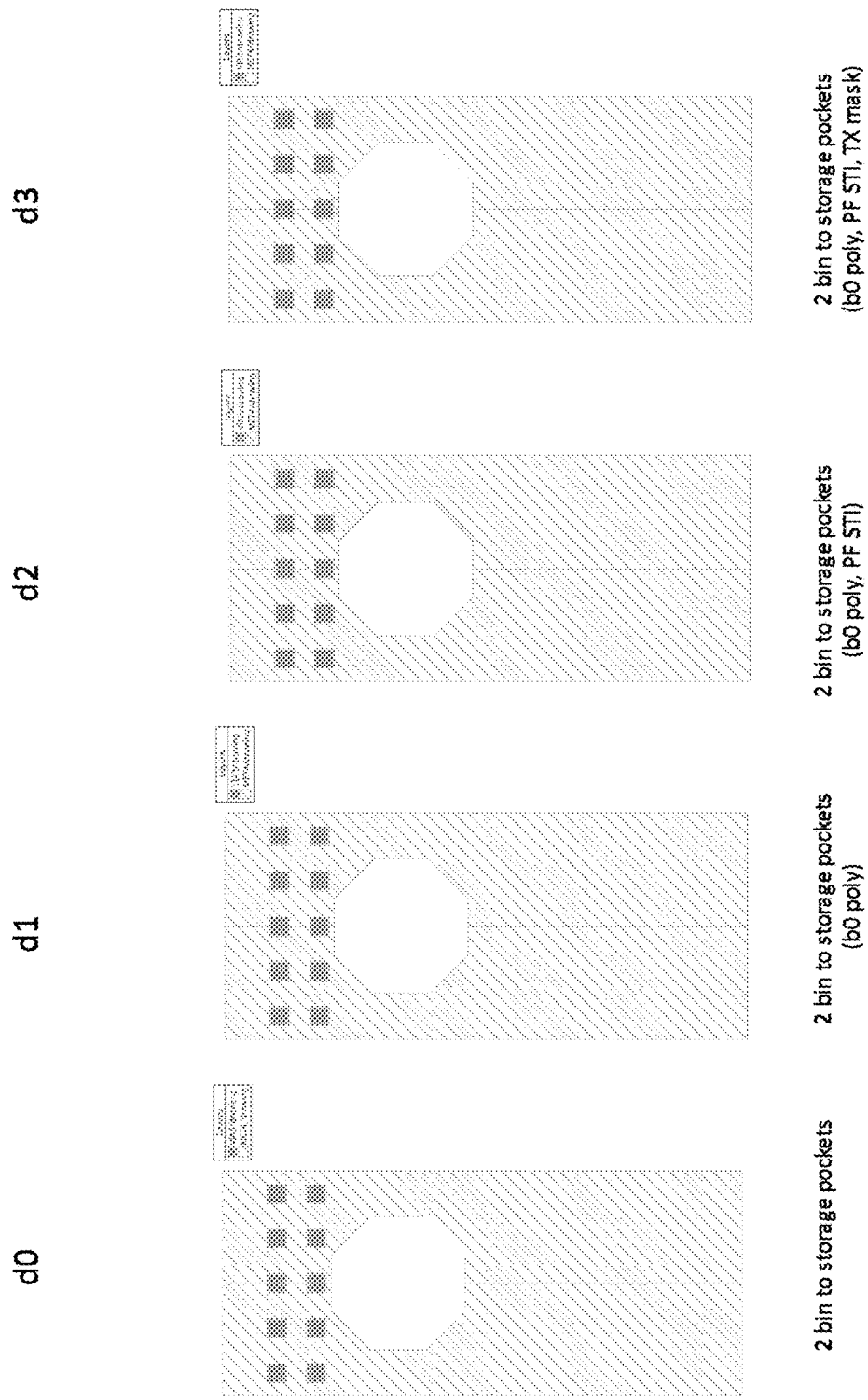

Example Integrated Circuit Realization and Method of Forming the Integrated Photodetector In some embodiments, the chip 1300 may be formed in a silicon substrate using a standard CMOS (Complementary Metal Oxide Semiconductor) process. However, the techniques described herein are not limited in this respect, as any suitable substrate or fabrication process may be used. FIGS. 28-32 show an exemplary process of forming the photodetector and four different pixel designs d0-d3. FIG. 28 shows Level 0 with diffusion and N-well regions in the semiconductor region, and an overlying poly electrode layer. FIG. 29 shows Level 1, FIG. 30 shows a Level 2, FIG. 31 shows Level 3 and FIG. 32 shows Level 4.

Pixel Array/Chip Architecture

Figure 33:
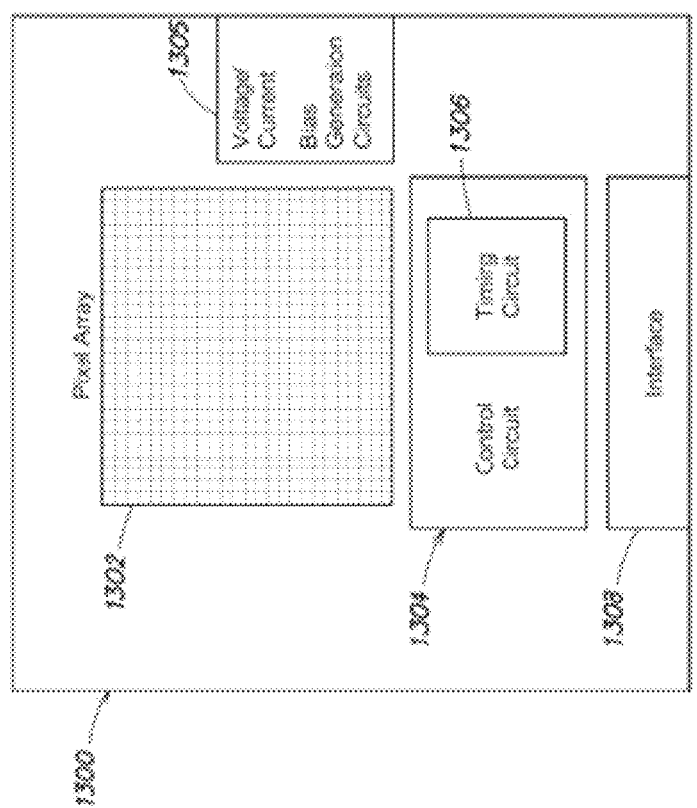
FIG. 33 shows a diagram of a chip architecture.

FIG. 33 shows a diagram of the chip architecture, according to some embodiments. As shown in FIG. 33, an integrated circuit or chip 1300 may include a pixel array 1302 including a plurality of pixels 100, a control circuit 1304 that includes a timing circuit 1306, voltage/current bias generation circuits 1305 and an interface 1308.

Pixel array 1302 includes an array of pixels 101 laid out in any suitable pattern, such as a rectangular pattern, for example. The pixel array 1302 may have any suitable number of pixels. The pixel array may have row and/or column conductors for reading out rows or columns of the pixel array 1302. Pixels may be read out in parallel, in series, or a combination thereof. For example, in some embodiments a row of pixels may be read out in parallel, and each row of the pixel array may be read out sequentially. However, the techniques described herein are not limited in this respect, as the pixels may be read out in any suitable manner.

The pixel array 1302 is controlled by a control circuit 1304. Control circuit 1304 may be any suitable type of control circuit for controlling operations on the chip 1300, including operations of the pixel array 1302. In some embodiments, control circuit 1304 may include a microprocessor programmed to control operations of the pixel array 1302 and any other operations on the chip 1300. The control circuit may include a computer readable medium (e.g., memory) storing computer readable instructions (e.g., code) for causing the microprocessor performing such operations. For example, the control circuit 1304 may control producing voltages to be applied to electrodes of the charge carrier segregation structure(s) in each pixel. The control circuit 1304 may change the voltages of one or more electrodes, as discussed above, to capture carriers, transfer carriers, and to perform readout of pixels and the array. The control circuit may set the timing of operations of the charge carrier segregation structure based on a stored timing scheme. The stored timing scheme may be fixed, programmable and/or adaptive, as discussed above.

The control circuit 1304 may include a timing circuit 1306 for timing operations of the charge carrier segregation structure(s) of the pixels or other operations of the chip. In some embodiments, timing circuit 1306 may enable producing signals to precisely control the timing of voltage changes in the charge carrier segregation structure(s) to accurately time bin charge carriers. In some embodiments the timing circuit 1306 may include an external reference clock and/or a delay-locked loop (DLL) for precisely setting the timing of the signals provided to the charge carrier segregation structure(s). In some embodiments, two single-ended delay lines may be used, each with half the number of stages aligned 180-degrees out of phase. However, any suitable technique may be used for controlling the timing of signals on the chip.

The chip 1300 may include an interface 1308 for sending signals from the chip 1300, receiving signals at the chip 1300, or both. The interface 1308 may enable reading out the signals sensed by the pixel array 1302. Readout from the chip 1300 may be performed using an analog interface and/or a digital interface. If readout from the chip 1300 is performed using a digital interface, the chip 1300 may have one or more analog to digital converters for converting signals read out from the pixel array 1302 into digital signals. In some embodiments, the readout circuit may include a Programmable Gain Amplifier. One or more control signals may be provided to the chip 1300 from an external source via interface 1308. For example, such control signals may control the type of measurements to be performed, which may include setting the timing of the time bins.

Analysis of signals read out from the pixel array 1302 may be performed by circuitry on-chip or off-chip. For example, in the context of fluorescence lifetime measurement, analysis of the timing of photon arrival may include approximating a fluorescence lifetime of a fluorophore. Any suitable type of analysis may be performed. If analysis of signals read out from the pixel array 1302 is performed on-chip, chip 1300 may have any suitable processing circuitry for performing the analysis. For example, chip 1300 may have a microprocessor for performing analysis that is part of or separate from control circuit 1304. If analysis is performed on-chip, in some embodiments the result of the analysis may be sent to an external device or otherwise provided off-chip through interface 1308. In some embodiments all or a portion of the analysis may be performed off-chip. If analysis is performed off-chip, the signals read out from the pixel array 1302 and/or the result of any analysis performed by the chip 1300, may be provided to an external device through interface 1308.

In some embodiments, the chip 1300 may include one or more of the following:

1) on-chip, digitally controlled, pixel bias generators (DACs).

2) on-chip, digitally programmable gain amplifiers that convert the single-ended pixel output voltage signal to a differential signal and applies gain to the signal 3) digitally-controlled amplifier bias generators that allow scaling the power dissipation with the output rate.

Figure 34:
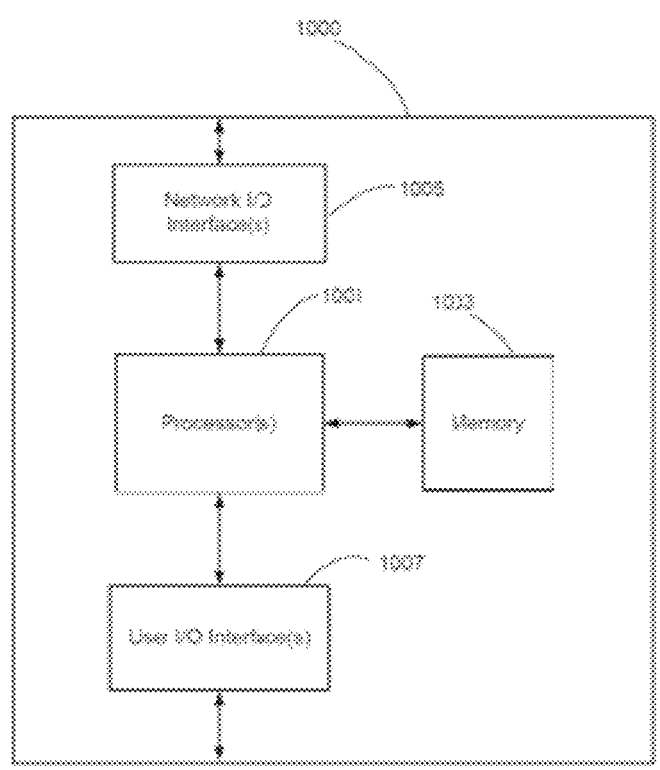
FIG. 34 is a block diagram of an illustrative computing device.

FIG. 34 is a block diagram of an illustrative computing device 1000 that may be used to implement a control circuit for controlling the pixel array or for performing analysis of the data from the pixels. Computing device 1000 may include one or more processors 1001 and one or more tangible, non-transitory computer-readable storage media (e.g., memory 1003). Memory 1003 may store, in a tangible non-transitory computer-recordable medium, computer program instructions that, when executed, implement any of the above-described functionality. Processor(s) 1001 may be coupled to memory 1003 and may execute such computer program instructions to cause the functionality to be realized and performed.

Computing device 1000 may also include a network input/output (I/O) interface 1005 via which the computing device may communicate with other computing devices (e.g., over a network), and may also include one or more user I/O interfaces 1007, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (i.e., a plurality of executable instructions) that, when executed on one or more processors, performs the above-discussed functions of one or more embodiments. The computer-readable medium may be transportable such that the program stored thereon can be loaded onto any computing device to implement aspects of the techniques discussed herein. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

Additional Aspects

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. An integrated circuit, comprising:
a photodetection region configured to receive incident photons, the photodetection region being configured to produce a plurality of charge carriers in response to the incident photons;
at least one charge carrier storage region;
a charge carrier segregation structure configured to selectively direct charge carriers of the plurality of charge carriers into the at least one charge carrier storage region based upon times at which the plurality of charge carriers are produced, wherein the charge carrier segregation structure is configured to transfer the plurality of charge carriers into the at least one charge carrier storage region without capturing the plurality of charge carriers between the photodetection region and the at least one charge carrier storage region, wherein the charge carrier segregation structure is configured to aggregate, in the at least one charge carrier storage region, first charge carriers produced in response to first photons of the incident photons, the first photons being produced by at least one luminescent molecule in response to excitation light pulses; and
a charge carrier rejection region configured to receive, during a rejection period, second charge carriers produced in the photodetection region in response to second photons of the incident photons, the excitation light pulses comprising the second photons.

2. The integrated circuit of claim 1, further comprising a pixel, the pixel comprising the photodetection region, the at least one charge carrier storage region and the charge carrier segregation structure.

3. The integrated circuit of claim 2, wherein the integrated circuit comprises a plurality of pixels.

4. The integrated circuit of claim 1, wherein the at least one charge carrier storage region comprises a plurality of charge carrier storage regions.

5. The integrated circuit of claim 1, wherein the charge carrier segregation structure comprises at least one electrode at a boundary between the photodetection region and a first charge carrier storage region of the at least one charge carrier storage region.

6. The integrated circuit of claim 5, wherein the charge carrier segregation structure comprises a single electrode at the boundary between the photodetection region and the first charge carrier storage region.

7. The integrated circuit of claim 1, wherein the second charge carriers are removed from the photodetection region in a different direction from a direction in which carriers are directed from the photodetection region toward the at least one charge carrier storage region.

8. The integrated circuit of claim 1, further comprising an electrode at a boundary between the photodetection region and the charge carrier rejection region.

9. The integrated circuit of claim 1, wherein single photons are transferred to the at least one charge carrier storage region and aggregated in the at least one charge carrier storage region.

10. The integrated circuit of claim 1, wherein the photodetection region is formed in a semiconductor substrate, and wherein charge carriers deeper than one micron below a surface of the semiconductor substrate are rejected.

11. The integrated circuit of claim 10, wherein charge carriers deeper than one micron below the surface of the semiconductor substrate are rejected at least partially by an implant below a photodiode of the photodetection region.

12. The integrated circuit of claim 11, wherein the implant provides a deep shield or a deep drain.

13. The integrated circuit of claim 12, wherein the implant is N-type or P+-type.

14. The integrated circuit of claim 10, wherein charge carriers deeper than one micron below the surface of the semiconductor substrate are rejected by a drift field below the surface of the semiconductor substrate.

15. The integrated circuit of claim 1, wherein the photodetection region is formed in an epitaxial region that is less than two microns deep.

16. The integrated circuit of claim 1, wherein the photodetection region is an epitaxial region comprising a photodiode.

17. The integrated circuit of claim 1, wherein the at least one charge carrier storage region comprises a plurality of charge carrier storage regions.

18. A photodetection method, comprising:
(A) receiving incident photons at a photodetection region;
(B) selectively directing charge carriers of a plurality of charge carriers produced in response to the incident photons from the photodetection region into at least one charge carrier storage region based upon times at which the charge carriers are produced, wherein the charge carriers are transferred into the at least one charge carrier storage region without capturing the charge carriers between the photodetection region and the at least one charge carrier storage region and aggregating, in the at least one charge carrier storage region, first charge carriers produced in response to first photons of the incident photons, the first photons being produced by at least one luminescent molecule in response to excitation light pulses; and
(C) receiving, by a charge carrier rejection region, and during a rejection period, second charge carriers produced in the photodetection region in response to second photons of the incident photons, the excitation light pulses comprising the second photons.

19. The photodetection method of claim 18, wherein a charge carrier in the photodetection region is transferred to a rejection region during a rejection period, then a first potential barrier to a first charge carrier storage region is lowered, then a second potential barrier to a second charge carrier storage region is lowered.

20. The photodetection method of claim 19, wherein the first potential barrier is controlled by a first electrode and the second potential barrier is controlled by a second electrode.

21. An integrated circuit, comprising:
a photodetection region configured to receive incident photons, the photodetection region being configured to produce a plurality of charge carriers in response to the incident photons;
at least one charge carrier storage region;
a charge carrier segregation structure configured to selectively direct charge carriers of the plurality of charge carriers into the at least one charge carrier storage region based upon times at which the plurality of charge carriers are produced;
a barrier below the photodetection region, the barrier being configured to inhibit unwanted charge carriers from entering the photodetection region, and
a drain below the photodetection region to remove the unwanted charge carriers, wherein the barrier is between the photodetection region and the drain.

22. The integrated circuit of claim 21, wherein the barrier is a doped region.

23. The integrated circuit of claim 22, wherein the photodetection region comprises a photodiode.

24. The integrated circuit of claim 23, wherein the photodiode comprises a region having a first conductivity type and the doped region has a second conductivity type.

* * * * *